United States Patent
McDonald et al.

(10) Patent No.: US 7,491,746 B2
(45) Date of Patent: Feb. 17, 2009

(54) COMPOUNDS, COMPOSITIONS AND METHODS

(75) Inventors: Andrew McDonald, San Francisco, CA (US); Gustave Bergnes, Pacifica, CA (US); Bainian Feng, Foster City, CA (US); David J. Morgans, Jr., Los Altos, CA (US); Steven David Knight, West Chester, PA (US); Kenneth A. Newlander, West Chester, PA (US); Dashyant Dhanak, West Chester, PA (US); Christopher A. Brook, Philadelphia, PA (US)

(73) Assignees: Cytokinetics, Inc., South San Francisco, CA (US); SmithKline Beecham Corporation, Philadelphia, PA (US)

( * ) Notice: Subject to any disclaimer, the term of this patent is extended or adjusted under 35 U.S.C. 154(b) by 513 days.

(21) Appl. No.: 11/154,989

(22) Filed: Jun. 15, 2005

(65) Prior Publication Data

US 2006/0020008 A1    Jan. 26, 2006

Related U.S. Application Data

(63) Continuation of application No. 10/412,712, filed on Apr. 11, 2003, now Pat. No. 6,924,376.

(60) Provisional application No. 60/373,454, filed on Apr. 17, 2002, provisional application No. 60/410,682, filed on Sep. 13, 2002.

(51) Int. Cl.
*A61K 31/353* (2006.01)
(52) U.S. Cl. .................................................. 514/457
(58) Field of Classification Search ................. 514/402, 514/457
See application file for complete search history.

(56) References Cited

U.S. PATENT DOCUMENTS

| | | |
|---|---|---|
| 4,434,296 A | 2/1984 | Gammill |
| 4,482,558 A | 11/1984 | Richardson et al. |
| 4,841,077 A | 6/1989 | Ito et al. |
| 4,900,727 A | 2/1990 | Kattige et al. |
| 4,904,690 A | 2/1990 | Aono et al. |
| 4,954,518 A | 9/1990 | Takano et al. |
| 4,977,162 A | 12/1990 | Huang et al. |
| 5,032,598 A | 7/1991 | Baldwin et al. |
| 5,082,849 A | 1/1992 | Huang et al. |
| 5,158,959 A | 10/1992 | Geiger et al. |
| 5,180,717 A | 1/1993 | Gammill et al. |
| 5,215,989 A | 6/1993 | Baldwin et al. |
| 5,284,856 A | 2/1994 | Naik et al. |
| 5,304,548 A | 4/1994 | Gammill et al. |
| 5,401,766 A | 3/1995 | Geiger et al. |
| H1427 H | 4/1995 | Briet et al. |
| 5,574,061 A | 11/1996 | Shiota et al. |
| 5,605,896 A | 2/1997 | Leonardi et al. |
| 5,607,928 A | 3/1997 | Arnould |
| 5,614,642 A | 3/1997 | Tang et al. |
| 5,703,075 A | 12/1997 | Gammill et al. |
| 5,714,142 A | 2/1998 | Blaney et al. |
| 5,843,989 A | 12/1998 | Vong et al. |
| 6,028,088 A | 2/2000 | Pershadsingh et al. |
| 6,087,385 A | 7/2000 | Pershadsingh et al. |
| 6,545,004 B1 | 4/2003 | Finer et al. |
| 6,545,005 B1 | 4/2003 | Baxter et al. |
| 6,559,145 B2 | 5/2003 | Ciske et al. |
| 6,559,160 B1 | 5/2003 | Schall et al. |
| 6,608,089 B2 | 8/2003 | Bombardelli et al. |
| 6,646,136 B1 | 11/2003 | Bokel et al. |
| 6,924,376 B2 | 8/2005 | McDonald et al. |
| 2002/0169159 A1 | 11/2002 | Medina et al. |
| 2003/0055054 A1 | 3/2003 | Medina et al. |
| 2004/0043985 A1 | 3/2004 | Hicks et al. |
| 2004/0116400 A1 | 6/2004 | McDonald et al. |
| 2005/0119269 A1 | 6/2005 | Rao et al. |
| 2005/0165089 A1 | 7/2005 | Bergnes et al. |
| 2006/0004073 A1 | 1/2006 | McDonald et al. |

FOREIGN PATENT DOCUMENTS

| | | |
|---|---|---|
| DE | 198 50 131 A1 | 5/2000 |
| EP | 0 094 769 | 11/1983 |
| EP | 0 099 172 A1 | 1/1984 |
| EP | 0 241 003 | 10/1987 |
| EP | 0 341 104 B1 | 11/1989 |
| EP | 0 366 061 A1 | 5/1990 |
| GB | 728757 | 4/1955 |
| WO | WO 90/06921 A1 | 6/1990 |
| WO | WO 91/19707 A2 | 12/1991 |
| WO | WO 92/06086 A1 | 4/1992 |
| WO | WO 93/15065 A1 | 8/1993 |

(Continued)

OTHER PUBLICATIONS

International Search Report and Written Opinion mailed Jul. 18, 2005, for Application No. PCT/US2004/32569, filed Oct. 5, 2004.
Bergnes et al., "Compounds, Compositions and Methods," U.S. Appl. No. 10/959,610, filed Oct. 5, 2004.
Eiden et al., "Xanthone aus Chromon-Derivaten," *Arch. Pharm.* (Weinheim), 317/84: 539-547 (1984).
Lacova et al., "Evaluation of Effect of Microwave Irradiation on Syntheses and Reactions of Some New 3-Acyl-methylchromones," *Molecules*, 3: 120-131 (1998).
Ogawara et al., "Inhibition of Tyrosine Protein Kinase Activity by Synthetic Isoflavones and Flavones," *J. Antibiotics*, 42(2): 340-343 (Feb. 1989).

(Continued)

*Primary Examiner*—Taofiq A Solola
(74) *Attorney, Agent, or Firm*—Finnegan, Henderson, Farabow, Garrett & Dunner, LLP

(57) ABSTRACT

Compounds useful for treating cellular proliferative diseases and disorders by modulating the activity of KSP are disclosed.

26 Claims, 3 Drawing Sheets

FOREIGN PATENT DOCUMENTS

| | | |
|---|---|---|
| WO | WO 94/01434 A1 | 1/1994 |
| WO | WO 95/22992 | 8/1995 |
| WO | WO 96/07409 A1 | 3/1996 |
| WO | WO 96/40109 | 12/1996 |
| WO | WO 97/14419 A1 | 4/1997 |
| WO | WO 98/13344 A1 | 4/1998 |
| WO | WO 99/52890 A1 | 10/1999 |
| WO | WO 00/26212 A1 | 5/2000 |
| WO | WO 00/69827 A1 | 11/2000 |
| WO | WO 01/17985 A1 | 3/2001 |
| WO | WO 01/17988 A1 | 3/2001 |
| WO | WO 02/04444 A2 | 1/2002 |
| WO | WO 02/30421 A2 | 4/2002 |
| WO | WO 02/07515 A2 | 9/2002 |
| WO | WO 03/011219 A2 | 2/2003 |
| WO | WO 03/027234 A2 | 3/2003 |
| WO | WO 03/037871 A1 | 5/2003 |
| WO | WO 03/039460 A2 | 5/2003 |
| WO | WO 03/049527 A2 | 6/2003 |
| WO | WO 03/049678 A2 | 6/2003 |
| WO | WO 03/049679 A2 | 6/2003 |
| WO | WO 03/050064 A2 | 6/2003 |
| WO | WO 03/050122 A2 | 6/2003 |
| WO | WO 03/079973 A2 | 10/2003 |
| WO | WO 03/088903 A2 | 10/2003 |
| WO | WO 03/088903 A3 | 10/2003 |
| WO | WO 03/099211 A2 | 12/2003 |
| WO | WO 03/105855 A1 | 12/2003 |
| WO | WO 03/106417 A1 | 12/2003 |
| WO | WO 2004/004652 A2 | 1/2004 |
| WO | WO 2004/006865 A2 | 1/2004 |
| WO | WO 2004/006865 A3 | 1/2004 |
| WO | WO 2004/014388 A1 | 2/2004 |
| WO | WO 2005/040163 A1 | 5/2005 |

OTHER PUBLICATIONS

Office Action mailed Oct. 6, 2004, for U.S. Appl. No. 10/622,363, filed Jul. 17, 2003.
Office Action mailed Jan. 9, 2008, for U.S. Appl. No. 10/959,610, filed Oct. 5, 2004.
Advisory Action mailed Mar. 27, 2008, for U.S. Appl. No. 10/959,610, filed Oct. 5, 2004.
International Search Report and Written Opinion mailed Jun. 18, 2005, for Application No. PCT/US2004/32569, filed Oct. 5, 2004.
Notice of Allowance mailed Mar. 11, 2005 for U.S. Appl. No. 10/412,712, filed Apr. 11, 2003.
Notice of Allowance mailed Mar. 29, 2005 for U.S. Appl. No. 10/622,363, filed Jul. 17, 2003.
Office Action mailed Jun. 19, 2007, for U.S. Appl. No. 11/172,400, filed Jun. 29, 2005.
Office Action mailed Sep. 6, 2007, for U.S. Appl. No. 10/959,610, filed Oct. 5, 2004.
International Search Report mailed Aug. 11, 2004, for Application No. PCT/US2003/011432, filed Apr. 11, 2003.
International Search Report mailed Apr. 30, 2004, for Application No. PCT/US2003/022466, filed Jul. 17, 2003.
International Preliminary Examination Report issued Sep. 19, 2004, for Application No. PCT/US2003/011432, filed Apr. 11, 2003.
International Preliminary Examination Report issued Jul. 5, 2004, for Application No. PCT/US2003/022466, filed Jul. 17, 2003.
Office Action mailed Dec. 21, 2007, for U.S. Appl. No. 11/172,400, filed Jun. 29, 2005.
STN Accession No. 1966:22235; Document No. 64:22235.
STN Accession No. 1995:679158: Document No. 123:102034.

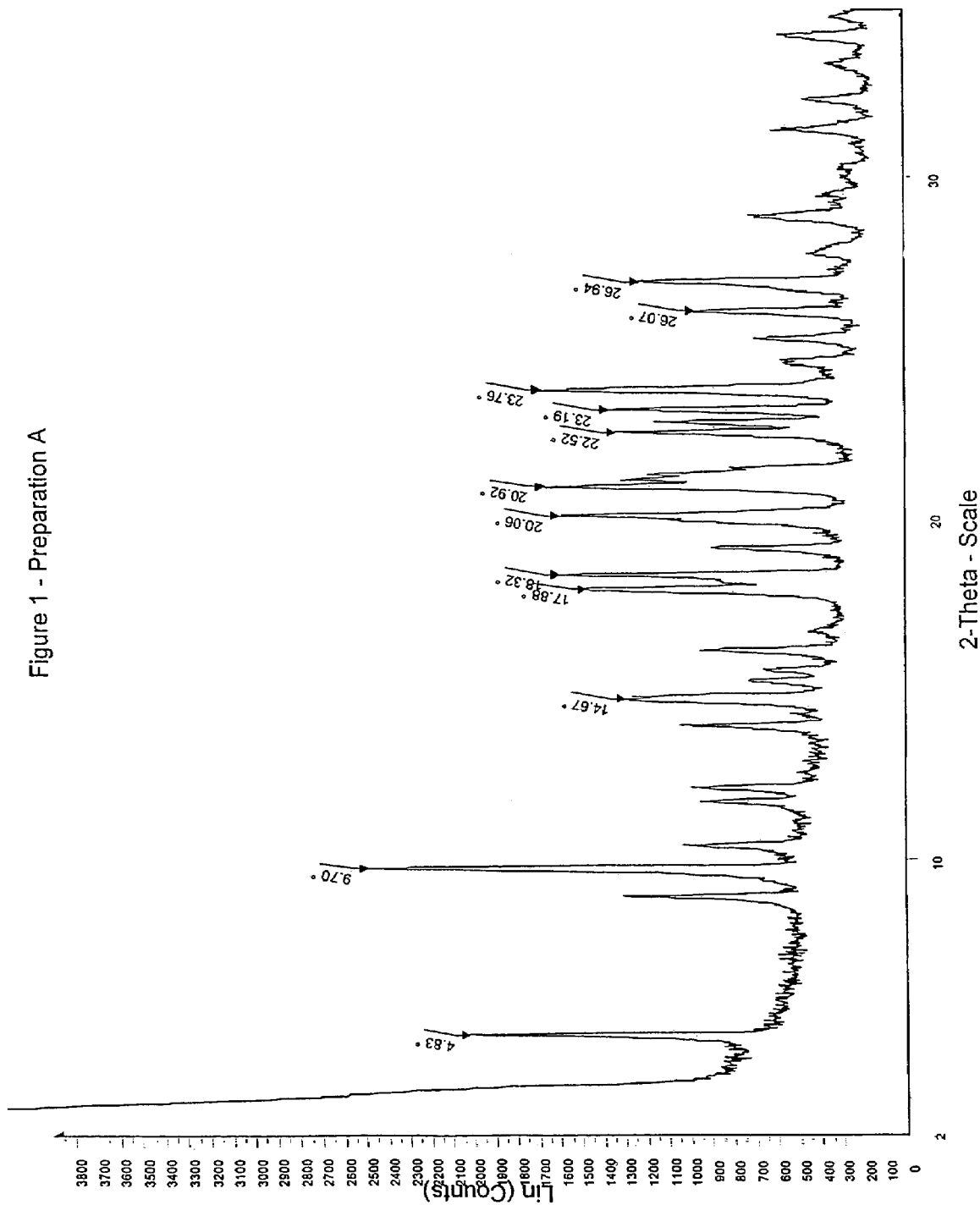
Figure 1 - Preparation A

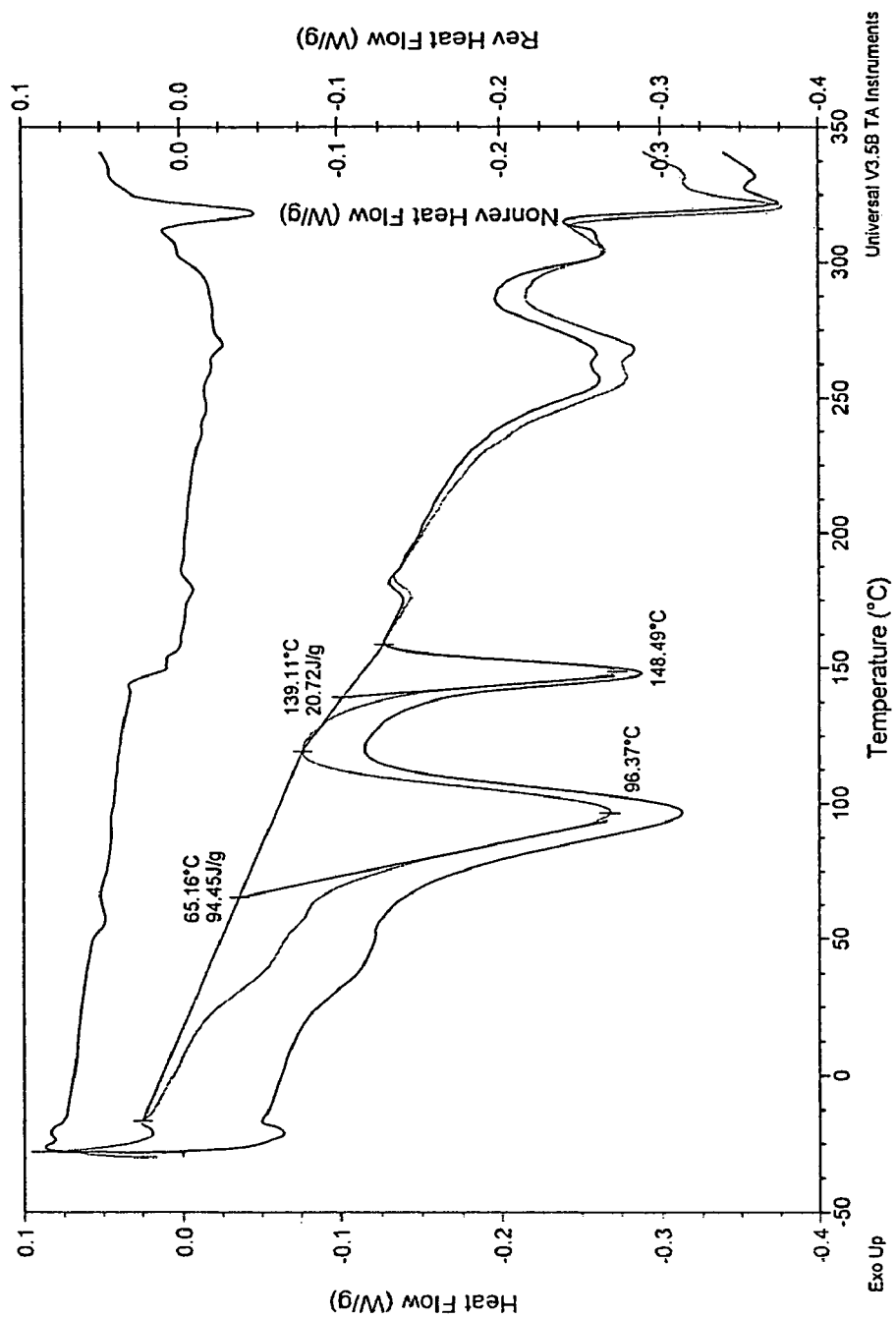
Figure 2 - Preparation A

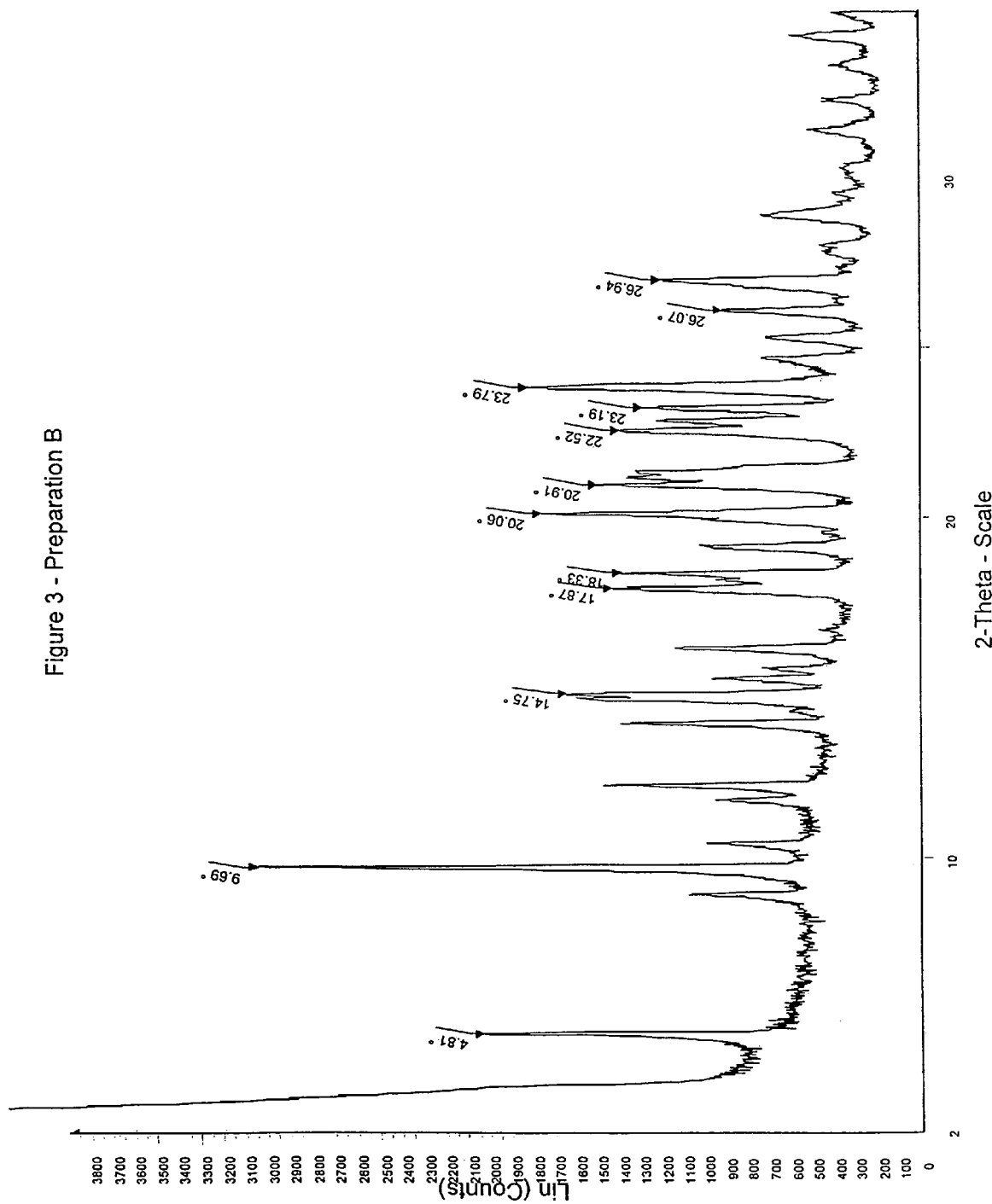
Figure 3 - Preparation B

COMPOUNDS, COMPOSITIONS AND METHODS

CROSS-REFERENCE TO RELATED PATENT APPLICATIONS

This application is a con of Ser. No. 10/412,712, filed Apr. 11, 2003 now U.S. Pat. No. 6,924,376, which claims the benefit of U.S. Provisional Patent Application No. 60/373,454, filed Apr. 17, 2002; and of U.S. Provisional Patent Application No. 60/410,682, filed Sep. 13, 2002. Each of these applications is incorporated herein by reference for all purposes.

FIELD OF THE INVENTION

This invention relates to compounds which are inhibitors of the mitotic kinesin KSP and are useful in the treatment of cellular proliferative diseases, for example cancer, hyperplasias, restenosis, cardiac hypertrophy, immune disorders, fungal disorders, and inflammation.

BACKGROUND OF THE INVENTION

Among the therapeutic agents used to treat cancer are the taxanes and vinca alkaloids, which act on microtubules. Microtubules are the primary structural element of the mitotic spindle. The mitotic spindle is responsible for distribution of replicate copies of the genome to each of the two daughter cells that result from cell division. It is presumed that disruption of the mitotic spindle by these drugs results in inhibition of cancer cell division, and induction of cancer cell death. However, microtubules form other types of cellular structures, including tracks for intracellular transport in nerve processes. Because these agents do not specifically target mitotic spindles, they have side effects that limit their usefulness.

Improvements in the specificity of agents used to treat cancel is of considerable interest because of the therapeutic benefits which would be realized if the side effects associated with the administration of these agents could be reduced. Traditionally, dramatic improvements in the treatment of cancer are associated with identification of therapeutic agents acting through novel mechanisms. Examples of this include not only the taxanes, but also the camptothecin class of topoisomerase I inhibitors. From both of these perspectives, mitotic kinesins are attractive targets for new anti-cancer agents.

Mitotic kinesins are enzymes essential for assembly and function of the mitotic spindle, but are not generally part of other microtubule structures, such as in nerve processes. Mitotic kinesins play essential roles during all phases of mitosis. These enzymes are "molecular motors" that transform energy released by hydrolysis of ATP into mechanical force which drives the directional movement of cellular cargoes along microtubules. The catalytic domain sufficient for this task is a compact structure of approximately 340 amino acids. During mitosis, kinesins organize microtubules into the bipolar structure that is the mitotic spindle. Kinesins mediate movement of chromosomes along spindle microtubules, as well as structural changes in the mitotic spindle associated with specific phases of mitosis. Experimental perturbation of mitotic kinesin function causes malformation or dysfunction of the mitotic spindle, frequently resulting in cell cycle arrest and cell death.

Among the mitotic kinesins which have been identified is KSP. KSP belongs to an evolutionarily conserved kinesin subfamily of plus end-directed microtubule motors that assemble into bipolar homotetramers consisting of antiparallel homodimers. During mitosis KSP associates with microtubules of the mitotic spindle. Microinjection of antibodies directed against KSP into human cells prevents spindle pole separation during prometaphase, giving rise to monopolar spindles and causing mitotic arrest and induction of programmed cell death. KSP and related kinesins in other, non-human, organisms, bundle antiparallel microtubules and slide them relative to one another, thus forcing the two spindle poles apart. KSP may also mediate in anaphase B spindle elongation and focussing of microtubules at the spindle pole.

Human KSP (also termed HsEg5) has been described (Blangy, et al. Cell, 83:1159-69 (1995); Whitehead, et al., Arthritis Rheum., 39:1635-42 (1996); Galgio et al., J. Cell Biol., 135:339-414 (1996); Blangy, et al., J. Biol. Chem., 272:19418-24 (1997): Blangy, et al., Cell Motil Cytoskeleton, 40:174-82 (1998); Whitehead and Rattner, J. Cell Sci., 111:2551-61 (1998); Kaiser, et al., JBC 274:18925-31 (1999): GenBank accession numbers: X85137, NM004523 and U37426), and a fragment of the KSP gene (TRIP5) has been described (Lee, et al., Mol Endocrinol., 9:243-54 (1995); GenBank accession number L40372). Xenopus KSP homologs (Eg5), as well as Drosophila KLP61 F/KRPI 30 have been reported.

Mitotic kinesins, including KSP, are attractive targets for the discovery and development of novel antimitotic chemotherapeutics. Accordingly, it is an object of the present invention to provide compounds, compositions and methods useful in the inhibition of KSP.

SUMMARY OF THE INVENTION

In accordance with the objects outlined above, the present invention provides compounds that can be used to treat cellular proliferative diseases. The compounds are KSP inhibitors, particularly human KSP inhibitors. The present invention also provides compositions comprising such compounds, and methods utilizing such compounds or compositions, which can be used to treat cellular proliferative diseases.

In one aspect, the invention relates to methods for treating cellular proliferative diseases, and for treating disorders by inhibiting the activity of KSP. The methods employ compounds represented by Formula I:

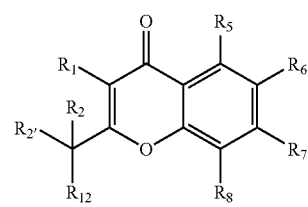

Formula I wherein:

$R_1$ is chosen from hydrogen, optionally substituted alkyl-, optionally substituted aryl-, optionally substituted aralkyl-, optionally substituted heteroaryl-, and optionally substituted heteroaralkyl-;

$R_2$ and $R_{2'}$ are independently chosen from hydrogen, optionally substituted alkyl-, optionally substituted alkoxy, optionally substituted aryl-, optionally substituted aralkyl-, optionally substituted heteroaryl-, and optionally substituted heteroaralkyl-; or $R_2$ and $R_{2'}$ taken together form an optionally substituted 3- to 7-membered ring:

$R_{12}$ is selected from the group consisting of optionally substituted imidazolyl, optionally substituted imidazolinyl, —NHR$_4$; —N(R$_4$)(COR$_3$); —N(R$_4$)(SO$_2$R$_{3a}$); and —N(R$_4$)(CH$_2$R$_{3b}$);

$R_3$ is chosen from hydrogen, optionally substituted alkyl-, optionally substituted aryl-, optionally substituted aralkyl-, optionally substituted heteroaryl-, optionally substituted heteroaralkyl-, $R_{15}$O— and $R_{17}$—NH—;

$R_{3a}$ is chosen from optionally substituted alkyl-, optionally substituted aryl-, optionally substituted aralkyl-, optionally substituted heteroaryl-, optionally substituted heteroaralkyl-, and $R_{17}$—NH—;

$R_{3b}$ is chosen from hydrogen, optionally substituted alkyl-, optionally substituted aryl-, optionally substituted aralkyl-, optionally substituted heteroaryl-, and optionally substituted heteroaralkyl-;

$R_4$ is chosen from hydrogen, optionally substituted alkyl-, optionally substituted aryl-, optionally substituted aralkyl-, optionally substituted hetercyclyl-, and optionally substituted heteroaralkyl-;

$R_5$, $R_6$, $R_7$ and $R_8$ are independently chosen from hydrogen, acyl, optionally substituted alkyl-, optionally substituted alkoxy, halogen, hydroxyl, nitro, cyano, dialkylamino, alkylsulfonyl-, alkylsulfonamido-, alkylthio-, carboxyalkyl-, carboxamido-, aminocarbonyl-, optionally substituted aryl and optionally substituted heteroaryl-;

$R_{15}$ is chosen from optionally substituted alkyl-, optionally substituted aryl-, optionally substituted aralkyl-, optionally substituted heteroaryl-, and optionally substituted heteroaralkyl-; and $R_{17}$ is hydrogen, optionally substituted alkyl-, optionally substituted aryl-, optionally substituted aralkyl-, optionally substituted heteroaryl-, or optionally substituted hetero-aralkyl-, including single stereoisomers, mixtures of stereoisomers;

a pharmaceutically acceptable salt of a compound of Formula I;

a pharmaceutically acceptable solvate of a pharmaceutically acceptable solvate of a compound of Formula I; or a pharmaceutically acceptable solvate of a pharmaceutically acceptable salt of a compound of Formula I.

According to one embodiment, when either $R_2$ or $R_{2'}$ is hydrogen, the other is not hydrogen. In another embodiment, $R_2$ and $R_{2'}$ are each hydrogen; and $R_1$ is chosen from optionally substituted aryl, optionally substituted aralkyl, optionally substituted heteroaryl, and optionally substituted heteroaralkyl, provided however, that $R_1$ is not substituted phenyl.

In one aspect, the invention relates to methods for treating cellular proliferative diseases and other disorders that can be treated by inhibiting KSP by the administration of a therapeutically effective amount of a compound of Formula I: a pharmaceutically acceptable salt of a compound of Formula I; or a pharmaceutically acceptable solvate of a pharmaceutically acceptable salt of a compound of Formula I, thereof. Such diseases and disorders include cancer, hyperplasia, restenosis, cardiac hypertrophy, immune disorders, fungal disorders and inflammation.

In another aspect, the invention relates to compounds useful in inhibiting KSP kinesin. The compounds have the structures shown above in Formula I; a pharmaceutically acceptable salt of a compound of Formula I; or a pharmaceutically acceptable solvate of a pharmaceutically acceptable salt of a compound of Formula I. The invention also relates to pharmaceutical compositions containing a therapeutically effective amount of a compound of Formula I; a pharmaceutically acceptable salt of a compound of Formula I; or a pharmaceutically acceptable solvate of a pharmaceutically acceptable salt of a compound of Formula I, admixed with at least one pharmaceutical excipient. In another aspect, the composition further comprises a chemotherapeutic agent other than a compound of the present invention.

In an additional aspect, the present invention provides methods of screening for compounds that will bind to a KSP kinesin, for example compounds that will displace or compete with the binding of a compound of the invention. The methods comprise combining a labeled compound of the invention, a KSP kinesin, and at least one candidate agent and determining the binding of the candidate agent to the KSP kinesin.

In a further aspect, the invention provides methods of screening for modulators of KSP kinesin activity. The methods comprise combining a compound of the invention, a KSP kinesin, and at least one candidate agent and determining the effect of the candidate agent on the KSP kinesin activity.

BRIEF DESCRIPTION OF THE FIGURES

The invention will be better understood by reference to the following description taken in conjunction with the accompanying drawings.

FIGS. 1 and 2 represent a XRPD and MDSC scan, respectively, of a salt prepared according to Preparation A.

FIG. 3 represents an XRPD scan of a salt prepared according to Preparation B.

DETAILED DESCRIPTION OF THE INVENTION

Definitions

As used in the present specification, the following words and phrases are generally intended to have the meanings as set forth below, except to the extent that the context in which they are used indicates otherwise. The following abbreviations and terms have the indicated meanings throughout:

| | |
|---|---|
| Ac = | acetyl |
| Boc = | t-butyloxy carbonyl |
| Bu = | butyl |
| c- = | cyclo |
| CBZ = | carbobenzoxy = benzyloxycarbonyl |
| DCM = | dichloromethane = methylene chloride = CH$_2$Cl$_2$ |
| DIEA = | N,N-diisopropylethylamine |
| DMF = | N,N-dimethylformamide |
| DMSO = | dimethyl sulfoxide |
| Et = | ethyl |
| HBTU = | O-benzotriazol-1-yl-N,N,N',N',-tetramethyluronium hexafluorophosphate |
| HMDS = | hexamethyldisilazane |
| HOAc = | acetic acid |
| IPA = | isopropyl alcohol |
| Me = | methyl |
| Ph = | phenyl |
| Py = | pyridine |
| rt = | room temperature |
| sat'd = | saturated |
| s- = | secondary |
| t- = | tertiary |
| TEA = | triethylamine |
| TFA = | trifluoroacetic acid |
| THF = | tetrahydrofuran |
| Tf = | triflate |

Alkyl is intended to include linear, branched, or cyclic aliphatic hydrocarbon structures and combinations thereof, which structures may be saturated or unsaturated. Lower-alkyl refers to alkyl groups of from 1 to 5 carbon atoms, preferably from 1 to 4 carbon atoms. Examples of lower-alkyl groups include methyl, ethyl, propyl, isopropyl, butyl, s- and t-butyl and the like. Preferred alkyl groups are those of $C_{20}$ or below. More preferred alkyl groups are those of $C_{13}$ or below. Cycloalkyl is a subset of alkyl and includes cyclic aliphatic hydrocarbon groups of from 3 to 13 carbon atoms. Examples of cycloalkyl groups include c-propyl, c-butyl, c-pentyl, norbornyl, adamantyl and the like. Cycloalkyl-alkyl- is another subset of alkyl and refers to cycloalkyl attached to the parent structure through a non-cyclic alkyl. Examples of cycloalkyl-alkyl- include cyclohexylmethyl, cyclopropylmethyl, cyclohexylpropyl, and the like. In this application, alkyl includes alkanyl, alkenyl and alkynyl residues; it is intended to include vinyl, allyl, isoprenyl and the like. Alkylene-, alkenylene-, and alkynylene- are other subsets of alkyl, including the same residues as alkyl, but having two points of attachment within a chemical structure. Examples of alkylene include ethylene (—$CH_2CH_2$—), propylene (—$CH_2CH_2CH_2$—), dimethyl-propylene (—$CH_2C(CH_3)_2CH_2$—) and cyclohexylpropylene (—$CH_2CH_2CH(C_6H_{13})$—). Likewise, examples of alkenylene include ethenylene (—CH=CH—), propenylene (—CH=CH —$CH_2$—), and cyclohexylpropenylene (—CH=CHCH($C_6H_{13}$)—). Examples of alkynylene include ethynylene (—C≡C—) and propynylene (—CH≡CH—$CH_2$—). When an alkyl residue having a specific number of carbons is named, all geometric isomers having that number of carbons are intended to be encompassed: thus, for example, "butyl" is meant to include n-butyl, sec-butyl, isobutyl and t-butyl; "propyl" includes n-propyl, isopropyl, and c-propyl.

Alkoxy or alkoxyl refers to an alkyl group, preferably including from 1 to 8 carbon atoms, of a straight, branched, or cyclic configuration, or a combination thereof, attached to the parent structure through an oxygen (i.e., the group alkyl-O—). Examples include methoxy-, ethoxy-, propoxy-, isopropoxy-, cyclopropyloxy-, cyclohexyloxy- and the like. Lower-alkoxy refers to alkoxy groups containing one to four carbons.

Acyl refers to groups of from 1 to 8 carbon atoms of a straight, branched, or cyclic configuration or a combination thereof, attached to the parent structure through a carbonyl functionality. Such groups may be saturated or unsaturated, and aliphatic or aromatic. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to acyl groups containing one to four carbons.

Amino refers to the group —$NH_2$. The term "substituted amino" refers to the group —NHR or —NRR where each R is independently selected from the group: optionally substituted alkyl, optionally substituted alkoxy, optionally substituted amino carbonyl, optionally substituted aryl, optionally substituted heteroaryl, optionally substituted heterocyclyl, acyl, alkoxycarbonyl, sulfanyl, sulfinyl and sulfonyl, e.g., diethylamino, methylsulfonylamino, furanyl-oxy-sulfonamino.

Aminocarbonyl- refers to the group —$NR^cCOR^b$, —$NR^cCO_2R^b$, or —$NR^cCONR^bR^c$, where $R_b$ is H or optionally substituted $C_1$-$C_6$ alkyl, aryl, heteroaryl, aryl-$C_1$-$C_4$ alkyl-, or heteroaryl-$C_1$-$C_4$ alkyl- group; and $R^c$ is hydrogen or $C_1$-$C_4$ alkyl; and where each optionally substituted $R^b$ group is independently unsubstituted or substituted with one or more substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halogen, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for heteroaryl), —$CO_2H$, —C(O)O$C_1$-$C_4$ alkyl, —CON($C_1$-$C_4$ alkyl)($C_1$-$C_4$ alkyl). —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2NH$($C_1$-$C_4$ alkyl), —$SO_2NH$(phenyl), —$NHSO_2$($C_1$-$C_4$ alkyl), —$NHSO_2$(phenyl), and —$NHSO_2$($C_1$-$C_4$ haloalkyl).

Antimitotic refers to a drug for inhibiting or preventing mitosis, for example, by causing metaphase arrest. Some antitumour drugs block proliferation and are considered antimitotics.

Aryl and heteroaryl mean a 5- or 6-membered aromatic or heteroaromatic ring containing 0 or 1-4 heteroatoms, respectively, selected from O, N, or S; a bicyclic 9- or 10-membered aromatic or heteroaromatic ring system containing 0 or 1-4 (or more) heteroatoms, respectively, selected from O, N, or S; or a tricyclic 12- to 14-membered aromatic or heteroaromatic ring system containing 0 or 1-4 (or more) heteroatoms, respectively, selected from O, N, or S. The aromatic 6- to 14-membered carbocyclic rings include, e.g., phenyl, naphthyl, indanyl, tetralinyl, and fluorenyl and the 5- to 10-membered aromatic heterocyclic rings include, e.g., imidazolyl, pyridinyl, indolyl, thienyl, benzopyranonyl, thiazolyl, furanyl, benzimidazolyl, quinolinyl, isoquinolinyl, quinoxalinyl, pyrimidinyl, pyrazinyl, tetrazolyl and pyrazolyl.

Aralkyl- refers to a residue in which an aryl moiety is attached to the parent structure via an alkyl residue. Examples include benzyl, phenethyl, phenylvinyl, phenylallyl and the like. Heteroaralkyl- refers to a residue in which a heteroaryl moiety is attached to the parent structure via an alkyl residue. Examples include furanylmethyl, pyridinylmethyl, pyrimidinylethyl and the like.

Aralkoxy- refers to the group —O-aralkyl. Similarly, heteroaralkoxy- refers to the group —O-heteroaralkyl; aryloxy- refers to the group —O-aryl; acyloxy- refers to the group —O-acyl; heteroaryloxy- refers to the group —O-heteroaryl; and heterocyclyloxy- refers to the group —O-heterocyclyl (i.e., aralkyl, heteroaralkyl, aryl, acyl, heterocyclyl, or heteroaryl is attached to the parent structure through an oxygen).

Carboxyalkyl- refers to the group -alkyl-COOH.

Carboxamido refers to the group —$CONR^bR^c$, where $R^b$ is H or optionally substituted $C_1$-$C_6$ alkyl, aryl, heteroaryl, aryl-$C_1$-$C_4$ alkyl-, or heteroaryl-$C_1$-$C_4$ alkyl- group; and $R^c$ is hydrogen or $C_1$-$C_4$ alkyl; and where each optionally substituted $R^b$ group is independently unsubstituted or substituted with one or more substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halogen, —OH, —$NH_2$, —$C_1$-$C_4$ alkyl-$NH_2$, —N($C_1$-$C_4$ alkyl)($C_1$-$C_4$ alkyl), —NH ($C_1$-$C_4$ alkyl), —N($C_1$-$C_4$ alkyl)($C_1$-$C_4$ alkylphenyl), —NH ($C_1$-$C_4$ alkylphenyl), cyano, nitro, oxo (as a substituent for heteroaryl), —$CO_2H$, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH(phenyl), —$NHSO_2$($C_1$-$C_4$ alkyl), —$NHSO_2$(phenyl), and —$NHSO_2$($C_1$-$C_4$ haloalkyl).

Halogen or halo refers to fluorine, chlorine, bromine or iodine. Fluorine, chlorine and bromine are preferred. Dihaloaryl, dihaloalkyl, trihaloaryl etc. refer to aryl and alkyl substituted with the designated plurality of halogens (here, 2, 2 and 3, respectively), but not necessarily a plurality of the same halogen; thus 4-chloro-3-fluorophenyl is within the scope of dihaloaryl.

Heterocyclyl means a cycloalkyl or aryl residue in which one to four of the carbons is replaced by a heteroatom such as oxygen, nitrogen or sulfur. Examples of heterocycles that fall within the scope of the invention include azetidinyl, imidazolinyl, pyrrolidinyl, pyrazolyl, pyrrolyl, indolyl, quinolinyl, isoquinolinyl, tetrahydroisoquinolinyl, benzofuranyl, benzodioxanyl, benzodioxyl (commonly referred to as methylenedioxyphenyl, when occurring as a substituent), tetrazolyl, morpholinyl, thiazolyl, pyridinyl, pyridazinyl, piperidinyl, pyrimidinyl, thienyl, furanyl, oxazolyl, oxazolinyl, isoxazolyl, dioxanyl, tetrahydrofuranyl and the like. "N-heterocyclyl" refers to a nitrogen-containing heterocycle. The term heterocyclyl encompasses heteroaryl, which is a subset of heterocyclyl. Examples of N-heterocyclyl residues include azetidinyl, 4-morpholinyl, 4-thiomorpholinyl, 1-piperidinyl, 1-pyrrolidinyl, 3-thiazolidinyl, piperazinyl and 4-(3,4-dihydrobenzoxazinyl). Examples of substituted heterocyclyl include 4-methyl-1-piperazinyl and 4-benzyl-1-piperidinyl.

A leaving group or atom is any group or atom that will, under the reaction conditions, cleave from the starting material, thus promoting reaction at a specified site. Suitable examples of such groups unless otherwise specified are halogen atoms, mesyloxy, p-nitrobenzensulphonyloxy and tosyloxy groups.

Optional or optionally means that the subsequently described event or circumstance may or may not occur, and that the description includes instances where said event or circumstances occurs and instances in which it does not. For example. "optionally substituted alkyl" includes "alkyl"and "substituted alkyl" as defined herein. It will be understood by those skilled in the art with respect to any group containing one or more substituents that such groups are not intended to introduce any substitution or substitution patterns that are sterically impractical and/or synthetically non-feasible and/or inherently unstable.

Substituted alkoxy refers to alkoxy wherein the alkyl constituent is substituted (i.e., —O-(Substituted alkyl)). One preferred substituted alkoxy group is "polyalkoxy" or —O-(optionally substituted alkylene)-(optionally substituted alkoxy), and includes groups such as —$OCH_2CH_2OCH_3$, and residues of glycol ethers such as polyethyleneglycol, and —O$(CH)_2CH_2O)CH_3$, where x is an integer of about 2-20, preferably about 2-10, and more preferably about 2-5. Another preferred substituted alkoxy group is hydroxyalkoxy or —$OCH_2$($CH_2$)$_y$OH, where y is an integer of about 1-10, preferably about 1-4.

Substituted- alkyl, aryl, and heteroaryl, which includes the substituted alkyl, aryl and heteroaryl moieties of any group containing an optionally substituted alkyl, aryl and heteroaryl moiety (e.g. alkoxy, aralkyl and heteroaralkyl), refer respectively to alkyl, aryl, and heteroaryl wherein one or more (up to about 5, preferably up to about 3) hydrogen atoms are replaced by a substituent independently selected from the group:

—$R^a$, —$OR^b$, —O($C_1$-$C_2$ alkyl)O— (as an aryl substituent), —$SR^b$, —$NR^bR^c$, halogen, cyano, nitro, —$COR^b$, —$CO_2R^b$, —$CONR^bR^c$, —$OCOR^b$, —$OCO_2R^b$, —$OCONR^bR^c$, —$NR^cCOR^b$, —$NR^cCO_2R^b$, —$NR^cCONR^bR^c$, —$CO_2R^b$, —$CONR^bR^c$, —$NR^cCOR^b$, —$SOR^a$, —$SO_2R^a$, —$SO_2NR^bR^c$, and —$NR^cSO_2R^a$, where $R^a$ is an optionally substituted $C_1$-$C_6$ alkyl, aryl, heteroaryl, aryl-$C_1$-$C_4$ alkyl-, or heteroaryl-$C_1$-$C_4$ alkyl- group, $R^b$ is H or optionally substituted $C_1$-$C_6$ alkyl, aryl, heteroaryl, aryl-$C_1$-$C_4$ alkyl-, or heteroaryl-$C_1$-$C_4$ alkyl- group;

$R^c$ is hydrogen or $C_1$-$C_4$ alkyl;

where each optionally substituted $R^a$ group and $R^b$ group is independently unsubstituted or substituted with one or more substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —O$C_1$-$C_4$ alkyl, —O$C_1$-$C_4$ alkylphenyl, —$C_1$-$C_4$ alkyl-OH, —O$C_1$-$C_4$ haloalkyl, halogen, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for heteroaryl), —$CO_2$H, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH(phenyl), —$NHSO_2$($C_1$-$C_4$ alkyl), —$NHSO_2$(phenyl), and —$NHSO_2$($C_1$-$C_4$ haloalkyl).

Sulfanyl refers to the groups: —S-(optionally substituted alkyl). —S-(optionally substituted aryl), —S-(optionally substituted heteroaryl), and —S-(optionally substituted heterocyclyl).

Sulfinyl refers to the groups: —S(O)—H, —S(O)-(optionally substituted alkyl), —S(O)-optionally substituted aryl), —S(O)-(optionally substituted heteroaryl), —S(O)-(optionally substituted heterocyclyl); and —S(O)-(optionally substituted amino).

Sulfonyl refers to the groups: —S($O_2$)—H, —S($O_2$)-(optionally substituted alkyl), —S($O_2$)-optionally substituted aryl), —S($O_2$)-(optionally substituted heteroaryl), —S($O_2$)-(optionally substituted heterocyclyl), —S($O_2$)-(optionally substituted alkoxy), —S($O_2$)-optionally substituted aryloxy), —S($O_2$)-(optionally substituted heteroaryloxy), —S($O_2$)-(optionally substituted heterocyclyloxy); and —S($O_2$)-(optionally substituted amino).

Pharmaceutically acceptable salts refers to those salts that retain the biological effectiveness of the free compound and that are not biologically or otherwise undesirable, formed with a suitable acid or base, and includes pharmaceutically acceptable acid addition salts and base addition salts. Pharmaceutically acceptable acid addition salts include those derived from inorganic acids such as hydrochloric acid, hydrobromic acid, sulfuric acid, nitric acid, phosphoric acid and the like, and those derived from organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

Pharmaceutically acceptable base addition salts include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Base additioin salts also include those derived from pharmaceutically acceptable organic non-toxic bases, including salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

Protecting group has the meaning conventionally associated with it in organic synthesis, i.e. a group that selectively blocks one or more reactive sites in a multifunctional compound such that a chemical reaction can be carried out selectively on another unprotected reactive site and such that the group can readily be removed after the selective reaction is complete. A variety of protecting groups are disclosed, for example, in T. H. Greene and P. G. M. Wuts. Protective Groups in Organic Synthesis, Third Edition, John Wiley & Sons, New York (1999), which is incorporated herein by reference in its entirety. For example, a hydroxy protected form is where at least one of the hydroxyl groups present in a compound is protected with a hydroxy protecting group. Likewise, amines and other reactive groups may similarly be protected.

Solvate refers to the compound formed by the interaction of a solvent and a compound of Formula I or salt thereof. Suitable solvates of the compounds of the Formula I are pharmaceutically acceptable solvates, such as hydrates, including monohydrates and hemi-hydrates.

Many of the compounds described herein contain one or more asymmetric centers (e.g. the carbon to which $R_2$ and $R_{2'}$ are attached where $R_2$ differs from $R_{2'}$) and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms and rotational isomers are also intended to be included.

When desired, the R- and S-isomers may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where the desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents, or by converting one enantiomer to the other by asymmetric transformation.

Compounds of the Present Invention

The present invention is directed to a class of novel compounds, which can be described as benzopyran-4-ones or chromen-4-ones, that are inhibitors of one or more mitotic kinesins. By inhibiting mitotic kinesins, but not other kinesins (e.g., transport kinesins), specific inhibition of cellular proliferation is accomplished. While not intending to be bound by any theory, the present invention capitalizes on the finding (that perturbation of mitotic kinesin function causes malformation or dysfunction of mitotic spindles, frequently resulting in cell cycle arrest and cell death. According to one embodiment of the invention, the compounds described herein inhibit the mitotic kinesin, KSP. In another embodiment, the compounds inhibit the mitotic kinesin, KSP, as well as modulating one or more of the human mitotic kinesins selected from the group consisting of HSET (see, U.S. Pat. No. 6,361,993, which is incorporated herein by reference); MCAK (see, U.S. Pat. No. 6,331,424, which is incorporated herein by reference); CENP-E (see, PCT Publication No. WO 99/13061, which is incorporated herein by reference); Kif4 (see, U.S. Pat. No. 6,440,684, which is incorporated herein by reference); MKLP1 (see, U.S. Pat. No. 6,448,025, which is incorporated herein by reference); Kif15 (see, U.S. Pat. No. 6,355,466, which is incorporated herein by reference); Kid (see, U.S. Pat. No. 6,387,644, which is incorporated herein by reference); Mpp1, CMKrp, Kin1-3 (see, U.S. Pat. No. 6,461,855, which is incorporated herein by reference); Kip3a (see, PCT Publication No. WO 01/96593, which is incorporated herein by reference); Kip3d (see, U.S. Pat. No. 6,492,151, which is incorporated herein by reference); and RabK6.

The methods of inhibiting a human KSP kinesin comprise contacting an inhibitor of the invention with a kinesin, particularly a human kinesin, preferably human KSP or fragments and variants thereof. The inhibition can be of the ATP hydrolysis activity of the KSP kinesin and/or the mitotic spindle formation activity, such that the mitotic spindles are disrupted. Meiotic spindles may also be disrupted.

An object of the present invention is to develop inhibitors of mitotic kinesins, in particular KSP and especially human KSP, for the treatment of disorders associated with cell proliferation. Traditionally, dramatic improvements in the treatment of cancer, one type of cellular proliferative disorder, have been associated with identification of therapeutic agents acting through novel mechanisms. Examples of this include not only the taxane class of agents that appear to act on microtubule formation, but also the camptothecin class of topoisomerase I inhibitors. The compounds, compositions and methods described herein can differ in their selectivity and are preferably used to treat diseases of cellular proliferation, including, but not limited to cancer, hyperplasias, restenosis, cardiac hypertrophy, immune disorders, fungal disorders and inflammation.

Accordingly, the present invention relates to methods employing compounds represented by Formula I:

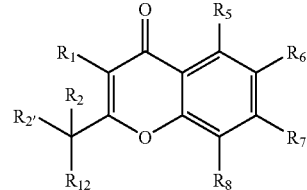

Formula I wherein:

$R_1$ is chosen from hydrogen, optionally substituted alkyl-, optionally substituted aryl-, optionally substituted aralkyl-, optionally substituted heteroaryl-, and optionally substituted heteroaralkyl-;

$R_2$ and $R_{2'}$ are independently chosen from hydrogen, optionally substituted alkyl-, optionally substituted alkoxy, optionally substituted aryl-, optionally substituted aralkyl-, optionally substituted heteroaryl-, and optionally substituted heteroaralkyl-; or $R_2$ and $R_{2'}$ taken together form an optionally substituted 3- to 7-membered ring;

$R_{12}$ is selected from the group consisting of optionally substituted imidazolyl, optionally substituted imidazolinyl, —$NHR_4$; —$N(R_4)(COR_3)$; —$N(R_4)(SO_2R_{3a})$; and —$N(R_4)(CH_2R_{3b})$;

$R_3$ is chosen from hydrogen, optionally substituted alkyl-, optionally substituted aryl-, optionally substituted aralkyl-, optionally substituted heteroaryl-, optionally substituted heteroaralkyl-, $RH_{15}O$— and $R_{17}$—NH—;

$R_{3a}$ is chosen from optionally substituted alkyl-, optionally substituted aryl-, optionally substituted aralkyl-, optionally substituted heteroaryl-, optionally substituted heteroaralkyl-, and $R_{17}$—NH—;

$R_{3b}$ is chosen from hydrogen, optionally substituted alkyl-, optionally substituted aryl-, optionally substituted aralkyl-, optionally substituted heteroaryl-, and optionally substituted heteroaralkyl-;

$R_4$ is chosen from hydrogen, optionally substituted alkyl-, optionally substituted aryl-, optionally substituted aralkyl-, optionally substituted hetercyclyl-, and optionally substituted heteroaralkyl-;

$R_5$, $R_6$, $R_7$ and $R_8$ are independently chosen from hydrogen, acyl, optionally substituted alkyl-, optionally substituted alkoxy, halogen, hydroxyl, nitro, cyano, dialkylamino, alkylsulfonyl-, alkylsulfonamido-, alkylthio-, carboxyalkyl-, carboxamido-, aminocarbonyl-, optionally substituted aryl and optionally substituted heteroaryl-;

$R_{15}$ is chosen from optionally substituted alkyl-, optionally substituted aryl-, optionally substituted aralkyl-, optionally substituted heteroaryl-, and optionally substituted heteroaralkyl-, and $R_{17}$ is hydrogen, optionally substituted alkyl-, optionally substituted aryl-, optionally substituted aralkyl-, optionally substituted heteroaryl-, or optionally substituted heteroaralkyl-, including single stereoisomers, mixtures of stereoisomers;

a pharmaceutically acceptable salt of a compound of Formula I;

a pharmaceutically acceptable solvate of a pharmaceutically acceptable solvate of a compound of Formula I;

or a pharmaceutically acceptable solvate of a pharmaceutically acceptable salt of a compound of Formula I.

When $R_{12}$ is an imidazole, $R_{12}$ has the formula:

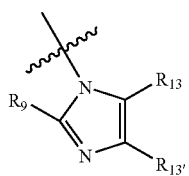

wherein $R_9$ is chosen from hydrogen, optionally substituted $C_1$-$C_8$ alkyl, optionally substituted aryl, optionally substituted aryl-$C_1$-$C_4$-alkyl-, optionally substituted heteroaryl-$C_1$-$C_4$-alkyl-, optionally substituted aryl-$C_1$-$C_4$-alkoxy-, optionally substituted heteroaryl-$C_1$-$C_4$-alkoxy-, optionally substituted heteroaryl-; and $R_{13}$ and $R_{13'}$ are independently hydrogen, optionally substituted $C_1$-$C_8$ alkyl, optionally substituted aryl, or optionally substituted aryl-$C_1$-$C_4$-alkyl-.

When $R_{12}$ is an imidazoline, $R_{12}$ has the formula

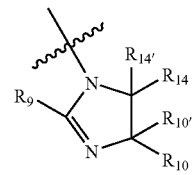

wherein $R_9$ is chosen from hydrogen, optionally substituted $C_1$-$C_8$ alkyl-, optionally substituted aryl, optionally substituted aryl-$C_1$-$C_4$-alkyl-, and optionally substituted heteroaryl-; and $R_{10}$, $R_{10'}$, $R_{14}$, and $R_{14'}$ are independently chosen from hydrogen, optionally substituted $C_1$-$C_8$ alkyl, optionally substituted aryl, and optionally substituted aryl-$C_1$-$C_4$-alkyl-.

In one embodiment, $R_1$ is chosen from hydrogen, optionally substituted alkyl, optionally substituted aryl, optionally substituted aralkyl, optionally substituted heteroaryl, and optionally substituted heteroaralkyl-;

$R_2$ and $R_{2'}$ are independently chosen from hydrogen, optionally substituted alkyl, optionally substituted alkoxy, optionally substituted aryl, optionally substituted aralkyl, optionally substituted heteroaryl, and optionally substituted heteroaralkyl-; or $R_2$ and $R_{2'}$ taken together form an optionally substituted 3- to 7-membered ring, provided that if either $R_2$ or $R_{2'}$ hydrogen, then the other is not hydrogen;

$R_{12}$ is selected from the group consisting of optionally substituted imidazolyl, optionally substituted imidazolinyl, —$NHR_4$; —$N(R_4)(COR_3)$; —$N(R_4)(SO_2R_{3a})$; and —$N(R_4)(CH_2R_{3b})$;

$R_3$ is chosen from hydrogen, optionally substituted alkyl, optionally substituted aryl, optionally substituted aralkyl, optionally substituted heteroaryl, optionally substituted heteroaralkyl, $R_{15}O$— and $R_{17}$—NH—;

$R_{3a}$ is chosen from optionally substituted alkyl, optionally substituted aryl, optionally substituted aralkyl, optionally substituted heteroaryl, optionally, substituted heteroaralkyl, and $R_{17}$—NH—;

$R_{3b}$ is chosen from hydrogen, optionally substituted alkyl, optionally substituted aryl, optionally substituted aralkyl, optionally substituted heteroaryl, and optionally substituted heteroaralkyl;

$R_4$ is chosen from hydrogen, optionally substituted alkyl-, optionally substituted aryl-, optionally substituted aralkyl-, optionally substituted hetercyclyl-, and optionally substituted heteroaralkyl-;

$R_5$, $R_6$, $R_7$ and $R_8$ are independently chosen from hydrogen, acyl, optionally substituted alkyl, optionally substituted alkoxy, halogen, hydroxyl, nitro, cyano, dialkylamino, alkylsulfonyl, alkylsulfonamido, alkylthio, carboxyalkyl, carboxamido, aminocarbonyl, optionally substituted aryl and optionally substituted heteroaryl-;

$R_{15}$ is chosen from optionally substituted alkyl, optionally substituted aryl, optionally substituted aralkyl, optionally substituted lheteroaryl, and optionally substituted heteroaralkyl-; and $R_{17}$, is chosen from hydrogen, optionally substituted alkyl, optionally substituted aryl, optionally substituted aralkyl, optionally substituted heteroaryl, and optionally substituted heteroaralkyl, including single stereoisomers, mixtures of stereoisomers;

a pharmaceutically acceptable salt of a compound of Formula I;

a pharmaceutically acceptable solvate of a pharmaceutically acceptable solvate of a compound of Formula I; or a pharmaceutically acceptable solvate of a pharmaceutically acceptable salt of a compound of Formula I.

In another embodiment, $R_2$ and $R_{2'}$ are hydrogen; and $R_1$ is chosen from optionally substituted aryl, optionally substituted aralkyl, optionally substituted heteroaryl, and optionally substituted heteroaralkyl, provided however, that $R_1$ is not substituted phenyl;

$R_{12}$ is selected from the group consisting of optionally substituted imidazolyl, optionally substituted imidazolinyl, —$NHR_4$; —$N(R_4)(COR_3)$—$N(R_4)(SO_2R_{3a})$; and —$N(R_4)(CH_2R_{3b})$;

$R_3$ is chosen from hydrogen, optionally substituted alkyl, optionally substituted aryl, optionally substituted aralkyl, optionally substituted heteroaryl, optionally substituted heteroaralkyl, $R_{15}O$— and $R_{17}$—NH—;

$R_{3a}$ is chosen from optionally substituted alkyl, optionally substituted aryl optionally substituted aralkyl, optionally substituted heteroaryl, optionally substituted heteroaralkyl, and $R_{17}$—NH—;

$R_{3b}$ is chosen from hydrogen, optionally substituted alkyl, optionally substituted aryl, optionally substituted aralkyl, optionally substituted heteroaryl, and optionally substituted heteroaralkyl-;

$R_4$ is chosen from hydrogen, optionally substituted alkyl-, optionally substituted aryl-, optionally substituted aralkyl-, optionally substituted hetercyclyl-, and optionally substituted heteroaralkyl-;

$R_5$, $R_6$, $R_7$ and $R_8$ are independently chosen from hydrogen, acyl, optionally substituted alkyl, optionally substituted alkoxy, halogen, hydroxyl, nitro, cyano, dialkylamino, alkylsulfonyl, alkylsulfonamido, alkylthio, carboxyalkyl, carboxamido, aminocarbonyl, optionally substituted aryl and optionally substituted heteroaryl-;

$R_{15}$ is chosen from optionally substituted alkyl, optionally substituted aryl, optionally substituted aralkyl, optionally substituted heteroaryl, and optionally substituted heteroaralkyl-; and $R_{17}$ is chosen from hydrogen, optionally substituted alkyl, optionally substituted aryl, optionally substituted aralkyl, optionally substituted heteroaryl, and optionally substituted heteroaralkyl, including single stereoisomers, mixtures of stereoisomers;

a pharmaceutically acceptable salt of a compound of Formula I;

a pharmaceutically acceptable solvate of a pharmaceutically acceptable solvate of a compound of Formula I; or a pharmaceutically acceptable solvate of a pharmaceutically acceptable salt of a compound of Formula I.

In a particularly preferred embodiment, where $R_2$ differs from $R_{2'}$, the stereogenic center to which $R_2$ and $R_{2'}$ are attached is of the R configuration.

Nomenclature

The compounds of Formula I can be named and numbered in the manner (e.g., using AutoNom version 2.1 or ISIS-DRAW, each of which utilizes the IUPAC system of nomenclature) described below. For example, the compound:

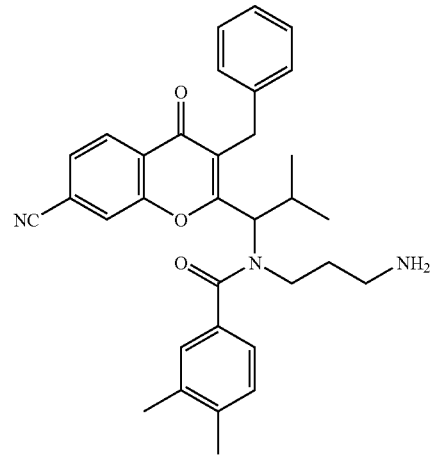

i.e., the compound according to Formula I where $R_1$ is benzyl, $R_2$ is propyl (particularly i-propyl), $R_{2'}$ is hydrogen; $R_{12}$ is —$N(R_4)(COR_3)$; $R_3$ is 3,4-dimethylphenyl-; $R_4$ is 3-aminopropyl-; $R_5$, $R_6$, and $R_8$ are hydrogen; and $R_7$ is cyano is named N-(3-amino-propyl)-N-[1-(3-benzyl-7-cyano-4-oxo-4H-chromen-2-yl)-2-methyl-propyl]-3,4-dimethyl-benzamide.

Likewise, the compound:

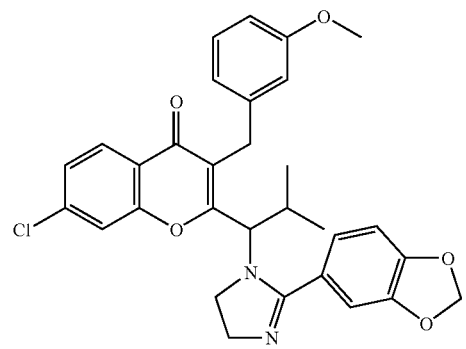

i.e., the compound according to Formula I where $R_1$ is 3-methoxy-benzyl. $R_2$ is propyl (particularly i-propyl), $R_{2'}$ is hydrogen; $R_{12}$ is substituted imidazoline; $R_5$, $R_6$, and $R_8$ are hydrogen; $R_7$ is chloro; $R_9$ is methylenedioxyphenyl-; $R_{10}$, $R_{10'}$, $R_{14}$, and $R_{14'}$ are hydrogen can be named 2-[1-(2-benzo[1,3]dioxol-5-yl-4,5-dihydro-imidazol-1-yl)-2-methyl-propyl]-7-chloro-3-(3-methoxy-benzyl)-chromen-4-one.

Synthesis of the Compounds of Formula I

The compounds of Formula I can be prepared by following the procedures described with reference to the Reaction Schemes below or utilizing techniques well known in the art. See, for example, Hirao et al. (1984) Synthesis 1076-1078 and Coppola et al. (1981) Synthesis 523-526, which are incorporated herein by reference.

Unless specified otherwise, the terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents.

The term "q.s." means adding a quantity sufficient to achieve a stated function, e.g., to bring a solution to the desired volume (i.e. 100%).

In general, esters of carboxylic acids may be prepared by conventional esterification procedures, for example alkyl esters may be prepared by treating the required carboxylic acid with the appropriate alkanol, generally under acidic conditions. Likewise, amides may be prepared using conventional amidation procedures, for example amides may be prepared by treating the relevant carboxylic acid with the appropriate amine. Alternatively, a lower-alkyl ester such as a methyl ester of the acid may be treated with an amine to provide the required amide, optionally in presence of trimethylalluminium following the procedure described in Tetrahedron Lett. 48, 4171-4173, (1977 Carboxyl groups may be protected as alkyl esters, for example methyl esters, which esters may be prepared and removed using conventional procedures, one convenient method for converting carbomethoxy to carboxyl is to use aqueous lithium hydroxide.

The salts and solvates of the compounds mentioned herein may as required be produced by methods conventional in the art. For example, if an inventive compound is an acid, a desired base addition salt can be prepared by treatment of the free acid with an inorganic or organic base, such as an amine (primary, secondary, or tertiary); an alkali metal or alkaline earth metal hydroxide; or the like. Illustrative examples of suitable salts include organic salts derived from amino acids such as glycine and arginine; ammonia; primary, secondary, and tertiary amines; such as ethylenediamine, and cyclic amines, such as cyclohexylamine, piperidine, morpholine, and piperazine as well as inorganic salts derived from sodium, calcium, potassium, magnesium, manganese, iron, copper, zinc, aluminum, and lithium.

If a compound is a base, a desired acid addition salt may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, maleic acid, succinic acid, mandelic acid, fumaric acid, malonic acid, pyruvic acid, oxalic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid, methanesulfonic acid, ethanesulfonic acid, or the like.

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can, of course, also be used.

Brief Description of Reaction Schemes

Reaction Scheme 1 illustrates a synthesis of compounds of formula 109, an intermediate in the synthesis of compounds of Formula I.

Reaction Scheme 2 illustrates a synthesis of compounds of Formula I wherein $R_{12}$ is —N($R_4$)(COR$_3$).

Reaction Scheme 3 illustrates a synthesis of compounds of Formula I wherein $R_7$ is —OH.

Reaction Scheme 4 illustrates a synthesis of compounds of Formula I wherein $R_7$ is —OCH$_3$.

Reaction Scheme 5 illustrates another synthesis of compounds of Formula I wherein $R_{12}$ is —N($R_4$)(COR$_3$).

Reaction Scheme 6 illustrates a synthesis of compounds of Formula I wherein $R_{12}$ is —N($R_4$)(SO$_2$$R_{3a}$).

Reaction Scheme 7 illustrates a synthesis of compounds of Formula I wherein $R_{12}$ is —N($R_4$)(CH$_2$$R_{3b}$).

Reaction Scheme 8 illustrates a synthesis of compounds of Formula I wherein $R_{12}$ is optionally substituted imidazolyl.

Reaction Scheme 9 illustrates another synthesis of compounds of Formula I wherein $R_{12}$ is optionally substituted imidazolinyl.

Reaction Scheme 10 illustrates a synthesis of compounds of Formula I wherein $R_{12}$ is optionally substituted imidazolinyl.

Reaction Scheme 11 illustrates a second synthesis of compounds of Formula I wherein $R_{12}$ is optionally substituted imidazolinyl.

Reaction Scheme 12 illustrates a synthesis of compounds of Formula I wherein $R_{12}$ is —N($R_4$)(COR$_3$) wherein $R_3$, is —OR$_{15}$.

Reaction Scheme 13 illustrates a synthesis of compounds of Formula I wherein $R_{12}$ is —N($R_4$)(COR$_3$) wherein $R_3$ is —NHR$_{17}$.

Reaction Scheme 14 illustrates a synthesis of compounds of Formula 1407 which can be used as an intermediate in the synthesis of compounds of Formula I.

Reaction Scheme 15 illustrates a synthesis of compounds of Formula 1505 which can be used as an intermediate in the synthesis of compounds of Formula I.

Starting Materials

The optionally substituted compounds of Formula 101 are commercially available, e.g., from Aldrich Chemical Company, Milwaukee, Wis. Other reactants are likewise commercially available or may be readily prepared by those skilled in the art using commonly employed synthetic methodology.

Reaction Scheme 1

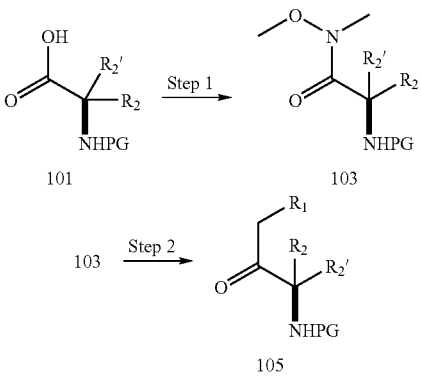

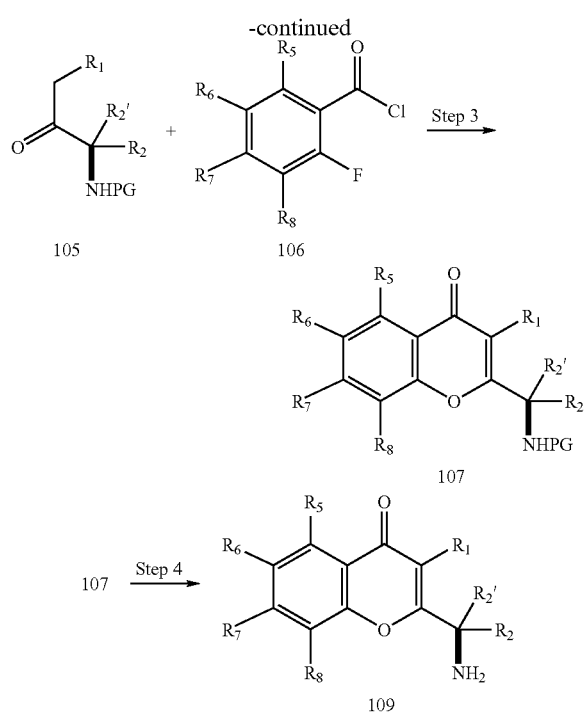

Preparation of Compounds of Formula 103

Referring to Reaction Scheme 1, Step 1, about an equivalent of ethyl chloroformate is added over about one minute to a 0-5° C. solution of a compound of Formula 101 (preferably wherein the amino protecting group, PG, is a Boc group) and a base such as triethylamine in a nonpolar, aprotic solvent such as THF. After about 15 minutes, a mixture of an excess of dimethylhydroxylamine hydrochloride (preferably about 1.2 equivalents) and a base such as triethylamine in a nonpolar, aprotic solvent such as THF is added over about 5 minutes. The product, a compound of Formula 103, is isolated and used without further purification.

Preparation of Compounds of Formula 105

Referring to Reaction Scheme 1, Step 2, a Grignard reagent is prepared by mixing a compound of formula $R_1CH_2Br$ (generally about 3 equivalents) and magnesium turnings in a nonpolar, aprotic solvent such as diethyl ether. After about 1.5 hours, the Grignard reaction is generally complete. A solution of a compound of Formula 103 in a nonpolar, aprotic solvent such as ether, is added to the Grignard reagent. The temperature should be monitored and not allowed to exceed ~30° C. The product a compound of Formula 105, is isolated and purified.

Preparation of Compounds of Formula 107

Referring to Reaction Scheme 1, Step 3, lithium bis(trimethylsilyl)amide (about 3.3 equivalents) is added slowly over ~3 minutes to a −78° C. solution of a compound of Formula 105 in a nonpolar, aprotic solvent such as THF. The reaction solution temperature should be monitored and the addition of base conducted at a rate sufficient to prevent the temperature from exceeding about −54° C. After the addition is complete, the resulting solution is maintained at −78° C. for about 30 minutes. An acid chloride of Formula 106 (preferably, neat) is then added. The reaction solution is maintained at −78° C. for about 30 minutes. The product is isolated and used without further purification.

A mixture of the above crude product, a base such as potassium carbonate, and a polar, aprotic solvent such as DMF is maintained at about room temperature for about 30 minutes. The product, a compound of Formula 107 is isolated and purified.

Preparation of Compounds of Formula 109

Referring to Reaction Scheme 1, Step 4, optionally, the protecting group. PG, may be removed from the amine. One of skill in the art will appreciate that the conditions for removal of the protecting group will vary with different protecting groups. Such conditions are well known in the art and can be found, e.g., in Greene et al. supra. When PG is Boc, it may be removed by treatment of a compound of Formula 107 with a mixture of aqueous TFA (preferably TFA:$H_2O$, 97.5: 2.5) at room temperature. The product, a compound of Formula 109, is isolated and purified.

Preparation of Optically Active Compounds

In compounds of the invention where $R_2$ differs from $R_{2'}$, a particular stereo configuration (such as the (R) isomer) may be preferred at the stereogenic center to which $R_2$ and $R_{2'}$ are attached. The optically active compound can be prepared by methods known in the art. For example, an amine of Formula 109 is dissolved in an inert organic solvent (such as IPA) and warmed to 60° C. In a separate vessel, a resolving agent (such as dibenzoyl-D-tartaric acid) is dissolved, preferably in the same warm solvent, and then quickly added (with agitation) to the warm amine solution. The reaction mixture is left to crystallize by cooling to room temperature over 16 hours under continuing, agitation. The desired isomer, e.g., the (R) isomer of a compound of Formula 109, is isolated and purified.

For the sake of brevity in the remaining description of the synthesis of compounds of Formula I, it should be understood that either single isomer or a mixture of isomers may be employed to give the corresponding product.

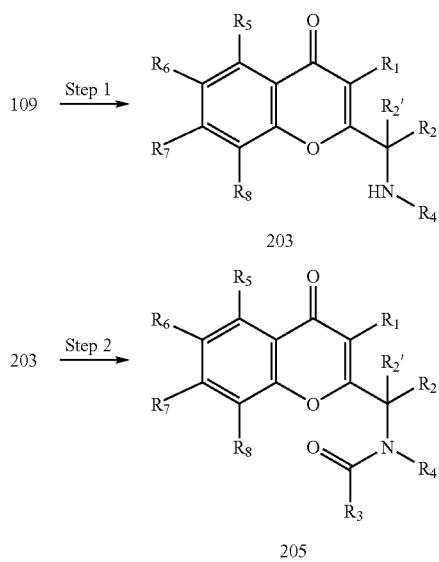

Reaction Scheme 2

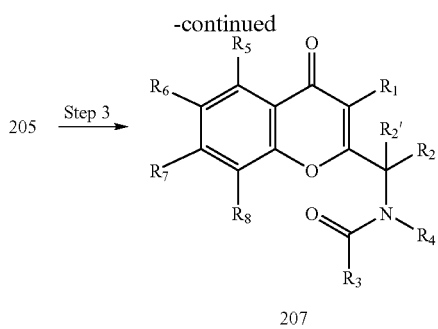

207

Preparation of Formula 203

Referring, to Reaction Scheme 2, Step 1, to a solution of a compound of Formula 109 is added successively a slight excess (preferably about 1.2 equivalents) of an aldehyde comprising $R_{4'}$ (i.e., a compound having the formula $R_{4'}CHO$ where $R_{4'}CH_2$— is equivalent to $R_4$ and $R_4$ is as described above or is a protected precursor to such a substituent, e.g., (3-oxo-propyl)-carbamic acid tert-butyl ester) and a reducing agent such as sodium triacetoxyborohydride. The resulting mixture is stirred for several hours. The product, a compound of Formula 203 is isolated and purified.

Preparation of Formula 205

Referring to Reaction Scheme 2, Step 2, to a solution of a compound of Formula 203 and an amine base such as diisopropylethylamine in a nonpolar, aprotic solvent such as dichloromethane is added an $R_3$ acyl chloride (such as Cl—C(O)—$R_3$ where $R_3$ is as described above). The resulting solution is stirred under nitrogen at room temperature for several hours. The product, a compound of Formula 205 is isolated and purified.

Preparation of Formula 207

Optionally, any protecting groups oil compounds of Formula 205 are then removed. For example, if $R_4$ comprises a protected amine wherein the protecting group is a Boc group, the Boc group can be removed by treatment of the compound of Formula 205 with an acid such as trifluoroacetic acid in a nonpolar, aprotic solvent such as dichloromethane, while maintaining the reaction at about room temperature. The reaction is monitored e.g., by TLC. Upon completion, the product, a compound of Formula 207 is isolated and purified.

Reaction Scheme 3

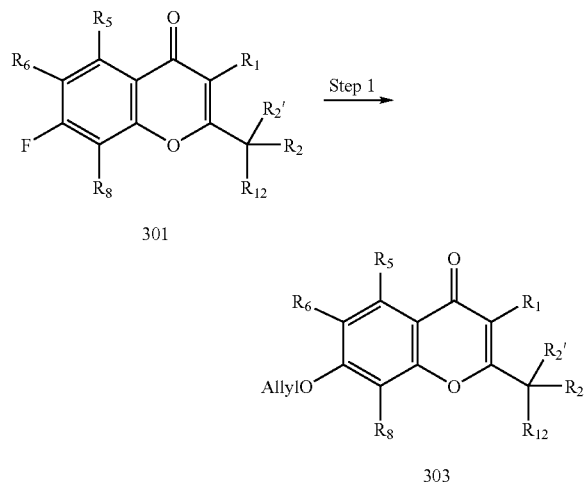

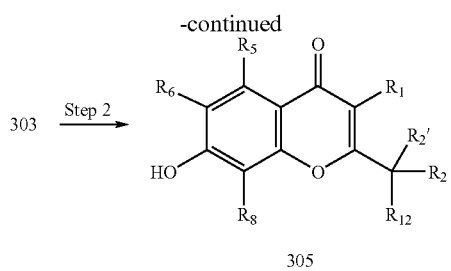

305

Preparation of Compounds of Formula 303

Referring to Reaction Scheme 3, Step 1, to a solution of a compound of Formula 301 in a nonpolar, aprotic solvent such as DMF is added sodium hydride. The resulting solution was stirred at about 45° C. for about 5 minutes, then allyl alcohol (about 14 equivalents) is added via pipette. The resulting solution is stirred at about 45° C. for about 12 hours and then cooled to room temperature. The product, a compound of Formula 303, is isolated and used without further purification.

Preparation of Compounds of Formula 305

Referring to Reaction Scheme 3, Step 2, to a room temperature solution of a compound of Formula 303, in an aprotic solvent such as acetonitrile, is added morpholine followed by $Pd(PPh_3)_4$. The resulting solution is stirred for about 5 minutes. The product, a compound of Formula 305, is isolated and purified.

Reaction Scheme 4

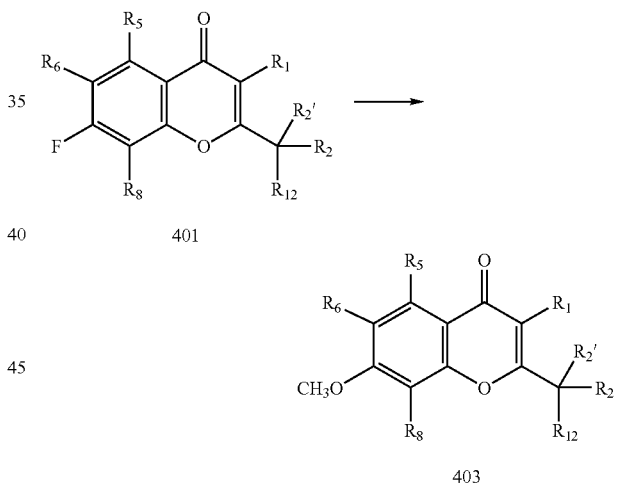

Referring to Reaction Scheme 4, a compound of Formula 401 is dissolved in 0.5 M solution methoxide in methanol and heated to about 70° C. The temperature is maintained at about 70° C. for about 12 hours and then cooled to room temperature. The product, a compound of Formula 403, is isolated and purified.

Reaction Scheme 5

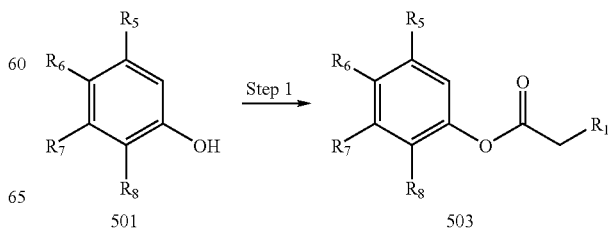

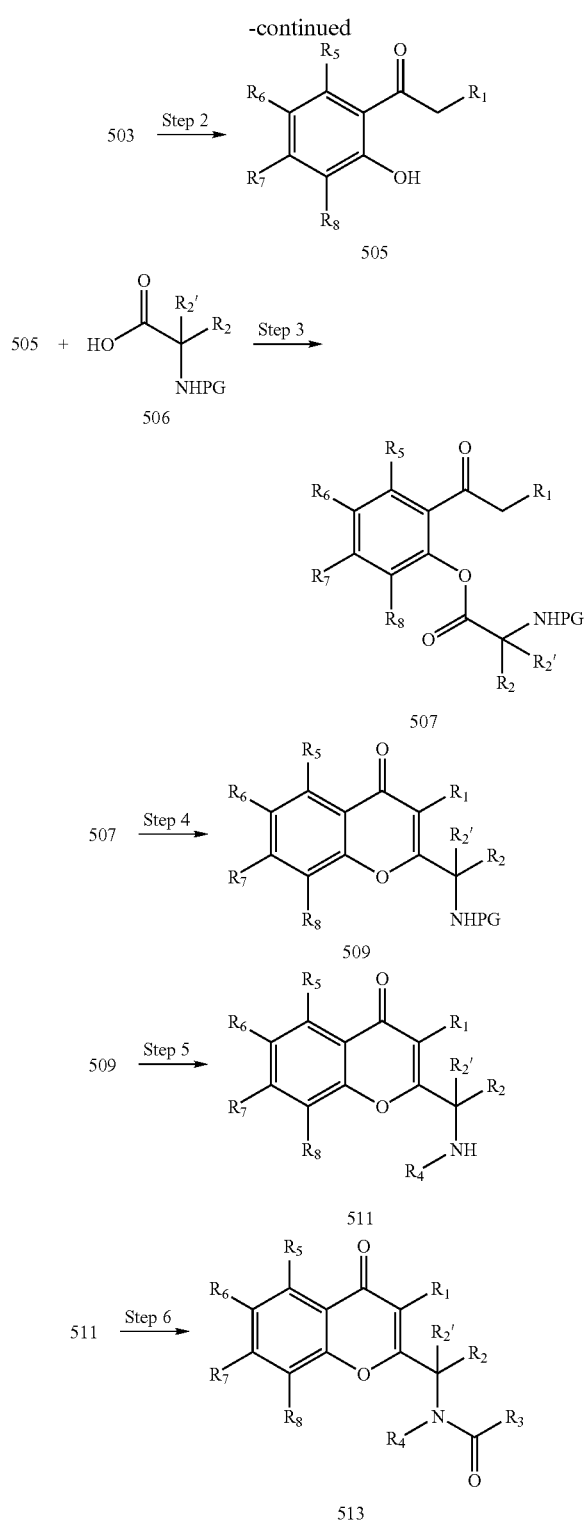

30 minutes, the product, a compound of Formula 503, is isolated and used without any further purification.

Preparation of Compounds of Formula 505

Referring to Reaction Scheme 5, Step 2, $AlCl_3$ (about 1.3 equivalents) is added slowly over about 15 minutes to a compound of Formula 503 at about 140° C. After gas evolution has ceased, the reaction mixture is cooled to room temperature. The product, a compound of Formula 505, is isolated and purified.

Preparation of Compounds of Formula 507

Referring to Reaction Scheme 5, Step 3, a solution of a compound of Formula 505 and an amino acid of Formula 506 (preferably about 1.1 equivalents) in which the amine group has been suitably protected with a protecting group PG (preferably a Boc group), a coupling reagent such as HBTU (preferably about 1.2 equivalents), a base such as TEA, and a nonpolar, aprotic solvent such as $CH_2Cl_2$ is maintained at room temperature for about 5 hours. The product, a compound of Formula 507, is isolated and purified.

Preparation of Compounds of Formula 509

Referring to Reaction Scheme 5, Step 4, a mixture of ester of Formula 507 and a base such as potassium carbonate in a polar, aprotic solvent such as DMF is heated at about 140° C. After about 30 mins, the product, a compound of Formula 509, is isolated and purified.

Preparation of Compounds of Formula 511

Referring to Reaction Scheme 5, Step 5, the amine protecting group PG is then removed. When PG is Boc, this may be accomplished by treatment of a compound of formula 509 with aqueous acid (preferably, 97.5:2.5 TFA:$H_2O$) at room temperature for about one hour. The free anine is isolated and used without further purification.

The resulting product; an aldehyde comprising $R_4'$ (i.e., a compound having the formula $R_4.CHO$ where $R_4.CH_2$— is equivalent to $R_4$ and $R_4$ is as described above or is a protected precursor to such a substituent, e.g., (3-oxo-propyl)-carbamic acid tert-butyl ester; preferably, about 1.45 equivalents); a reducing reagent, Such as $Na(OAc)_3BH$; and a nonpolar, aprotic solvent such as $CH_2Cl_2$ is maintained at room temperature for about 3 hours. The product, a compound of Formula 511, is isolated and purified.

Preparation of Compounds of Formula 513

Referring to Reaction Scheme 5, Step 6, to a solution of a compound of Formula 511, a base such as diisoproylethylamine, and a nonpolar, aprotic solvent such as $CH_2Cl_2$ at room temperature is added an acid chloride of the formula $R_3COCl$ (preferably about 2 equivalents). After about 2.5 h, the product, a compound of Formula 513, is isolated and purified.

Preparation of Compounds of Formula 503

Referring to Reaction Scheme 5, Step 1, to a solution of a compound of Formula 501 and a base such as triethylamine in a nonpolar, aprotic solvent such as $CH_2Cl_2$ at room temperature is added about an equivalent of an acid chloride of formula Cl—(CO)—$CH_2R_1$ over about 5 minutes. After about Reaction Scheme 6

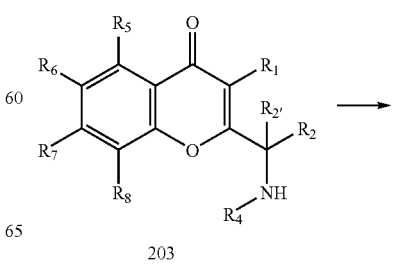

203

-continued

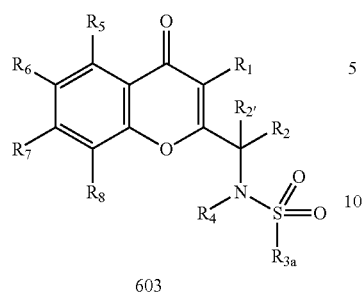

603

Referring to Reaction Scheme 6, to a solution of a compound of Formula 203 and an amine base such as diisopropylethylamine in a nonpolar, aprotic solvent such as dichloromethane is added a compound having the formula Cl—S(O)$_2$—R$_{3a}$, or O—(S(O)$_2$—R$_{3a}$)$_2$ where R$_{3a}$ is as described above. The resulting Solution is stirred under nitrogen at room temperature for several hours. The product, a compound of Formula 603 is isolated and purified.

Reaction Scheme 7

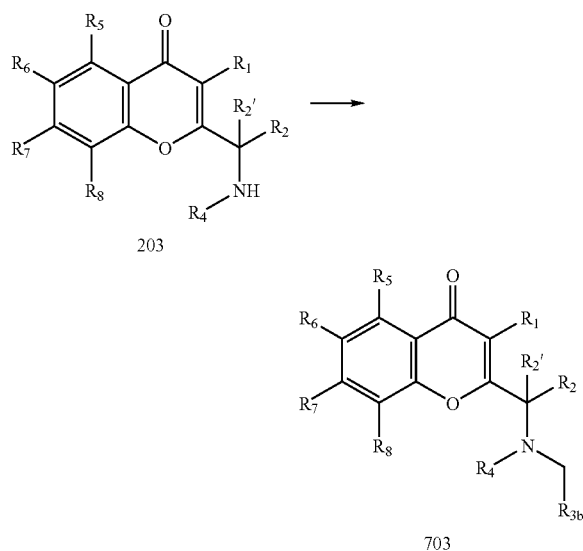

Referring to Reaction Scheme 7, to a solution of a compound of Formula 203 and an amine base such as diisopropylethylamine in a nonpolar, aprotic solvent such as dichloromethane is added a compound having the formula X—CH$_2$—R$_{3b}$, where R$_{3b}$ is as described above and X is Br, Cl, mesylate, or tosylate. The resulting solution is stirred under nitrogen at room temperature or with heat for several hours. The product, a compound of Formula 703 is isolated and purified.

Reaction Scheme 8

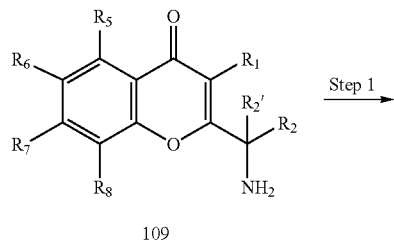

109

-continued

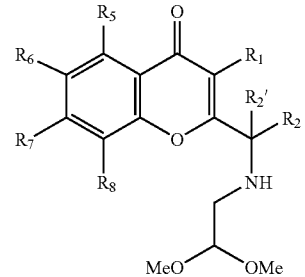

803

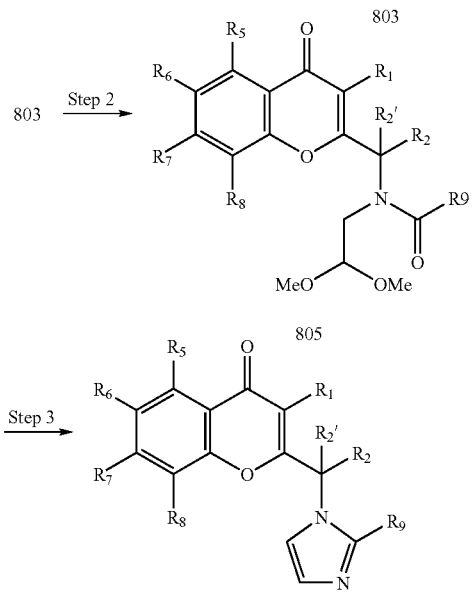

807

Preparation of Formula 803

Referring to Reaction Scheme 8 Step 1, to an optionally substituted compound of Formula 109 dissolved in a polar, aprotic solvent (such as DMF) in the presence of a base (such as potassium carbonate) is added one equivalent of an optionally substituted suitably protected aldehyde wherein such aldehyde further comprises a leaving group, preferably, a halide (such as bromoacetaldehyde dimethylacetal). The solution is heated at reflux, monitoring completion of the reaction (e.g. by TLC). The reaction mixture is cooled and the corresponding, optionally substituted compound of Formula 803 is isolated and purified.

Preparation of Formula 805

Referring to Reaction Scheme 8, Step 2, to an optionally Substituted compound of Formula 803 in an inert solvent (such as dichloromethane) in the presence of about 1.5 molar equivalents of an amine base (Such as triethylamine) is added about 1.5 molar equivalents of an R$_9$ acid chloride, such as, Cl—C(O)—R$_9$, where R$_9$ is as described herein. The reaction takes place, with stirring, at room temperature over a period of 4 to 24 hours. Completion is monitored. e.g., by TLC. The corresponding compound of Formula 805 is isolated and purified.

Preparation of Formula 807

Referring to Reaction Scheme 8, Step 3, a solution of a compound of Formula 805 and an excess of ammonium acetate in acetic acid is heated at reflux for 1-4 hours. Completion is monitored, e.g., by TLC. The corresponding compound of Formula 807 is isolated and purified.

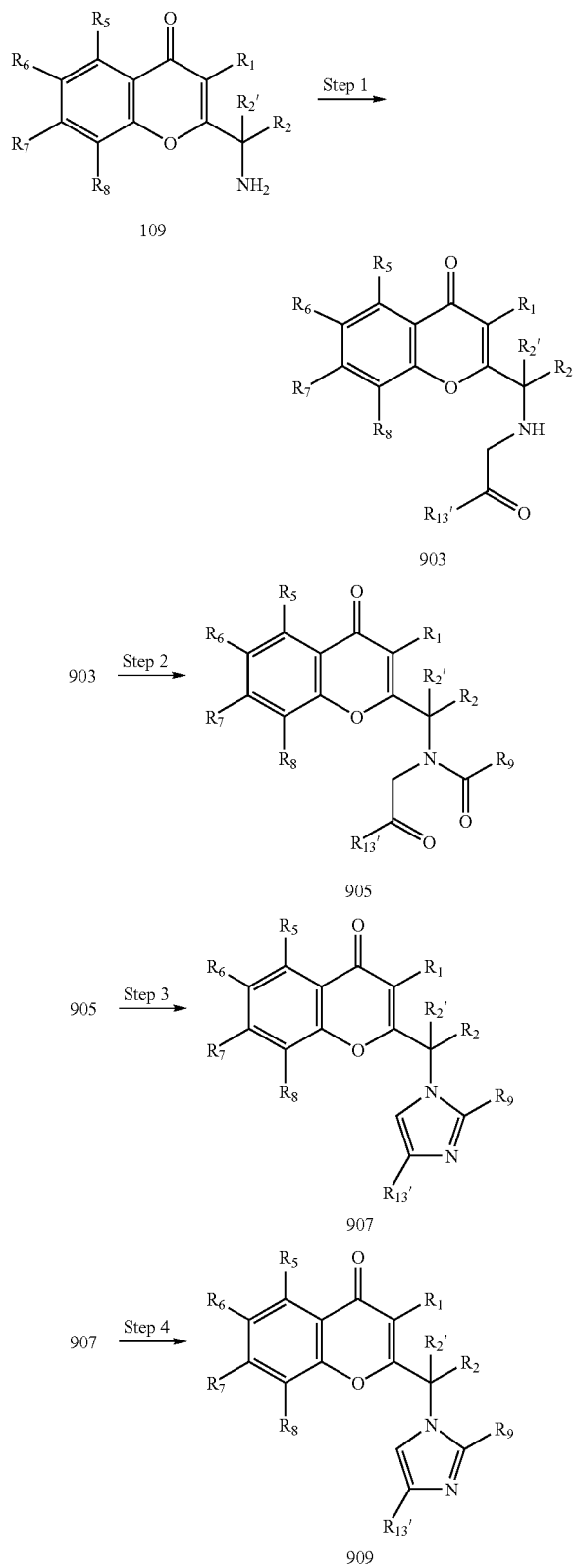

Preparation of Formula 903

Referring to Reaction Scheme 9, Step 1, a suspension of a compound of Formula 109, an alpha-haloketone reagent of the Formula $R_{13'}(CO)CH_2X$ wherein X is a halide and $R_{13'}$ is as described herein, and about an equivalent of a base, such as potassium carbonate in a polar, aprotic solvent such as DMF is stirred at room temperature. The reaction is diluted with water and the resulting compounds a compound of Formula 903, typically a sold, is used in the subsequent step without purification. Where the resulting compound is not a solid, it is isolated using standard procedures and then used in the subsequent step.

Preparation of Formula 905

Referring to Reaction Scheme 9, Step 2, a solution of the compound of Formula 903, about an equivalent of an amine base, Such as triethylamine and about an equivalent of an acid chloride (such as a compound of Formula $R_9$—COCl) in an organic solvent such as methylene chloride is stirred at room temperature for several hours. Completion is monitored, e.g., by TLC. The corresponding compound of Formula 905 is isolated and purified.

Preparation of Formula 907

Referring to Reaction Scheme 9, Step 3, a solution of a compound of Formula 905 and an excess of ammonium acetate in acetic acid is heated at reflux using a Dean-Stark trap and condenser. Completion is monitored, e.g., by TLC. The corresponding compound of Formula 907 is isolated and purified.

Preparation of Formula 909

Referring to Reaction Scheme 9, Step 4, when $R_{13'}$ comprises a protected aminoalkyl group, the amino protected group may be removed. For example, when the amino group is protected as the corresponding phthalimide, the protecting group is removed as follows. A solution of a compound of Formula 907 and an excess of anhydrous hydrazine in a polar, protic solvent such as ethanol is heated at reflux. The reaction is cooled to about 5° C. and any precipitate is filtered off. The filtrate is concentrated in vacuo and purified to yield a compound of Formula 909. One of skill in the art will appreciate that other conditions may be used to remove other protecting groups.

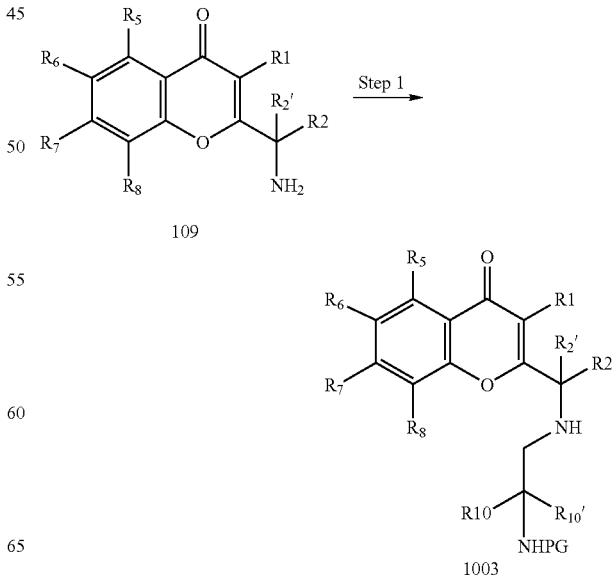

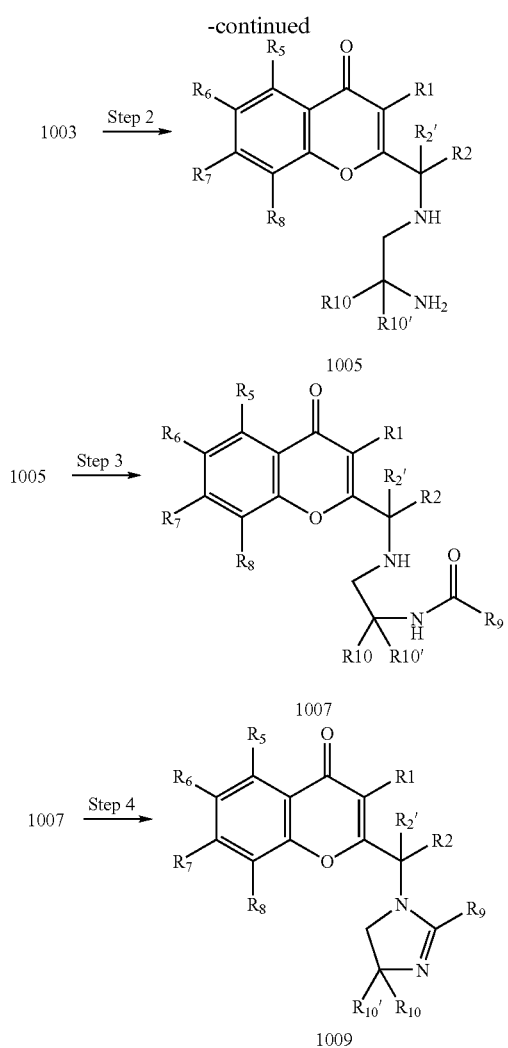

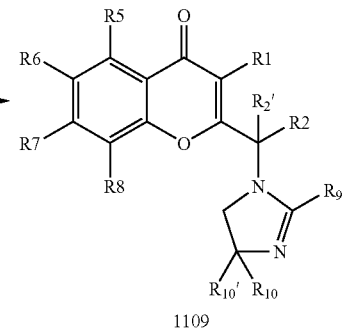

Preparation of Formula 1007

Referring to Reaction Scheme 10, Step 3, to a solution of a compound of Formula 1005 in a nonpolar, aprotic solvent such as dichloromethane is added an excess, preferably about two equivalents of a amine base such as triethylamine, followed by about an equivalent or slight excess of an acid chloride of the formula $R_9$—CO—Cl. The resultant solution is stirred at ambient temperature for about 3 hours. Completion is monitored, e.g., by TLC. The corresponding compound of Formula 1007 is isolated and purified

Preparation of Formula 1009

Referring to Reaction Scheme 10, Step 4, a solution of a compound of Formula 1007 in an excess of phosphorus oxychloride is heated at reflux. After 8 hours, the reaction mixture is allowed to cool to ambient temperature and concentrated under reduced pressure. The corresponding compound of Formula 1009 is isolated and purified.

Preparation of Formula 1003

Referring to Reaction Scheme 10, Step 1, reductive amination of amines of Formula 109 with an optionally substituted, aldehyde-containing carbamic acid ester gives urethane intermediates. More specifically, to a solution of a compound of Formula 109 and an equivalent of a suitably protected aldehyde (Seki et. al. *Chem. Pharm. Bull.* 1996, 44, 2061) in dichloromethane is added a slight excess of a reducing agent, such as sodium triacetoxyborohydride. The resultant cloudy mixture is maintained at ambient temperature. Completion is monitored, e.g., by TLC. The corresponding compound of Formula 1003 is isolated and used in the subsequent step without purification.

Preparation of Formula 1005

Referring to Reaction Scheme 10, Step 2, the amino protecting group PG is then removed. When PG is a Boc protecting group, this may be accomplished by the treatment of a solution of a compound of Formula 1003 in a nonpolar, aprotic solvent such as dichloromethane with a strong acid such as trifluoroacetic acid. The resultant solution is maintained at ambient temperature overnight and concentrated under reduced pressure. The residue is isolated to give a compound of Formula 1005 which was used in the subsequent step without purification.

Preparation of Formula 1109

As an alternative to Steps 3 and 4 of Reaction Scheme 10, acylation of primary amines of Formula 1005, followed by acetic acid mediated cyclization, can proceed without isolation of the intermediate amides to provide the target compound of Formula 1109. This route is shown in Reaction Scheme 11.

More specifically, to a Solution of a compound of Formula 1005 in a nonpolar, aprotic solvent such as dichloromethane is added an excess, preferably about two equivalents of an amine base, such as triethylamine, followed by about an equivalent of an acid chloride of the formula $R_9$—CO—Cl. The resultant solution is stirred at ambient temperature for 2 hours, then evaporated under reduced pressure. The resultant solid is treated with glacial acetic acid, then the resultant suspension is heated at reflux for about 48 hours. The reaction is cooled to ambient temperature then evaporated under reduced pressure. The corresponding compound of Formula 1109 is isolated and purified.

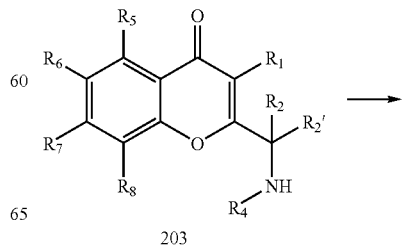

-continued

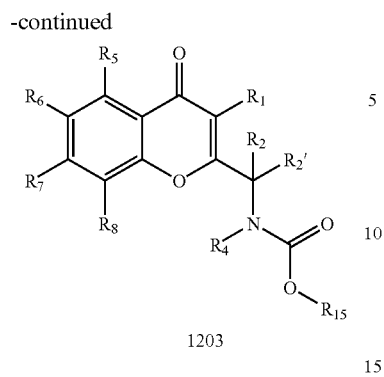

1203

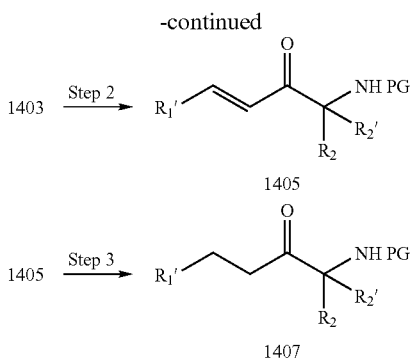

1405

1407

Referring to Reaction Scheme 12, a compound of Formula 203 is reacted with a slight excess of a compound of the formula $R_{15}O(CO)Cl$ in the presence of a base such as triethylamine in a nonpolar, aprotic solvent such as dichloromethane. The product, a compound of Formula 1203 is isolated and purified.

Reaction Scheme 13

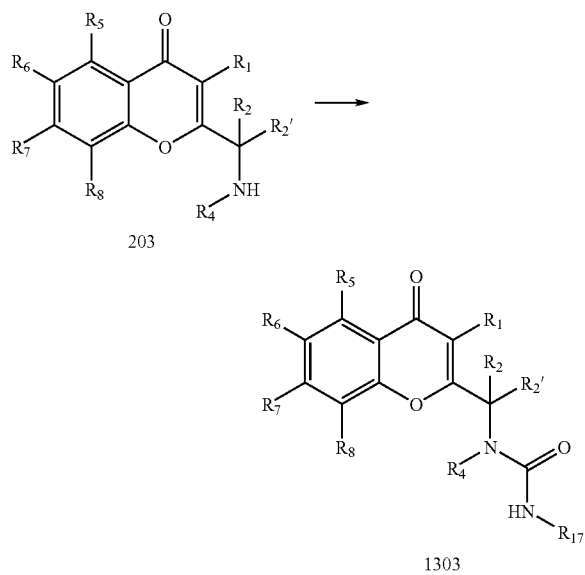

Referring to Reaction Scheme 13, a compound of Formula 203 is treated with a slight excess of an isocyanate $R_{17}$—N=C=O in the presence of a base, such as triethylamine, in a nonpolar, aprotic solvent, such as dichloromethane. The product, a compound of Formula 1303, is isolated and purified.

Preparation of Compounds of Formula 1403

Referring to Reaction Scheme 14, Step 1, a nonpolar, aprotic solvent, such as THF, and an excess of a solution of an optionally substituted vinyl magnesium bromide in a nonpolar, aprotic solvent (and more preferably, about three equivalents of a 1.0 M solution of an optionally substituted vinyl magnesium bromide in THF) is cooled to −78° C. while stirring under a nitrogen atmosphere. The mixture is treated dropwise with a solution of a compound of Formula 1401 in a nonpolar, aprotic solvent, such as THF over about 30 min. After the mixture is stirred for 30 min at −78° C., the cooling bath is removed and the reaction mixture is warmed slowly to room temperature overnight (about 15 h). The product, a compound of Formula 1403, is isolated and purified.

Preparation of Compounds of Formula 1405

Referring to Reaction Scheme 14, Step 2, to a solution of a compound of Formula 1403 in an anhydrous, nonpolar, aprotic solvent, such as acetonitrile under an inert atmosphere, such as argon, is added about an equivalent of a compound of the Formula $R_1$—X wherein $R_{1'}$ is an optionally susbituted vinyl, optionally susbituted aryl, or optionally substituted heteroaryl and X is I, Br, or —OTf, and a base such as triethylamine followed by palladium (II) acetate (preferably about 0.025 equivalents). The resulting solution is heated to about 80° C. After about 15 h. the reaction mixture is allowed to cool to room temperature. The product, a compound of Formula 1405, is isolated and immediately purified.

Preparation of Compounds of Formula 1407

To a Solution of a compound of Formula 1405 in a nonpolar, aprotic solvent such as ethyl acetate under nitrogen is added 10 wt % palladium on carbon. The nitrogen is replaced with a balloon of hydrogen and the flask is purged. After 3 h, the reaction flask is purged with nitrogen and filtered through a pad of celite (rinsing with a solvent such as ethyl acetate). The product, a compound of Formula 1407 is isolated and purified.

Reaction Scheme 14

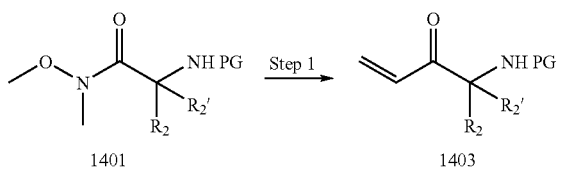

Reaction Scheme 15

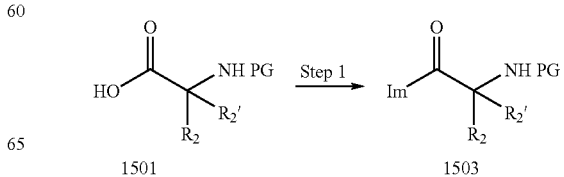

-continued

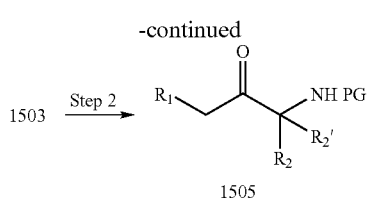

1503 →(Step 2)

1505

Preparation of Compounds of Formula 1503

Referring to Reaction Scheme 15, Step 1, about one equivalent of carbonyldiimidazole is added slowly to a room temperature solution of a compound of Formula 1501 (preferably wherein the amino protecting group PG is Boc) in a nonpolar, aprotic solvent such THF. After about one hour, the product, a compound of Formula 1503, is isolated and used without further purification.

Preparation of Compounds of Formula 1505

Referring to Reaction Scheme 15, Step 2, a Grignard reagent is prepared from a compound of Formula $R_1CH_2Br$ and magnesium turnings in a nonpolar, aprotic solvent such as THF. A solution of a compound of Formula 1503 in a nonpolar, aprotic solvent such as THF is cooled to about 0-5° C. The solution or the Grignard reagent is then added via syringe to the 0-5° C. solution of the compound of Formula 1503. The temperature is monitored by internal thermometer and is not allowed to exceed about 15° C. The reaction mixture is maintained at about 0-5° C. for about one hour. The product, a compound of Formula 1505, is isolated and purified.

Preferred Processes and Last Steps

A compound of Formula I is optionally contacted with a pharmaceutically acceptable acid or base to form the corresponding acid or base addition salt.

A pharmaceutically acceptable acid addition salt of a compound of Formula I is optionally contacted with a base to form the corresponding free base of Formula I. A pharmaceutically acceptable base addition salt of a compound of Formula I is optionally contacted with an acid to form the corresponding free acid of Formula I.

Preferred Compounds

Preferred $R_1$ when Either $R_2$ or $R_{2'}$ is not Hydrogen

When considering the compounds of Formula I, in a preferred embodiment when either one or both $R_2$ or $R_{2'}$ is not hydrogen (more preferably, either one of $R_2$ or $R_{2'}$ is not hydrogen), $R_1$ is selected from hydrogen, optionally substituted $C_1$-$C_8$ alkyl, optionally substituted aryl, optionally substituted heteroaryl, optionally substituted aryl-$C_1$-$C_4$-alkyl-, and optionally substituted heteroaryl-$C_1$-$C_4$-alkyl- (more preferably optionally substituted aryl and optionally substituted aryl-$C_1$-$C_4$-alkyl-). In a more preferred embodiment $R_1$ is selected from hydrogen, optionally substituted $C_1$-$C_4$ alkyl, optionally substituted phenyl-$C_1$-$C_4$-alkyl-, optionally substituted naphthalenylmethyl, optionally substituted phenyl, and naphthyl. More preferably. $R_1$ is optionally substituted phenyl-$C_1$-$C_4$-alkyl- or optionally substituted heteroaryl-$C_1$-$C_4$-alkyl-.

In a most preferred embodiment $R_1$ is napthyl, phenyl, bromophenyl, chlorophenyl, methoxyphenyl, ethoxyphenyl, tolyl, dimethylphenyl, chorofluorophenyl, methylchlorophenyl, ethyl phenyl, phenethyl, benzyl, chlorobenzyl, methylbenzyl, methoxybenzyl, cyanobenzyl, hydroxylbenzyl, dichlorobenzyl, dimethoxybenzyl, or naphthalenylmethyl. More preferably, $R_1$ is benzyl, cyanobenzyl, methoxybenzyl, or naphthalenylmethyl. Most preferably, $R_1$ is benzyl.

Preferred $R_1$ when $R_2$ and $R_{2'}$ are Hydrogen

In an embodiment wherein $R_2$ and $R_{2'}$ are both hydrogen, preferably $R_1$ is chosen from optionally substituted aryl, optionally substituted aryl-$C_1$-$C_4$-alkyl-, optionally substituted heteroaryl, and optionally substituted heteroaryl-$C_1$-$C_4$-alkyl-, provided however, that $R_1$ is not substituted phenyl. More preferably, $R_1$ is optionally substituted aryl-$C_1$-$C_4$-alkyl- or optionally substituted heteroaryl-$C_1$-$C_4$-alkyl-. More preferably, when $R_2$ and $R_{2'}$ are both hydrogen, $R_1$ is selected from optionally substituted phenyl-$C_1$-$C_4$-alkyl, and optionally substituted naphthalenylmethyl. In a more preferred embodiment wherein $R_2$ and $R_{2'}$ are both hydrogen, $R_1$ is chosen from benzyl, chlorobenzyl, methylbenzyl, methoxybenzyl, cyanobenzyl, hydroxybenzyl, dichlorobenzyl, dimethoxybenzyl, and naphthalenylmethyl. More preferably, $R_1$ is benzyl, cyanobenzyl, methoxybenzyl, or naphthalenylmethyl. More preferably, $R_1$ is benzyl.

Preferred $R_2$

When considering the compounds of Formula I and as will be appreciated by those skilled in the art, the compounds described herein possess a potentially chiral center at the carbon to which $R_2$ and $R_{2'}$ are attached. The $R_2$ and $R_{2'}$ groups may be the same or different; if different, the compound is chiral (i.e., has a stereogenic center). When $R_2$ and $R_{2'}$ are different, in preferred embodiments $R_{2'}$ is hydrogen and $R_2$ is other than hydrogen. The invention contemplates the use of pure enantiomers and mixtures of enantiomers, including racemic mixtures, although the use of a substantially optically pure enantiomer will generally be preferred. The term "substantially optically pure" or "enantiomerically pure" means having at least about 95% of the described enantiomer with no single impurity greater than about 1% and preferably, at least about 97.5% enantiomeric excess. In a preferred embodiment, the stereogenic center to which $R_2$ and $R_{2'}$ are attached is of the R configuration.

In one embodiment, $R_2$ is optionally substituted $C_1$-$C_4$ alkyl, and $R_{2'}$ is hydrogen or optionally substituted $C_1$-$C_4$ alkyl. More preferably, $R_{2'}$ is hydrogen and $R_2$ is optionally substituted $C_1$-$C_4$ alkyl. In a most preferred embodiment $R_2$ is chosen from methyl, ethyl, propyl (particularly, c-propyl or i-propyl), butyl (particularly, t-butyl), methylthioethyl, methylthiomethyl, aminobutyl, (CBZ)aminobutyl, cyclohexylmethyl, benzyloxymethyl, methylsulfinylethyl, methylsulfinylmethyl, and hydroxymethyl, and $R_{2'}$ is hydrogen. Especially preferred is when $R_{2'}$ is hydrogen and $R_2$ is ethyl or propyl (particularly, c-propyl or i-propyl). More preferably, $R_2$ is i-propyl. More preferred is the embodiment wherein the stereogenic center to which $R_2$ and $R_{2'}$ is attached is of the R configuration.

In another embodiment, both $R_2$ and $R_{2'}$ are hydrogen.

Preferred $R_3$ Groups when $R_{12}$ is —$N(R_4)(COR_3)$

When considering the compounds of Formula I wherein $R_{12}$ is —$N(R_4)(COR_3)$, in a preferred embodiment $R_3$ is selected from optionally substituted $C_1$-$C_8$ alkyl, optionally substituted aryl-$C_1$-$C_4$-alkyl-, optionally substituted heteroaryl-$C_1$-$C_4$-alkyl-, optionally substituted heteroaryl, optionally substituted aryl, $R_{15}O$— and $R_{17}$—NH—, $R_{15}$ is chosen from optionally substituted $C_1$-$C_8$ alkyl and optionally substituted aryl, and $R_{17}$ is chosen from hydrogen, optionally substituted $C_1$-$C_8$ alkyl and optionally substituted aryl. Preferred $R_3$ are optionally substituted $C_1$-$C_8$ alkyl (e.g., $C_1$-$C_8$ alkyl substituted with lower-alkoxy), optionally substituted heteroaryl, and optionally substituted aryl.

In a more preferred embodiment, when $R_3$ is not $R_{17}$NH— or $R_{15}$O—, $R_3$ is chosen from phenyl; phenyl substituted with one or more of the following substituents: halo, $C_1$-$C_4$ alkyl, $C_1$-$C_4$ alkyl substituted with hydroxy (e.g., hydroxymethyl), $C_1$-$C_4$ alkoxy. $C_1$-$C_4$ alkyl substituted with $C_1$-$C_4$ alkoxy, nitro, formyl, carboxy, cyano, methylenedioxy, ethylenedioxy, acyl (e.g., acetyl), —N-acyl (e.g., N-acetyl) or trifluoromethyl; benzyl; phenoxymethyl-; halophenoxymethyl-; phenylvinyl-; heteroaryl-; heteroaryl-substituted with $C_1$-$C_4$ alkyl or $C_1$-$C_4$ alkyl substituted with halo (e.g., $CF_3$); $C_1$-$C_4$ alkyl substituted with $C_1$-$C_4$-alkoxy- and benzyloxymethyl-.

In a most preferred embodiment, when $R_3$ is not $R_{17}$NH— or $R_{15}$O—, $R_3$ is chosen from phenyl, halophenyl, dihalophenyl, cyanophenyl, halo(trifluoromethyl)phenyl, hydroxymethylphenyl, methoxyphenyl, ethoxyphenyl, carboxyphenyl, ethylphenyl, tolyl, methylenedioxyphenyl, ethlenedixoyphenyl, methoxychlorophenyl, dihydro-benzodioxinyl, methylhalophenyl, trifluoromethylphenyl, bis(trifluoromethyl)phenylbenzyl, furanyl, $C_1$-$C_4$ alkyl substituted furanyl, trifluoromethylfuranyl, $C_1$-$C_4$ alkyl substituted trifluoromethylfuranyl, benzofuranyl, thiophenyl, $C_1$-$C_4$ alkyl substituted thiophenyl, benzothiophenyl, benzothiadiazolyl, pyridinyl, indolyl, methylpyridinyl, trifluoromethylpyridinyl, pyrrolyl, quinolinyl, picolinyl, pyrazolyl. $C_1$-$C_4$ alkyl substituted pyrazolyl N-methyl pyrazolyl, $C_1$-$C_4$ alkyl substituted N-methyl pyrazolyl, $C_1$-$C_4$ alkyl substituted pyrazinyl, $C_1$-$C_4$ alkyl substituted isoxazolyl, benzoisoxazolyl, morpholinomethyl, methylthiomethyl, methoxymethyl, N-methyl imidazolyl, and imidazolyl. Yet more preferably, $R_3$ is tolyl, halophenyl, halomethylphenyl, hydroxymethylphenyl, methylenedioxyphenyl, formylphenyl or cyanophenyl.

In a more preferred embodiment, when $R_3$ is $R_{17}$NH—, $R_{17}$ is chosen from hydrogen, $C_1$-$C_4$ alkyl; cyclohexyl; phenyl; and phenyl substituted with halo. $C_1$-$C_4$ alkyl. $C_1$-$C_4$ alkoxy, or $C_1$-$C_4$ alkylthio.

In a most preferred embodiment, when $R_3$ is $R_{17}$NH—, $R_{17}$ is hydrogen isopropyl, butyl, cyclohexyl, phenyl, bromophenyl, dichlorophenyl, methoxyphenyl, ethylphenyl, tolyl, trifluoromethylphenyl or methylthiophenyl.

In an embodiment, wherein $R_3$ is $R_{15}$O—, $R_{15}$ is chosen from optionally substituted $C_1$-$C_8$ alkyl and optionally substituted aryl.

Preferred $R_{3a}$ Groups when $R_{12}$ is —N($R_4$)($SO_2R_{3a}$)

Preferably, when $R_{12}$ is —N($R_4$)($SO_2R_{3a}$), $R_{3a}$ is chosen from $C_1$-$C_{13}$ alkyl; phenyl; naphthyl; phenyl substituted with halo, $C_1$-$C_4$ alkyl, $C_1$-$C_4$ alkoxy, cyano, nitro, methylenedioxy, or trifluoromethyl; biphenylyl and heteroaryl. More preferably, $R_{3a}$ is chosen from phenyl substituted with halo, $C_1$-$C_4$ alkyl, $C_1$-$C_4$ alkoxy, cyano, nitro, methylenedioxy, or trifluoromethyl and naphthyl.

Preferred $R_{3b}$ Groups when $R_{12}$ is —N($R_4$)($CH_2R_{3b}$)

Preferably, when $R_{12}$ is —N($R_4$)($CH_2R_{3b}$), $R_{3b}$ is chosen from $C_1$-$C_{13}$ alkyl; substituted $C_1$-$C_4$ alkyl; phenyl; naphthyl; phenyl substituted with carboxy, alkoxycarbonyl cyano, halo, $C_1$-$C_4$ alkyl-, $C_1$-$C_4$ alkoxy, nitro, methylenedioxy, or trifluoromethyl; biphenylyl, benzyl; and heterocyclyl.

Most preferably, $R_{3b}$ is chosen from halophenyl, polyhalophenyl, methylhalophenyl, tolyl, dimethylphenyl, methoxyphenyl, dimethoxyphenyl, cyanophenyl, trifluoromethylphenyl, trifluoromethoxyphenyl, bis(trifluoromethyl) phenyl, carboxyphenyl, t-butylphenyl, methoxycarbonylphenyl, piperidinyl and naphthyl.

Preferred $R_4$ Groups when $R_{12}$ is —NH$R_4$, —N($R_4$)($COR_3$), or —N($R_4$)($CH_2R_{3b}$)

In a preferred embodiment when $R_{12}$ is —NH$R_4$, —N($R_4$) ($COR_3$), or —N($R_4$)($CH_2R_{3b}$). $R_4$ is chosen from hydrogen, optionally substituted $C_1$-$C_{13}$ alkyl, optionally substituted aryl, optionally substituted aryl-$C_1$-$C_4$-alkyl-, optionally substituted heterocyclyl, and optionally substituted heteroaryl-$C_1$-$C_4$-alkyl- (preferably hydrogen or optionally substituted $C_1$-$C_{13}$ alkyl).

More preferably, $R_4$ is chosen from hydrogen, $C_1$-$C_4$ alkyl; cyclohexyl; phenyl substituted with hydroxyl, $C_1$-$C_4$ alkoxy or $C_1$-$C_4$ alkyl; benzyl; heteroarylmethyl-; heteroarylethyl-; heteroarylpropyl-; and $R_{16}$-alkylene-, wherein $R_{16}$ is hydroxyl, di($C_1$-$C_4$ alkyl)amino-, ($C_1$-$C_4$ alkyl)amino-, amino, $C_1$-$C_4$ alkoxy-, or N-heterocyclyl-, particularly pyrrolidino, piperidino or imidazolyl.

More preferably, $R_4$ is $R_{16}$-alkylene-, wherein $R_{16}$ is amino, $C_1$-$C_4$ alkylamino-, di($C_1$-$C_4$ alkyl)amino-, $C_1$-$C_4$ alkoxy-, hydroxyl, or N-heterocyclyl. Preferably $R_{16}$ is amino.

In a most preferred embodiment when $R_{12}$ is —NH$R_4$, —N($R_4$)($COR_3$), or —N($R_4$)($CH_2R_{3b}$), $R_4$ is chosen from hydrogen, methyl, ethyl, propyl, butyl, cyclohexyl, carboxyethyl, carboxymethyl, methoxyethyl, hydroxyethyl, hydroxypropyl dimethylaminoethyl, dimethylaminopropyl, diethylaminoethyl, diethylaminopropyl, aminopropyl, methylaminopropyl, 2,2-dimethyl-3-(dimethylamino)propyl, 1-cyclohexyl-4-(diethylamino)butyl, aminoethyl, aminobutyl, aminopentyl, aminohexyl, aminoethoxyethyl, isopropylaminopropyl, diisopropylaminoethyl, 1-methyl-4-(diethylamino)butyl, (t-Boc)aminopropyl, hydroxyphenyl, benzyl, methoxyphenyl, methylmethoxyphenyl, dimethylphenyl, tolyl, ethylphenyl, (oxopyrrolidinyl)propyl, (methoxycarbonyl)ethyl, benzylpiperidinyl, pyridinylethyl, pyridinylmethyl, morpholinylethyl morpholinylpropyl, piperidinyl, azetidinylmethyl, azetidinylethyl, azetidinylpropyl, pyrrolidinylethyl, pyrrolidinylpropyl, piperidinylmethyl, piperidinylethyl, imidazolylpropyl, imidazolylethyl, (ethylpyrrolidinyl)methyl, (methylpyrrolidinyl)ethyl, (methylpiperidinyl)propyl, (methylpiperazinyl)propyl, furanylmethyl and indolylethyl.

More preferably, $R_4$ is aminoethyl, aminopropyl, aminobutyl, aminopentyl, aminohexyl, methylaminoethyl, methylaminopropyl, methylaminobutyl, methylaminopentyl, methylaminohexyl, dimethylaminoethyl, dimethylaminopropyl, dimethylaminobutyyl, dimethylaminopentyl, dimethylaminohexyl, ethylaminoethyl, ethylaminopropyl, ethylaminobutyl, ethylaminopentyl, ethylaminohexyl, diethylaminoethyl, diethylaminopropyl, diethylaminobutyyl, diethylaminopentyl, or diethylaminohexyl, most preferably aminopropyl.

Preferred $R_4$ Groups when $R_{12}$ is —N($R_4$)($SO_2R_{3a}$)

Preferably, when $R_{12}$ is —N($R_4$)($SO_2R_{3a}$), $R_4$ is chosen from $C_1$-$C_4$ alkyl, cyclohexyl; phenyl substituted with hydroxyl, $C_1$-$C_4$ alkoxy or $C_1$-$C_4$ alkyl; benzyl; heteroarylmethyl-; heteroarylethyl-; heteroarylpropyl-; heteroarylethyl-; heteroaryl prolyl- and $R_{16}$-alkylene-, wherein $R_{16}$ is hydroxyl, di($C_1$-$C_4$ alkyl)amino-, ($C_1$-$C_4$ alkyl)amino-, amino, $C_1$-$C_4$ alkoxy-, or N-heterocyclyl-, particularly pyrrolidino, piperidino or imidazolyl.

$R_{12}$ is an Imidazole

Preferably, when $R_{12}$ is an imidazole, $R_{12}$ has the formula:

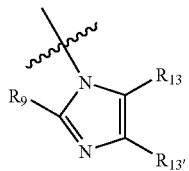

wherein $R_9$ is chosen from hydrogen, optionally substituted $C_1$-$C_8$ alkyl, optionally substituted aryl, optionally substituted aryl-$C_1$-$C_4$-alkyl-, optionally substituted heteroaryl-$C_1$-$C_4$-alkyl-, optionally substituted aryl-$C_1$-$C_4$-alkoxy-, optionally substituted heteroaryl-$C_1$-$C_4$-alkoxy-, optionally substituted heteroaryl-; and $R_{13}$ and $R_{13'}$ are independently hydrogen, optionally substituted $C_1$-$C_8$ alkyl, optionally substituted aryl, or optionally substituted aryl-$C_1$-$C_4$-alkyl- (preferably optionally substituted aryl). More preferably, $R_9$ is phenyl substituted with $C_1$-$C_4$-alkyl, $C_1$-$C_4$-alkoxy-, and/or halo (especially $C_1$-$C_4$-alkyl and/or halo); phenyl; or benzyl. Yet more preferably, $R_9$ is tolyl; halophenyl; or halomethylphenyl.

In a preferred embodiment, $R_{13}$ is hydrogen and $R_{13'}$ is substituted $C_1$-$C_4$ alkyl. More preferably, $R_{13}$ is hydrogen and $R_{13'}$ is aminomethyl, aminoethyl, aminopropyl, acetylaminomethyl, acetylaminoethyl, benzyloxycarbonylamino-methyl or benzyloxycarbonylamino-ethyl.

$R_{12}$ is an Imidazoline

Preferably, when $R_{12}$ is an imidazoline, $R_{12}$, has the formula

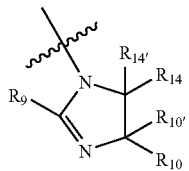

wherein $R_9$ is chosen from hydrogen, optionally substituted $C_1$-$C_8$ alkyl, optionally substituted aryl, optionally substituted aryl-$C_1$-$C_4$-alkyl-, and optionally substituted heteroaryl-; and $R_{10}$, $R_{10'}$, $R_{14}$, and $R_{14'}$ are independently chosen from hydrogen, optionally substituted $C_1$-$C_8$ alkyl, optionally substituted aryl, and optionally substituted aryl-$C_1$-$C_4$-alkyl-. More preferably, $R_9$ is methylenedioxyphenyl; phenyl; phenyl substituted with $C_1$-$C_4$ alkyl, $C_1$-$C_4$ alkoxy, and/or halo; or benzyl. In a preferred embodiment, $R_9$ is methylenedioxyphenyl-; phenyl; or phenyl substituted with methoxy, halo and/or methyl (preferably halo and/or methyl, including tolyl), more preferably methylenedioxyphenyl or said substituted phenyls In another preferred embodiment, $R_{10}$, $R_{10'}$, $R_{14}$, and $R_{14'}$ are independently hydrogen or optionally substituted alkyl (preferably optionally substituted $C_1$-$C_4$ alkyl). More preferably, $R_{10}$ and $R_{10'}$ are independently selected from the group consisting of hydrogen or optionally substituted $C_1$-$C_4$ alkyl (and more particularly, methyl or aminoalkyl-) and $R_{14'}$ and $R_{14}$ are hydrogen.

Preferred $R_5$, $R_6$, $R_7$, and $R_8$ Groups

When considering the compounds of Formula I, in other preferred embodiments $R_5$, $R_6$, $R_7$ and $R_8$ are independently chosen from hydrogen; acyl; alkyl; alkyl substituted with alkyl, alkoxy, halo, hydroxyl, nitro, cyano, dialkylamino, alkylsulfonyl, alkylsulfonamido, alkylthio, carboxyalkyl, carboxamido, aminocarbonyl, lower-alkylaminocarbonyl- (e.g. methylaminocarbonyl- or ethylaminocarbonyl-), di(lower-alkyl)aminocarbonyl- (e.g. dimethylaminocarbonyl- or diethylaminocarbonyl-), aryl, or heteroaryl; alkoxy; alkoxy substituted with alkyl, acyl, alkoxy, halo, hydroxyl, nitro, cyano, dialkylamino, alkylsulfonyl, alkylsulfonamido, alkylthio, carboxyalkyl, carboxamido, aminocarbonyl, lower-alkylaminocarbonyl- (e.g. methylaminocarbonyl- or ethylaminocarbonyl-), di(lower-alkyl)aminocarbonyl- (e.g. dimethylaminocarbonyl- or diethylaminocarbonyl-), aryl, or heteroaryl; halogen; hydroxyl; nitro; cyano; dialkylamino; alkylsulfonyl; alkylsulfonamido; alkylthio; carboxyalkyl; carboxamido; amidocarbonyl; aryl; aryl substituted with alkyl, acyl, alkoxy, halo, hydroxyl, nitro, cyano, dialkylamino, alkylsulfonyl, alkylsulfonamido, alkylthio, carboxyalkyl, carboxamido, aminocarbonyl, lower-alkylaminocarbonyl- (e.g. methylaminocarbonyl- or ethylaminocarbonyl-), di(lower-alkylaminocarbonyl- (e.g. dimethylaminocarbonyl- or diethylaminocarbonyl-), aryl, or heteroaryl; heteroaryl or heteroaryl substituted with alkyl, acyl, alkoxy, halo, hydroxyl, nitro, cyano, dialkylamino, alkylsulfonyl, alkylsulfonamido, alkylthio, carboxyalkyl, carboxamido, aminocarbonyl, lower-alkylaminocarbonyl- (e.g. methylaminocarbonyl- or ethylaminocarbonyl-), di(lower-alkyl) aminocarbonyl- (e.g. dimethylaminocarbonyl- or diethylaminocarbonyl-), aryl, or heteroaryl.

More preferably, $R_5$, $R_6$, $R_7$, and $R_8$ are independently chosen from hydrogen, amino, alkylamino, hydroxyl, halogen (particularly chloro and fluoro), $C_1$-$C_4$ alkyl (particularly methyl), $C_1$-$C_4$ haloalkyl (particularly trifluoromethyl), $C_1$-$C_4$ alkoxy (particularly methoxy), $C_1$-$C_4$ haloalkoxy and cyano. More preferably, $R_5$, $R_6$, $R_7$, and $R_8$ are methoxy, hydrogen, cyano, or halo (especially Cl, F). Further preferred for each of the specific substituents: $R_5$ is amino, alkylamino, trifluoromethyl, hydrogen or halo; $R_6$ is hydrogen, alkyl (particulary, methyl) or halo; $R_7$ is hydrogen, halo, alkyl (particulary, methyl), alkoxy (particularly, methoxy), cyano, or trifluoromethyl; and $R_8$ is hydrogen or halo. Still further preferred are the compounds where only one of $R_5$, $R_6$, $R_7$, and $R_8$ is not hydrogen, especially $R_7$. More preferred are the compounds where $R_5$, $R_6$ and $R_8$ are hydrogen and $R_7$ is cyano, methoxy or halogen (especially Cl, F).

Preferred Salt Forms

Preferred compounds will generally be capable of forming acid addition salts (i.e., will comprise a site which reacts with a pharmaceutically acceptable acid to form an acid addition salt.) The present invention includes pharmaceutically acceptable acid addition salts of the compounds of Formula I. Acid addition salts of the present compounds are prepared in a standard manner in a suitable solvent from the parent compound and an excess of an acid, such as hydrochloric, hydrobromic, sulfuric, phosphoric, acetic, maleic, succinic or methanesulfonic. Preferred salt forms are hydrochloric, phosphoric, and oxalic acid salts with the hydrochloric acid salt form being especially preferred.

The salts and/or solvates of the compounds of the formula (I) which are not pharmaceutically acceptable may be useful as intermediates in the preparation of pharmaceutically acceptable salts and/or solvates of compounds of formula (I)

or the compounds of the formula (I) themselves, and as such form another aspect of the present invention.

Preferred Subgenus

In a particularly preferred subgenus of compounds of Formula I, $R_1$ is benzyl, halobenzyl, methoxybenzyl-, cyanobenzyl, or naphthalenylmethyl-; $R_2$ is ethyl or propyl: $R_{2'}$ is hydrogen; $R_5$ is hydrogen; $R_6$ is hydrogen; $R_7$ is halo, cyano, methoxy or hydrogen: $R_8$ is hydrogen, and $R_{12}$ is —$NR_4$(COR$_3$) wherein $R_3$ is optionally substituted aryl (preferably, halophenyl, halomethylphenyl-, methylenedioxyphenyl-, methoxyphenyl-, ethoxyphenyl-, cyanophenyl- or phenyl substituted with lower-acyl or lower-alkylaminocarbonyl-, e.g. methylaminocarbonyl- or ethylaminocarbonyl-, or di(lower-alkyl)aminocarbonyl-, e.g. dimethylaminocarbonyl- or diethylaminocarbonyl-; and $R_4$ is $R_{16}$-alkylene- wherein $R_{16}$ is hydroxyl, di($C_1$-$C_4$)alkylamino-, ($C_1$-$C_4$ alkyl)amino-, amino, pyrrolidino, piperidino, imidazolyl or morpholino (more preferably in such embodiments, $R_1$ is benzyl, halobenzyl, methoxybenzyl, cyanobenzyl, or naphthalenylmethyl; and $R_2$ is propyl (especially i- or c-propyl).

In another particularly preferred subgenus of compounds of Formula I, $R_1$ is benzyl, halobenzyl, methoxybenzyl-, cyanobenzyl, or naphthalenylmethyl-; $R_1$ is ethyl or propyl; $R_{2'}$ is hydrogen; $R_5$ is hydrogen; $R_6$ is hydrogen; $R_7$ is halo, cyano, methoxy or hydrogen; $R_8$ is hydrogen; $R_{12}$ is —NR(CH$_2$R$_{3b}$) wherein $R_4$ is $R_{16}$-alkylene- wherein $R_{16}$ is hydroxyl, di($C_1$-$C_4$)alkylamino-, ($C_1$-$C_4$ alkyl)amino-, amino, pyrrolidino, piperidino, imidazolyl or morpholino; and $R_{3b}$, is optionally substituted aryl.

In a particularly preferred subgenus of compounds of Formula I, $R_1$ is benzyl, halobenzyl, methoxybenzyl, cyanobenzyl, or naphthalenylmethyl; $R_2$ is chosen from ethyl or propyl; $R_{2'}$ is hydrogen; $R_5$ is hydrogen; $R_6$ is hydrogen; $R_7$ is halo, cyano, methoxy or hydrogen; $R_8$ is hydrogen; and $R_{12}$ is optionally substituted imidazolinyl of the above formula wherein $R_{10}$, $R_{10'}$, $R_{14}$ and $R_{14'}$ are independently hydrogen or optionally substituted alkyl (preferably optionally substituted $C_1$-$C_4$ alkyl); and $R_9$ is optionally substituted phenyl (preferably, halophenyl, halomethylphenyl, tolyl, or methylenedioxyphenyl). More preferably in such embodiments $R_1$ is benzyl, methoxybenzyl, or cyanobenzyl; $R_2$ is propyl (especially i- or c-propyl); and $R_{16}$ is amino.

In a particularly preferred subgenus of compounds of Formula I, $R_1$ is benzyl, halobenzyl, methoxybenzyl, cyanobenzyl, or naphthalenylmethyl; $R_2$ is chosen from ethyl or propyl; $R_{2'}$ is hydrogen; $R_5$ is hydrogen; $R_6$ is hydrogen; $R_7$ is halo, cyano, methoxy or hydrogen; $R_8$ is hydrogen; and $R_{12}$ is optionally substituted imidazole of the above for wherein $R_{13}$ is hydrogen and $R_{13'}$ is hydrogen or optionally substituted alkyl (preferably optionally substituted $C_1$-$C_4$ alkyl); and $R_9$ is optionally substituted aryl (preferably, halophenyl, halomethylphenyl, tolyl, or methylenedioxyphenyl). More preferably, $R_{13}$ is hydrogen and $R_{13'}$ is aminomethyl, aminoethyl, aminopropyl, acetylamino-ethyl, acetylaminoethyl, benzyloxycarbonylamino-methyl or Benzyloxycarbonylamino-ethyl. More preferably in such embodiments $R_1$ is benzyl, methoxybenzyl, or cyanobenzyl; $R_2$ is propyl (especially i- or c-propyl); and $R_{16}$ is amino.

When $R_{12}$ is —N(R$_4$)(SO$_2$R$_{3a}$), $R_1$ is most preferably chosen from $C_1$-$C_4$ alkyl, benzyl, substituted benzyl and substituted phenyl; $R_2$ is $C_1$-$C_4$ alkyl; $R_{2'}$ is hydrogen; $R_{3a}$ is chosen from substituted phenyl and naphthyl; $R_4$ is $R_{16}$-alkylene-, $R_7$ is hydrogen, fluoro, methyl or chloro; $R_5$, $R_6$ and $R_8$ are hydrogen; and $R_{16}$ is chosen from hydroxyl, di($C_1$-$C_4$)amino, ($C_1$-$C_4$ alkyl)amino, amino, pyrrolidino, piperidino, imidazolyl and morpholino.

When $R_{12}$ is —NHR$_4$ or —N(R$_4$)(CH$_2$R$_{3b}$), $R_1$ is preferably chosen from hydrogen, optionally substituted $C_1$-$C_4$ alkyl, optionally substituted benzyl, optionally substituted phenyl, and optionally substituted naphthalenylmethyl; $R_2$ is optionally substituted $C_1$-$C_4$ alkyl and $R_{2'}$ is hydrogen; $R_{3b}$ is chosen from optionally substituted alkyl; optionally substituted phenyl; biphenylyl, optionally substituted aralkyl; and optionally substituted heterocyclyl; and $R_4$ is chosen from hydrogen, optionally substituted $C_1$-$C_4$ alkyl; cyclohexyl; optionally substituted phenyl; optionally substituted benzyl; heterocyclyl; heteroarylmethyl; heteroarylethyl; and heteroarylpropyl. More preferably. $R_4$ is $R_{16}$-alkylene, wherein $R_{16}$ is hydroxyl, di($C_1$-$C_4$)alkylamino-, ($C_1$-$C_4$ alkyl)amino-, amino, $C_1$-$C_4$ alkoxy-, or N-heterocyclyl.

When $R_{12}$ is —NHR$_{14}$ or —N(R$_4$)(CH$_2$R$_{3b}$), $R_1$ is most preferably chosen from $C_1$-$C_4$ alkyl, optionally substituted benzyl, and optionally substituted phenyl (more preferably optionally substituted benzyl, e.g., benzyl, cyanobenzyl); $R_2$ is optionally substituted $C_1$-$C_4$ alkyl (more preferably propyl, especially i- or c-propyl); $R_{2'}$ is hydrogen; $R_{3b}$ is chosen from optionally substituted phenyl, optionally substituted heterocyclyl and naphthyl; $R_4$ is chosen from hydrogen, optionally substituted benzyl optionally substituted heterocyclyl and $R_{16}$-alkylene-; $R_6$ and $R_7$ are chosen from halo, cyano, methoxy or hydrogen; $R_5$ and $R_8$ are hydrogen and $R_{16}$ is chosen from di($C_1$-$C_4$ alkylamino)-, ($C_1$-$C_4$ alkyl)amino-, amino, pyrrolidinyl, piperidinyl, imidazolyl and morpholinyl.

In a particularly preferred subgenus of compounds of Formula I, $R_1$ is benzyl halobenzyl (especially Cl-benzyl and F-benzyl), methoxybenzyl-, cyanobenzyl, or naphthalenylmethyl-; $R_2$ is ethyl or propyl; $R_{2'}$ is hydrogen; $R_5$ is hydrogen; $R_6$ is hydrogen; $R_7$ is halo, cyano, methoxy or hydrogen; $R_8$ is hydrogen; and $R_{12}$ is —NHR$_4$ wherein $R_4$ is hydrogen (more preferably in such embodiments, $R_1$ is benzyl, halobenzyl, cyanobenzyl; and $R_2$ is propyl, especially i-propyl or c-propyl).

When $R_{3b}$ is present, it is most preferably chosen from phenyl substituted with one or more halo, methyl, methoxy, cyano, trifluoromethyl, trifluoromethoxy, carboxy, and or methoxycarbonyl groups [e.g., halophenyl, polyhalophenyl, tolyl, dimethylphenyl, methoxyphenyl, dimethoxyphenyl, cyanophenyl, trifluoromethylphenyl, trifluoromethoxyphenyl, bis(trifluoromethyl)phenyl, carboxyphenyl, t-butylphenyl, methoxycarbonylphenyl]; piperidinyl and naphthyl.

Particularly preferred compounds include:

N-(3-Amino-propyl)-N-{1-[3-(3-cyano-benzyl)-7-hydroxy-4-oxo-4H-chromen-2-yl]-2-methyl-propyl}-3-fluoro-4-methyl-benzamide;

4-Acetyl-N-(3-amino-propyl)-N-[1-(3-benzyl-7-methoxy-4-oxo-4H-chromen-2-yl)-2-methyl-propyl]-benzamide;

2{-1-[4-(2-Amino-ethyl)-2-p-tolyl-imidazol-1-yl]-2-methyl-propyl}-3-benzyl-4-oxo-4H-chromene-7-carbonitrile;

3-Benzyl-2-[1-(4,4-dimethyl-2-p-tolyl-4,5-dihydro-imidazol-1-yl)-2-methyl-propyl]-4-oxo-4H-chromene-7-carbonitrile;

Benzo[1,3]dioxole-5-carboxylic acid (3-amino-propyl)-{1-[7-chloro-3-(3-cyano-benzyl)-4-oxo-4H-chromen-2-yl]-2-methyl-propyl}-amide;

N-(3-Amino-propyl)-N-{1-[7-chloro-3-(3-cyano-benzyl)-4-oxo-4H-chromen-2-yl]-2-methyl-propyl}-4-methyl-benzamide;

N-(3-Amino-propyl)-N-[1-(7-chloro-3-naphthalen-1-yl methyl-4-oxo-4H-chromen-2-yl)-2-methyl-propyl]-2-methoxy-acetamide;

4-Acetyl-N-(3-amino-propyl)-N-[1-(3'-benzyl-7-cyano-4-oxo-4H-chromen-2-yl)-2-methyl-propyl]-benzamide;

N-(3-amino-propyl)-N-{1-[7-chloro-3-(3-cyano-benzyl)-4-oxo-4H-chromen-2-yl]-2-methyl-propyl}-3-fluoro-4-methyl-benzamide,
Benzo[1,3]dioxole-5-carboxylic acid (3-amino-propyl)-[1-(3-benzyl-7-fluoro-4-oxo-4H-chromen-2-yl)-2-methyl-propyl]-amide;
-Benzo-[1,3]dioxole-5-carboxylic acid (3-amino-propyl)-[1-(3-benzyl-7-cyano-4-oxo-4H-chromen-2-yl)-2-methyl-propyl]-amide;
3-Benzyl-2-[1-(4,4-dimethyl-2-p-tolyl-4,5-dihydro-imidazol-1-yl)-2-methyl-1)propyl]-7-hydroxy-chromen-4-one;
N-(3-Amino-propyl)-N-[1-(3-benzyl-7-fluoro-4-oxo-4H-chromen-2-yl)-2-methyl-propyl]-3-fluoro-4-methyl-benzamide;
N-(3-Amino-propyl)-N-[1-(3-benzyl-7-methoxy-4-oxo-4H-chromen-2-yl)-2-methyl-propyl]-3-fluoro-4-methyl-benzamide;
N-(3-Amino-propyl)-N-[1-(3-benzyl-7-methoxy-4-oxo-4H-chromen-2-yl)-2-methyl-propyl]-4-methyl-benzamide;
3-Benzyl-2-[1-(4,4-dimethyl-2-p-tolyl-4,5-dihydro-imidazol-1-yl)-2-methyl-propyl]-7-methoxy-chromen-4-one;
3-Benzyl-7-fluoro-2-{1-[2-(3-fluoro-4-methyl-phenyl)-4,4-dimethyl-4,5-dihydro-imidazol-1-yl]-2-methyl-propyl}-chromen-4-one;
3-Benzyl-2-[1-(4,4-dimethyl-2-p-tolyl-4,5-dihydro-imidazol-1-yl)-2-methyl-propyl]-7-fluoro-chromen-4-one;
3-Benzyl-2-{1-[2-(3-fluoro-4-methyl-phenyl)-4,4-dimethyl-4,5-dihydro-imidazo-1-yl]-2-methyl-propyl}-7-cyano-chromen-4-one;
N-(3-Amino-propyl)-N-[1-(3-benzyl-7-fluoro-4-oxo-4H-chromen-2-yl)-2-methyl-propyl]-4-methyl-benzamide;
4-Acetyl-N-(3-amino-propyl)-N-[1-(3-benzyl-7-chloro-4-oxo-4H-chromen-2-yl)-2-methyl-propyl]-benzamide;
N-(3-Amino-propyl)-3-fluoro-N-{1-[7-fluoro-3-(3-methoxy-benzyl)-4-oxo-4H-chromen-2-yl]-2-methyl-propyl}-4-methyl-benzamide;
4-Acetyl-N-(3-amino-propyl)-N-{1-[7-chloro-3-(3-cyano-benzyl)-4-oxo-4H-chromen-2-yl]-2-methyl-propyl}-benzamide;
(2-{1-[1-(3-Benzyl-7-chloro-4-oxo-4H-chromen-2-yl)-2-methyl-propyl]-2-p-tolyl-1H-imidazol-4-yl}-ethyl)-carbamic acid benzyl ester;
2-[1-(2-Benzo[1,3]dioxol-5-yl-4,4-dimethyl-4,5-dihydro-imidazol-1-yl)-2-methyl-propyl]-3-benzyl-7-cyano-chromen-4-one;
4-Acetyl-N-(3-amino-propyl)-N-[1-(3-benzyl-7-fluoro-4-oxo-4H-chromen-2-yl)-2-methyl-propyl]-benzamide;
N-(3-Amino-propyl)-N-[1-(3-benzyl-7-chloro-4-oxo-4H-chromen-2-yl)-2-methyl-propyl]-3-fluoro-4-methyl-benzamide,
N-(3-Amino-propyl)-N-{1-[7-fluoro-3-(3-methoxy-benzyl)-4-oxo-4H-chromen-2-yl]-2-methyl-propyl}-4-methoxy-benzamide;
Benzo[1,3]dioxole-5-carboxylic acid (3-amino-propyl)-{1-[7-fluoro-3-(3-methoxy-benzyl)-4-oxo-4H-chromen-2-yl]-2-methyl-propyl}-amide;
2-{1-[4-(2-Amino-ethyl)-2-p-tolyl-imidazol-1-yl]-2-methyl-propyl}-3-benzyl-7-chloro-chromen-4-one;
N-(3-Amino-propyl)-N-[1-(3-benzyl-7-hydroxy-4-oxo-4H-chromen-2-yl)-2-methyl-propyl]-3-fluoro-4-methyl-benzamide;
Benzo[1,3]dioxole-5-carboxylic acid (3-amino-propyl)-[1-(3-benzyl-7-chloro-4-oxo-4H-chromen-2-yl)-2-methyl-propyl]-amide;
N-(3-Amino-propyl)-N-[1-(3-benzyl-7-hydroxy-4-oxo-4H-chromen-2-yl)-2-methyl-propyl]-4-methyl-benzamide;
N-(3-Amino-propyl)-N-{1-[7-fluoro-3-(3-methoxy-benzyl)-4-oxo-4H-chromen-2-yl]-2-methyl-propyl}-2-methoxy-acetamide;
N-(3-Amino-propyl)-N-{1-[7-fluoro-3-(3-methoxy-benzyl)-4-oxo-4H-chromen-2-yl]-2-methyl-propyl}-4-methyl-benzamide;
N-(3-Amino-propyl)-N-[(3-benzyl-7-chloro-4-oxo-4H-chromen-2-yl)-cyclopropyl-methyl]-4-methyl-benzamide;
2,3-Dihydro-benzo[1,4]dioxine-6-carboxylic acid (3-amino-propyl)-[1-(3-benzyl-7-chloro-4-oxo-4H-chromen-2-yl)-2-methyl-propyl]-amide;
N-(3-Amino-propyl)-3-fluoro-N-{1-[7-cyano-3-(3-methoxy-benzyl)-4-oxo-4H-chromen-2-yl]-2-methyl-propyl}-4-methyl-benzamide;
3-Benzyl-7-chloro-2-[2-methyl-1-(2-p-tolyl-4,5-dihydro-imidazol-1-yl)-propyl]-chromen-4-one;
3-Benzyl-7-fluoro-2-{1-[2-(3-fluoro-4-methyl-phenyl)-4,5-dihydro-imidazol-1-yl]-2-methyl-propyl}-chromen-4-one;
2-[1-(4-Aminomethyl-2-p-tolyl-imidazol-1-yl)-2-methyl-propyl]-3-benzyl-7-chloro-chromen-4-one;
3-Benzyl-7-methoxy-2-[2-methyl-1-(2-p-tolyl-4,5-dihydro-imidazol-1-yl)-propyl)]-chromen-4-one;
2-[1-(2-Benzo[1,3]dioxol-5-yl-4,5-dihydro-imidazol-1-yl)-2-methyl-propyl]-3-benzyl-7-chloro-chromen-4-one;
4-Acetyl-N-(3-amino-propyl)-N-[1-(3-benzyl-7-chloro-4-oxo-4H-chromen-2-yl)-2-methyl-propyl]-benzamide;
4-Acetyl-N-(3-amino-propyl)-N-{1-[7-cyano-3-(3-methoxy-benzyl)-4-oxo-4H-chromen-2-yl]-2-methyl-propyl}-benzamide;
3-Benzyl-7-chloro-2-{1-[2-(3-fluoro-4-methyl-phenyl)-4,5-dihydro-imidazol-1-yl]-2-methyl-propyl}1-chromen-4-one;
3-Benzyl-7-fluoro-2-[2-methyl-1-(2-p-tolyl-4,5-dihydro-imidazol-1-yl)-propyl]-chromen-4-one;
2-[1-(2-Benzo[1,3]dioxol-5-yl-4,5-dihydro-imidazol-1-yl)-2-methyl-propyl]-3-benzyl-7-fluoro-chromen-4-one;
N-(3-Amino-propyl)-N-{1-[7-cyano-3-(3-methoxy-benzyl)-4-oxo-4H-chromen-2-yl]-2-methyl-propyl}-4-methyl-benzamide;
Benzo[1,3]dioxole-5-carboxylic acid (3-amino-propyl)-{1-[7-cyano-3-(3-methoxy-benzyl)-4-oxo-4H-chromen-2-yl]-2-methyl-propyl}-amide;
3-(2-{1-[2-(3-Fluoro-4-methyl-phenyl)-4,5-dihydro-imidazol-1-yl]-2-methyl-propyl}-7-methoxy-4-oxo-4H-chromen-3-ylmethyl)-benzonitrile;
3-{7-Chloro-2-[2-methyl-1-(2-p-tolyl-4,5-dihydro-imidazol-1-yl)-propyl]-4-oxo-4H-chromen-3-ylmethyl}-benzonitrile;
3-{7-Methoxy-2-[2-methyl-1-(2-p-tolyl-4,5-dihydro-imidazol-1-yl)-propyl]-4-oxo-4H-1-chromen-3-ylmethyl}-benzonitrile;
3-{7-Fluoro-2-[2-methyl-1-(2-p-tolyl-4,5-dihydro-imidazol-1-yl)-propyl]-4-oxo-4H-chromen-3-ylmethyl}-benzonitrile;
N-(3-Amino-propyl)-N-{1-[7-chloro-3-(3-methoxy-benzyl)-4-oxo-4H-chromen-2-yl]-2-methyl-propyl}-3-fluoro-4-methyl-benzamide;
N-(3-Amino-propyl)-N-{1-[3-(3-cyano-benzyl)-7-methoxy-4-oxo-4H-chromen-1-yl]-2-methyl-propyl}-4-methyl-benzamide;
N-(3-Amino-propyl)-N-{1-[3-(3-cyano-benzyl)-7-methoxy-4-oxo-4H-chromen-2-yl]-2-methyl-propyl}-3-fluoro-4-methyl-benzamide;

3-{2-[1-(2-Benzo[1,3]dioxol-5-yl-4,5-dihydro-imidazol-1-yl)-2-methyl-propyl]-7-fluoro-4-oxo-4H-chromen-3-ylmethyl}-benzonitrile;

3-Benzyl-2-{1-[2-(3-fluoro-4-methyl-phenyl)-4,5-dihydro-imidazol-1-yl]-2-methyl-propyl}-4-oxo-4H-chromene-7-carbonitrile;

2-[1-(2-Benzo[1,3]dioxol-5-yl-4,5-dihydro-imidazol-1-yl)-2-methyl-propyl]-3-benzyl-4-oxo-4H-chromene-7-carbonitrile;

3-(7-Chloro-2-{1-[2-(3-fluoro-4-methyl-phenyl)-4,5-dihydro-imidazol-1-yl]-2-methyl-propyl}-4-oxo-4H-chromen-3-ylmethyl)-benzonitrile;

3-{2-[1-(2-Benzo[1,3]dioxol-5-yl-4,5-dihydro-imidazol-1-yl)-2-methyl-propyl]-7-methoxy-4-oxo-4H-chromen-3-ylmethyl}-benzonitrile;

3-(7-Fluoro-2-{1-[2-(3-fluoro-4-methyl-phenyl)-4,5-dihydro-imidazol-1-yl]-2-methyl-propyl}-4-oxo-4H-chromen-3-ylmethyl)-benzonitrile;

Benzo[1,3]dioxole-5-carboxylic acid (3-amino-propyl)-{1-[7-cyano-3-(3-cyano-benzyl)-4-oxo-4H-chromen-2-yl]-2-methyl-propyl}-amide;

Benzo[1,3]dioxole-5-carboxylic acid (3-amino-propyl)-{1-[3-(3-cyano-benzyl)-7-methoxy-4-oxo-4H-chromen-2-yl]-2-methyl-propyl}-amide;

Benzo[1,3]dioxole-5-carboxylic acid (3-amino-propyl)-{1-[3-(3-cyano-benzyl)-7-fluoro-4-oxo-4H-chromen-2-yl]-2-methyl-propyl}-amide;

N-(3-Amino-propyl)-N-{1-[3-(3-cyano-benzyl)-7-fluoro-4-oxo-4H-chromen-2-yl]-2-methyl-propyl}-4-methyl-benzamide;

Benzo[1,3]dioxole-5-carboxylic acid (3-amino-propyl)-{1-[7-chloro-3-(3-methoxy-benzyl)-4-oxo-4H-chromen-2-yl]-2-methyl-propyl}-amide;

N-(3-Amino-propyl)-N-{1-[7-cyano-3-(3-cyano-benzyl)-4-oxo-4H-chromen-2-yl]-2-methyl-propyl}-4-methyl-benzamide;

3-Benzyl-2-[2-methyl-1-(2-p-tolyl-4,5-dihydro-imidazol-1-yl)-propyl]-4-oxo-4H-chromene-7-carbonitrile;

2-[1-(2-Benzo[1,3]dioxol-5-yl-4,5-dihydro-imidazol-1-yl)-2-methyl-propyl]-3-benzyl-7-methoxy-chromen-4-one;

N-(3-Amino-propyl)-N-{1-[7-chloro-3-(3-methoxy-benzyl)-4-oxo-4H-chromen-2-yl]-2-methyl-propyl}-2-methoxy-acetamide;

N-(3-Amino-propyl)-N-{1-[7-cyano-3-(3-cyano-benzyl)-4-oxo-4H-chromen-2-yl]-2-methyl-propyl}-3-fluoro-4-methyl-benzamide;

N-(3-Amino-propyl)-N-{1-[3-(3-cyano-benzyl)-7-fluoro-4-oxo-4H-chromen-2-yl]-2-methyl-propyl}-3-fluoro-4-methyl-benzamide;

2-{1-[4-(2-Amino-ethyl)-2-p-tolyl-imidazol-1-yl]-2-methyl-propyl}-7-chloro-3-(3-methoxy-benzyl)-chromen-4-one;

2-{1-[4-(2-Amino-ethyl)-2-(3-fluoro-4-methyl-phenyl)-imidazol-1-yl]-2-methyl-propyl}-3-benzyl-7-fluoro-chromen-4-one;

2-{1-[4-(2-Amino-ethyl)-2-(3-fluoro-4-methyl-phenyl)-imidazol-1-yl]-2-methyl-propyl}-3-benzyl-4-oxo-4H-chromene-7-carbonitrile;

2-{1-[4-(2-Amino-ethyl)-2-p-tolyl-imidazol-1-yl]-2-methyl-propyl}-3-benzyl-7-fluoro-chromen-4-one;

2-{1-[4-(2-Amino-ethyl)-2-(3-fluoro-4-methyl-phenyl)-imidazol-1-yl]-2-methyl-propyl}-7-chloro-3-(3-methoxy-benzyl)-chromen-4-one;

2-{1-[4-(2-Amino-ethyl)-2-(3-fluoro-4-methyl-phenyl)-imidazol-1-yl]-2-methyl-propyl}-3-benzyl-7-chloro-chromen-4-one;

3-Benzyl-2-{1-[2-(3-fluoro-4-methyl-phenyl)-4,5-dihydro-imidazol-1-yl]-2-methyl-propyl}-7-methoxy-chromen-4-one;

3-(2-{1-[4-(2-Amino-ethyl)-2-p-tolyl-imidazol-1-yl]-2-methyl-propyl}-7-chloro-4-oxo-4H-chromen-3-ylmethyl)-benzonitrile;

3-(2-{1-[4-(2-Amino-ethyl)-2-(3-fluoro-4-methyl-phenyl)-imidazol-1-yl]-2-methyl-propyl}-7-chloro-4-oxo-4H-chromen-3-ylmethyl)-benzonitrile;

2-{1-[4-(2-Amino-ethyl)-2-p-tolyl-imidazol-1-yl]-2-methyl-propyl}-7-fluoro-3-(3-methoxy-benzyl)-chromen-4-one;

2-{1-[4-(2-Amino-ethyl)-2-(3-fluoro-4-methyl-phenyl)-imidazol-1-yl]-2-methyl-propyl}-3-(3 cyano-benzyl)-4-oxo-4H-chromene-7-carbonitrile;

N-(3-Amino-propyl)-3-fluoro-N-{1-[7-hydroxy-3-(3-methoxy-benzyl)-4-oxo-4H-chromen-2-yl]-2-methyl-propyl}-4-methyl-benzamide;

2-{1-[4-(2-Amino-ethyl)-2-p-tolyl-imidazol-1-yl]-2-methyl-propyl}-3-(3-methoxy-benzyl)-4-oxo-4H-chromene-7-carbonitrile;

N-(3-Amino-propyl)-N-[1-(3-benzyl-7-cyano-4-oxo-4H-chromen-2-yl)-2-methyl-propyl]-4-ethoxy-benzamide;

N-(3-Amino-propyl)-N-[1-(3-benzyl-7-cyano-4-oxo-4H-chromen-2-yl)-2-methyl-propyl]-6-trifluoromethyl-nicotinamide;

N-(3-Amino-propyl)-N-[1-(3-benzyl-7-fluoro-4-oxo-4H-chromen-2-yl)-2-methyl-propyl]-6-trifluoromethyl-nicotinamide;

N-(3-Amino-propyl)-N-[1-(3-benzyl-7-fluoro-4-oxo-4H-chromen-2-yl)-2-methyl-propyl]-isonicotinamide;

N-(3-Amino-propyl)-N-[1-(3-benzyl-7-chloro-4-oxo-4H-chromen-2-yl)-2-methyl-propyl)]-4-cyano-benzamide;

4-Acetylamino-N-(3-amino-propyl)-N-[1-(3-benzyl-7-chloro-4-oxo-4H-chromen-2-yl)-2-methyl-propyl]-benzamide;

N-(3-Amino-propyl)-N-[1-(3-benzyl-7-chloro-4-oxo-4H-chromen-2-yl)-2-methyl-propyl]-6-trifluoromethyl-nicotinamide;

Benzo[1,2,3]thiadiazole-5-carboxylic acid (3-amino-propyl)-[1-(3-benzyl-7-chloro-4-oxo-4H-chromen-2-yl)-2-methyl-propyl]-amide;

Benzo[1,2,3]thiadiazole-5-carboxylic acid (3-amino-propyl)-[1-(3-benzyl-7-fluoro-4-oxo-4H-chromen-2-yl)-2-methyl-propyl]-amide;

4-Acetylamino-N-(3-amino-propyl)-N-[1-(3-benzyl-7-fluoro-4-oxo-4H-chromen-2-yl)-2-methyl-propyl]-benzamide;

Benzo[1,2,3]thiadiazole-5-carboxylic acid (3-amino-propyl)-[1-(3-benzyl-7-fluoro-4-oxo-4H-chromen-2-yl)-2-methyl-propyl]-amide;

N-(3-Amino-propyl)-N-[1-(3-benzyl-7-chloro-4-oxo-4H-1-chromen-2-yl)-2-methyl-propyl]-nicotinamide;

N-(3-Amino-propyl)-N-[1-(3-benzyl-7-fluoro-4-oxo-4H-chromen-2-yl)-2-methyl-propyl]-4-methoxy-benzamide;

Benzo[1,2,3]thiadiazole-5-carboxylic acid (3-amino-propyl)-[1-(3-benzyl-7-cyano-4-oxo-4H-1-chromen-2-yl)-2-methyl-propyl]-amide;

5-Methyl-pyrazine-2-carboxylic acid (3-amino-propyl)-[1-(3-benzyl-7-chloro-4-oxo-4H-chromen-2-yl)-2-methyl-propyl]-amide;

N-(3-Amino-propyl)-N-[1-(3-benzyl-7-cyano-4-oxo-4H-chromen-2-yl)-2-methyl-propyl]-3-dimethylamino-benzamide;

2-[1-(2-Benzo[1,3]dioxol-5-yl-4,5-dihydro-imidazol-1-yl)-2-methyl-propyl]-3-(3-methoxy-benzyl)-4-oxo-4H-chromene-7-carbonitrile;

7-Chloro-3-(3-methoxy-benzyl)-2-[2-methyl-1-(2-p-tolyl-4,5-dihydro-imidazol-1-yl)-propyl]-chromen-4-one;

7-Chloro-2-{1-[2-(3-fluoro-4-methyl-phenyl)-4,5-dihydro-imidazol-1-yl]-2-methyl-propyl}-3-(3-methoxy-benzyl)-chromen-4-one;

2-[1-(2-Benzo[1,3]dioxol-5-yl-4,5-dihydro-imidazol-1-yl)-2-methyl-propyl]-7-chloro-3-(3-methoxy-benzyl)-chromen-4-one;

7-Fluoro-3-(3-methoxy-benzyl)-2-[2-)methyl-1-(2-p-tolyl-4,5-dihydro-imidazol-1-yl)-propyl]-chromen-4-one;

7-Fluoro-2-{1-[2-(3-fluoro-4-methyl-phenyl)-4,5-dihydro-imidazol-1-yl]-2-methyl-propyl}-3-(3-methoxy-benzyl)-chromen-4-one;

2-{1-[4-(2-Amino-ethyl)-2-(3-fluoro-4-methyl-phenyl)-imidazol-1-yl]-2-methyl-propyl}-7-fluoro-3-(3-methoxy-benzyl)-chromen-4-one;

2-{1-[4-(2-Acetylamino-ethyl)-2-(3-fluoro-4-methyl-phenyl)-imidazol-1-yl]-2-methyl-propyl}3-(3-methoxy-benzyl)-4-oxo-4H-chromene-7-carboxylic acid amide;

3-(2-{1-[4-(2-Amino-ethyl)-2-(3-fluoro-4-methyl-phenyl)-imidazol-1-yl]-2-methyl-propyl}-7-fluoro-4-oxo-4H-chromen-3-ylmethyl)-benzonitrile;

N-{1-[1-(3-Benzyl-7-chloro-4-oxo-4H-chromen-2-yl)-2-methyl-propyl]-2-p-tolyl-1H-imidazol-4-ylmethyl}-acetamide;

Benzo[b]thiophene-2-carboxylic acid (3-amino-propyl)-[1-(3-benzyl-7-cyano-4-oxo-4H-chromen-2-yl)-2-methyl-propyl]-amide;

1-Methyl-1H-indole-2-carboxylic acid (3-amino-propyl)-[1-(3-benzyl-7-cyano-4-oxo-4H-chromen-2-yl)-2-methyl-propyl]-amide;

5-tert-Butyl-2-methyl-2H-pyrazole-3-carboxylic acid (3-amino-propyl)-[1-(3-benzyl-7-cyano-4-oxo-4H-chromen-2-yl)-2-methyl-propyl]-amide;

2,5-Dimethyl-2H-pyrazole-3-carboxylic acid (3-amino-propyl)-[1-(3-benzyl-7-cyano-4-oxo-4H-chromen-2-yl)-2-methyl-propyl]-amide;

5-tert-Butyl-2-methyl-2H-pyrazole-3-carboxylic acid (3-amino-propyl)-[1-(3-benzyl-7-fluoro-4-oxo-4H-chromen-2-yl)-2-methyl-propyl]-amide;

2,5-Dimethyl-2H-pyrazole-3-carboxylic acid (3-amino-propyl)-[1-(3-benzyl-7-chloro-4-oxo-4H-chromen-2-yl)-2-methyl-propyl]-amide;

2,5-Dimethyl-2H-pyrazole-3-carboxylic acid (3-amino-propyl)-[1-(3-benzyl-7-fluoro-4-oxo-4H-chromen-2-yl)-2-methyl-propyl]-amide;

5-Methyl-2H-pyrazole-3-carboxylic acid (3-amino-propyl)-[1-(3-benzyl-7-cyano-4-oxo-4H-chromen-2-yl)-2-methyl-propyl]-amide;

5-Methyl-2H-pyrazole-3-carboxylic acid (3-amino-propyl)-[1-(3-benzyl-7-fluoro-4-oxo-4H-chromen-2-yl)-2-methyl-propyl]-amide;

Furan-2-carboxylic acid (3-amino-propyl)-[1-(3-benzyl-7-fluoro-4-oxo-4H-chromen-2-yl)-2-methyl-propyl]-amide;

Furan-2-carboxylic acid (3-amino-propyl)-[1-(3-benzyl-7-chloro-4-oxo-4H-chromen-2-yl)-2-methyl-propyl]-amide;

2,5-Dimethyl-furan-3-carboxylic acid (3-amino-propyl)-[1-(3-benzyl-7-cyano-4-oxo-4H-chromen-2-yl)-2-methyl-propyl]-amide;

2,5-Dimethyl-furan-3-carboxylic acid (3-amino-propyl)-[1-(3-benzyl-7-fluoro-4-oxo-4H-chromen-2-yl)-2-methyl-propyl]-amide, 5-Methyl-thiophene-2-carboxylic acid (3-amino-propyl)-[1-(3-benzyl)-7-cyano-4-oxo-4H-chromen-2-yl)-2-methyl-propyl]-amide;

5-Methyl-thiophene-2-carboxylic acid (3-amino-propyl)-[1-(3-benzyl-7-fluoro-4-oxo-4H-chromen-2-yl)-2-methyl-propyl]-amide;

5-Methyl-isoxazole-3-carboxylic acid (3-amino-propyl)-[1-(3-benzyl-7-chloro-4-oxo-4H-chromen-2-yl)-2-methyl-propyl]-amide;

5-Methyl-2-trifluoromethyl-furan-3-carboxylic acid (3-amino-propyl)-[1-(3-benzyl-7-cyano-4-oxo-4H-chromen-2-yl)-2-methyl-propyl]-amide;

5-Methyl-isoxazole-3-carboxylic acid (3-amino-propyl)-[1-(3-benzyl-7-fluoro-4-oxo-4H-1-chromen-2-yl)-2-methyl-propyl]-amide, 5-Methyl-isoxazole-3-carboxylic acid (3-amino-propyl)-[1-(3-benzyl-7-cyano-4-oxo-4H-chromen-2-yl)-2-methyl-propyl]-amide;

Benzo[c]isoxazole-3-carboxylic acid (3-amino-propyl)-[1-(3-benzyl-7-chloro-4-oxo-4H-chromen-2-yl)-2-methyl-propyl]-amide;

Benzo[c]isoxazole-3-carboxylic acid (3-amino-propyl)-[1-(3-benzyl-7-fluoro-4-oxo-4H-chromen-2-yl)-2-methyl-propyl]-amide;

1-Methyl-1H-pyrrole-2-carboxylic acid (3-amino-propyl)-[1-(3-benzyl-7-fluoro-4-oxo-4H-chromen-2-yl)-2-methyl-propyl]-amide;

1-Methyl-1H-imidazole-4-carboxylic acid (3-amino-propyl)-[(R)-1-(3-benzyl-7-cyano-4-oxo-4H-chromen-2-yl)-2-methyl-propyl]-amide;

N-(3-Amino-propyl)-N-[(R)-1-(3-benzyl-7-cyano-4-oxo-4H-chromen-2-yl)-2-methyl-propyl]-3-dimethylamino-benzamide;

5-Methyl-2-trifluoromethyl-furan-3-carboxylic acid (3-amino-propyl)-[(R)-1-(3-benzyl-7-cyano-4-oxo-4H-chromen-2-yl)-2-methyl-propyl]-amide 5-Methyl-isoxazole-3-carboxylic acid (3-amino-propyl)-[(R)-1-(3-benzyl-7-cyano-4-oxo-4H-chromen-2-yl)-2-methyl-propyl]-amide;

1-Methyl-1H-imidazole-4-carboxylic acid (3-amino-propyl)-[(R)-1-(3-benzyl-7-fluoro-4-oxo-4H-chromen-2-yl)-2-methyl-propyl]-amide;

1-Methyl-1H-pyrrole-2-carboxylic acid (3-amino-propyl)-[(R)-1-(3-benzyl-7-fluoro-4-oxo-4H-chromen-2-yl)-2-methyl-propyl]-amide;

Benzo[c]isoxazole-3-carboxylic acid (3-amino-propyl)-[(R)-1-(3-benzyl-7-fluoro-4-oxo-4H-chromen-2-yl)-2-methyl-propyl]-amide; and 5-Methyl-isoxazole-3-carboxylic acid (3-amino-propyl)-[(R)-1-(3-benzyl-7-fluoro-4-oxo-4H-1-chromen-2-yl)-2-methyl-propyl]-amide.

Utility, Testing and Administration

General Utility

Once made, the compounds of the invention find use in a variety of applications involving alteration of mitosis. As will be appreciated by those skilled in the art, mitosis may be altered in a variety of ways; that is, one can affect mitosis either by increasing or decreasing the activity of a component in the mitotic pathway. Stated differently, mitosis may be affected (e.g., disrupted) by disturbing equilibrium, either by inhibiting or activating certain components. Similar approaches may be used to alter meiosis.

In a preferred embodiment, the compounds of the invention are used to inhibit mitotic spindle formation, thus causing prolonged cell cycle arrest in mitosis. By "inhibit" in this context is meant decreasing or interfering with mitotic spindle formation or causing mitotic spindle dysfunction. By "mitotic spindle formation" herein is meant organization of microtubules into bipolar structures by mitotic kinesins. By "mitotic spindle dysfunction" herein is meant mitotic arrest and monopolar spindle formation.

The compounds of the invention are useful to bind to, and/or inhibit the activity of, a mitotic kinesin, KSP. In a preferred embodiment, the KSP is human KSP, although the compounds may be used to bind to or inhibit the activity of KSP kinesins from other organisms. In this context, "inhibit" means either increasing or decreasing spindle pole separation, causing malformation, i.e., splaying, of mitotic spindle poles, or otherwise causing morphological perturbation of the mitotic spindle. Also included within the definition of KSP for these purposes are variants and/or fragments of KSP. See U.S. Pat. No. 6,437,115, hereby incorporated by reference in its entirety. The compounds of the invention have been shown to have specificity for KSP. However, the present invention includes the use of the compounds to bind to or modulate other mitotic kinesins.

The compounds of the invention are used to treat cellular proliferation diseases. Such disease states which can be treated by the compounds, compositions and methods provided herein include, but are not limited to, cancer (further discussed below), autoimmune disease, fungal disorders, arthritis, graft rejection, inflammatory bowel disease, cellular proliferation induced after medical procedures, including, but not limited to, surgery, angiopolasty, and the like. Treatment includes inhibiting cellular proliferation. It is appreciated that in some cases the cells may not be in an abnormal state and still require treatment. Thus, in one embodiment, the invention herein includes application to cells or individuals afflicted or subject to impending affliction with any one of these disorders or states.

The compounds, compositions and methods provided wherein are particularly deemed useful for the treatment of cancer including solid tumors such as skin, breast, brain, cervical carcinomas, testicular carcinomas, etc. More particularly, cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinonma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor, (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholanigiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma anti (giant cell tumors; Nervous system: skull (osteoma, hemangioma, granuloma, xanthoma, osteitis deformans), meninges (meningiomia, meninigiosarcoma, giliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above identified conditions.

Testing

For assay of KSP-modulating activity, generally either KSP or a compound according to the invention is non-diffusably bound to an insoluble support having isolated sample receiving areas (e.g., a microtiter plate, an array, etc.). The insoluble support may be made of any composition to which the sample can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, Teflon™, etc. Microtiter plates and arrays are especially convenient because a large number of assays can be carried out simultaneously, using small amounts of reagents and samples. The particular manner of binding of the sample is not crucial so long as it is compatible with the reagents and overall methods of the invention, maintains the activity of the sample and is nondiffusable. Preferred methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. Following binding of the sample, excess unbound material is removed by washing. The sample receiving areas may then be blocked through incubation with bovine serum albumin (BSA), casein or other innocuous protein or other moiety.

The compounds of the invention may be used on their own to inhibit the activity of a mitotic kinesin, particularly KSP. In one embodiment, a compound of the invention is combined with KSP and the activity of KSP is assayed. Kinesin (including KSP) activity is known in the art and includes one or more kinesin activities. Kinesin activities include the ability to affect ATP hydrolysis; microtubule binding; gliding and polymerization/depolymerization (effects on microtubule dynamics); binding to other proteins of the spindle; binding to proteins involved in cell-cycle control; serving as a substrate to other enzymes, such as kinases or proteases; and specific kinesin cellular activities such as spindle pole separation.

Methods of performing motility assays are well known to those of skill in the art. (See e.g., Hall, et al. (1996), Biophys. J., 71: 3467-3476, Turner et al., 1996, AnaL. Biochem. 242 (1):20-5; Gittes et al., 1996, Biophys. 70(1): 418-29; Shirakawa et al., 1995, J. Exp. BioL. 198: 1809-15; Winkelmann et al., 1995, Biophys. J. 68: 2444-53; Winkelmann et al. 1995, Biophys. J. 68: 72S.)

Methods known in the art for determining ATPase hydrolysis activity also can be used. Preferably, solution based assays are utilized. U.S. Pat. No. 6,410,254, hereby incorporated by reference in its entirety, describes such assays. Alternatively, conventional methods are used. For example, $P_i$ release from kinesin can be quantified. In one preferred embodiment, the ATPase hydrolysis activity assay utilizes 0.3 M PCA (perchloric acid) and malachite green reagent (8.27 mM sodium molybdate II, 0.33 mM malachite green oxalate, and 0.8 mM Triton X-1 00). To perform the assay. 10 μL of the reaction mixture is quenched in 90 μL of cold 0.3 M PCA. Phosphate standards are used so data can be converted to mM inorganic phosphate released. When all reactions and standards have been quenched in PCA. 100 μL of malachite green reagent is added to the relevant wells in e.g., a microtiter plate. The mixture is developed for 10-15 minutes and the plate is read at an absorbance of 650 nm. If phosphate standards were used, absorbance readings can be converted to mM $P_i$ and plotted over time. Additionally, ATPase assays known in the art include the luciferase assay.

ATPase activity of kinesin motor domains also can be used to monitor the effects of agents and are well known to those skilled in the art. In one embodiment ATPase assays of kinesin are performed in the absence of microtubules. In another embodiment, the ATPase assays are performed in the presence of microtubules; Different types of agents can be detected in the above assays. In a preferred embodiment, the effect of a agent is independent of the concentration of microtubules and ATP. In another embodiment, the effect of the agents on kinesin ATPase can be decreased by increasing the concentrations of ATP, microtubules or both. In yet another embodiment, the effect of the agent is increased by increasing concentrations of ATP, microtubules or both.

Compounds that inhibit the biochemical activity of KSP in vitro may then be screened in vivo. In vivo screening methods include assays of cell cycle distribution, cell viability, or the presence, morphology, activity, distribution, or number of mitotic spindles. Methods for monitoring cell cycle distribution of a cell population, for example, by flow cytometry, are well known to those skilled in the art, as are methods for determining cell viability. See for example, U.S. Pat. No. 6,437,115, hereby incorporated by reference in its entirety. Microscopic methods for monitoring spindle formation and malformation are well known to those of skill in the art (see, e.g., Whitehead and Rattner (1998). J. Cell Sci. 111:2551-61; Galgio et al, (1996) J. Cell Biol., 135:399-414), each incorporated herein by reference in its entirety.

The compounds of the invention inhibit the KSP kinesin. One measure of inhibition is $IC_{50}$, defined as the concentration of the compound at which the activity of KSP is decreased by fifty percent relative to a control. Preferred compounds have $IC_{50}$'s of less than about 1 mM, with preferred embodiments having $IC_{50}$'s of less than about 100 μM, with more preferred embodiments having $IC_{50}$'s of less than about 10 μM, with particularly preferred embodiments having $IC_{50}$'s of less than about 1 μM, and especially preferred embodiments having $IC_{50}$'s of less than about 100 nM, and with the most preferred embodiments having $IC_{50}$'s of less than about 10 nM. Measurement of $IC_{50}$ is done using an ATPase assay such as described herein.

Another measure of inhibition is $K_i$. For compounds with $IC_{50}$'s less than 1 μM, the $K_i$ or $K_d$ is defined as the dissociation rate constant for the interaction of the compounds described herein with KSP. Preferred compounds have $K_i$'s of less than about 100 μM, with preferred embodiments having $K_i$'s of less than about 10 μM, and particularly preferred embodiments having $K_i$'s of less than about 1 μM and especially preferred embodiments having $K_i$'s of less than about 100 nM, and with the most preferred embodiments having $K_i$'s of less than about 10 nM.

The $K_i$ for a compound is determined from the $IC_{50}$ based on three assumptions and the Michaelis-Menten equation. First, only one compound molecule binds to the enzyme and there is no cooperativity. Second, the concentrations of active enzyme and the compound tested are known (i.e., there are no significant amounts of impurities or inactive forms in the preparations). Third, the enzymatic rate of the enzyme-inhibitor complex is zero. The rate (i.e., compound concentration) data are fitted to the equation:

$$V = V_{max} E_0 \left[ 1 - \frac{(E_0 + I_0 + Kd) - \sqrt{(E_0 + I_0 + Kd)^2 - 4E_0 I_0}}{2E_0} \right]$$

where V is the observed rate, $V_{max}$ is the rate of the free enzyme, $I_0$ is the inhibitor concentration, $E_0$ is the enzyme concentration, and $K_d$ is the dissociation constant of the enzyme-inhibitor complex.

Another measure of inhibition is $GI_{50}$, defined as the concentration of the compound that results in a decrease in the rate of cell growth by fifty percent. Preferred compounds have $GI_{50}$'s of less than about 1 mM; those having a $GI_{50}$ of less than about 20 μM are more preferred; those having a $GI_{50}$ of less than about 10 ΞM more so; those having a $GI_{50}$ of less than about 1 μM more so; those having a $GI_{50}$ of less than about 100 nM more so; and those having a $GI_{50}$ of less than about 10 nM even more so. Measurement of $GI_{50}$ is done using a cell proliferation assay such as described herein. Compounds of this class were found to inhibit cell proliferation.

In vitro potency of small molecule inhibitors is determined, for example, by assaying human ovarian cancer cells (SKOV3) for viability following a 72-hour exposure to a 9-point dilution series of compound. Cell viability is determined by measuring the absorbance of formazon, a product formed by the bioreduction of MTS/PMS, a commercially available reagent. Each point on the dose-response curve is calculated as a percent of untreated control cells at 72 hours minus background absorption (complete cell kill).

Anti-proliferative compounds that have been successfully applied in the clinic to treatment of cancel (cancer chemotherapeutics) have $GI_{50}$'s that vary greatly. For example, in A549 cells, paclitaxel $GI_{50}$ is 4 nM, doxorubicin is 63 nM, 5-fluorouracil is 1 μM, and hydroxyurea is 500 μM (data provided by National Cancer Institute, Developmental Therapeutic Program, http://dtp.nci.nih.gov/). Therefore, compounds that inhibit cellular proliferation, irrespective of the concentration demonstrating inhibition, may be useful.

To employ the compounds of the invention in a method or screening for compounds that bind to KSP kinesin, the KSP is bound to a support, and a compound of the invention is added to the assay. Alternatively, the compound of the invention is bound to the support and KSP is added. Classes of compounds among which novel binding agents may be sought include specific antibodies, non-natural binding agents identified in screens of chemical libraries, peptide analogs, etc. Of particular interest are screening assays for candidate agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the compound of the invention to KSP nay be done in a number of ways. In a preferred embodiment, the compound is labeled, for example, with a fluorescent or radioactive moiety, and binding is determined directly. For example, this may be done by attaching all or a portion of KSP to a solid support, adding a labeled test compound (for example a compound of the invention in which at least one atom has been replaced by a detectable isotope), washing off excess reagent, and determining whether the amount of the label is that present on the solid support.

By "labeled" herein is meant that the compound is either directly or indirectly labeled with a label which provides a detectable signal, e.g., radioisotope, fluorescent tag, enzyme, antibodies, particles such as magnetic particles, chemiluminescent tag, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, the kinesin proteins may be labeled at tyrosine positions using $^{125}$I, or with fluorophores. Alternatively, more than one component may be labeled with different labels: $^{125}$I for the proteins, for example, and a fluorophor for the antimitotic agents.

The compounds of the invention may also be used as competitors to screen for additional drug candidates. "Candidate agent" or "drug candidate" or grammatical equivalents as used herein describe any molecule e.g., protein, oligopeptide, small organic molecule, polysaccharide, polynucleotide, etc., to be tested for bioactivity. They may be capable of directly or indirectly altering the cellular proliferation phenotype or the expression of a cellular proliferation sequence, including, both nucleic acid sequences and protein sequences. In other cases, alteration of cellular proliferation protein binding and/or activity is screened. Screens of this sort may be performed either in the presence or absence of microtubules. In the case where protein binding or activity is screened, preferred embodiments exclude molecules already known to bind to that particular protein, for example, polymer structures such as microtubules, and energy sources such as ATP. Preferred embodiments of assays herein include candidate agents which do not bind the cellular proliferation protein in its endogenous native state termed herein as "exogenous" agents. In another preferred embodiment, exogenous agents further exclude antibodies to KSP.

Candidate agents can encompass numerous chemical classes, through typically they are organic molecules, preferably small organic compounds having molecular weight of more than 100 and less than about 2,500 daltons. Candidate agents comprise functional groups necessary for structural interaction with proteins, particularly hydrogen bonding and lipophilic binding, and typically include at least an amine, carbonyl, hydroxyl, ether, or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical physical and biochemical means. Known pharmacological agents may be subjected to directed or random chemical modifications, such as acylation, alkylation, esterification, and/or amidification to produce structural analogs.

Competitive screening assays may be done by combining KSP and a drug candidate in a first sample. A second sample comprises a compound of the present invention. KSP and a drug candidate. This may be performed in either the presence or absence of microtubules. The binding of the drug candidate is determined for both samples, and a change, or difference in binding between the two samples indicates the presence of a drug candidate capable of binding to KSP and potentially inhibiting its activity. That is, if the binding of the drug candidate is different in the second sample relative to the first sample, the drug candidate is capable of binding to KSP.

In a preferred embodiment, the binding of the candidate agent to KSP is determined through the use of competitive binding assays. In this embodiment, the competitor is a binding moiety known to bind to KSP, such as an antibody, peptide, binding partner, ligand, etc. Under certain circumstances, there may be competitive binding as between the candidate agent and the binding moiety, with the binding moiety displacing the candidate agent.

In one embodiment, the candidate agent is labeled. Either the candidate agent, or the competitor, or both, is added first to KSP for a time sufficient to allow binding, if present. Incubations may be performed at any temperature which facilitates optimal activity, typically between 4 and 40° C. Incubation periods are selected for optimum activity, but may also be optimized to facilitate rapid high throughput screening. Typically between 0.1 and 1 hour will be sufficient. Excess reagent is generally removed or washed away. The second component is then added, and the presence or absence of the labeled component is followed, to indicate binding.

In a preferred embodiment, the competitor is added first, followed by the candidate agent. Displacement of the competitor is an indication the candidate agent is binding to KSP and thus is capable of binding to, and potentially inhibiting, the activity of KSP. In this embodiment, either component can be labeled. Thus, for example, if the competitor is labeled, the presence of label in the wash solution indicates displacement by the agent. Alternatively, if the candidate agent is labeled, the presence of the label on the support indicates displacement.

In an alternative embodiment, the candidate agent is added first, with incubation and washing, followed by the competitor. The absence of binding by the competitor may indicate the candidate agent is bound to KSP with a higher affinity. Thus, if the candidate agent is labeled, the presence of the label on the support, coupled with a lack of competitor binding, may indicate the candidate agent is capable of binding to KSP.

Inhibition is tested by screening for candidate agents capable of inhibiting the activity of KSP comprising the steps of combining a candidate agent with KSP, as above, and determining an alteration in the biological activity of KSP. Thus, in this embodiment, the candidate agent should both bind to KSP (although this may not be necessary), and alter its biological or biochemical activity as defined herein. The methods include both in vitro screening methods and in vivo screening (of cells for alterations in cell cycle distribution, cell viability, or for the presence, morphology, activity, distribution, or amount of mitotic spindles, as are generally outlined above.

Alternatively, differential screening may be used to identify drug candidates that bind to the native KSP, but cannot bind to modified KSP.

Positive controls and negative controls may be used in the assays. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g., albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

Administration

Accordingly, the compounds of the invention are administered to cells. By "cells" herein is meant any cell in which mitosis or meiosis can be altered. By "administered" herein is meant administration of a therapeutically effective dose of a compound of the invention to a cell either in cell culture or in a patient. By "therapeutically effective dose" herein is meant a dose that produces the effects for which it is administered. The exact dose will depend on the purpose of the treatment, and will be ascertainable by one skilled in the art using known techniques. As is known in the art, adjustments for systemic versus localized delivery, route of administration, age, body weight, general health, sex, diet, time of administration, nature of the formulation, drug interaction, and the precise condition requiring treatment and its severity may be necessary, and will be ascertainable with routine experimentation by those skilled in the art. However, an effective amount of a compound of Formula I for the treatment of neoplastic growth (typically by intravenous administration), for example colon or breast carcinoma, will generally be in the range of 0.1 to 100 (including 1 to 100) mg/m$^2$ of surface area of the recipient per dose on a once a week to once a month schedule and usually in the range of 2 to 30 mg/m$^2$ of surface area of the recipient per dose on a once a week to once a month schedule. An effective amount of a salt, solvate, or solvate of a salt of a compound of Formula I may be determined as a proportion of the effective amount of the compound of Formula I per se. It is envisaged that similar dosages would be appropriate for treatment of the other conditions referred to herein.

A "patient" for the purposes of the present invention includes both humans and other animals, particularly mammals, and other organisms. Thus the methods are applicable to both human therapy and veterinary applications. In the preferred embodiment the patient is a mammal, and in the most preferred embodiment the patient is human.

Compounds of the invention having the desired pharmacological activity may be administered, preferably as a pharmaceutically acceptable composition comprising all pharmaceutical excipient, to a patient, as described herein. Depending upon the manner of introduction, the compounds may be formulated in a variety of ways as discussed below. The concentration of therapeutically active compound in the formulation may vary from about 0.1-100 wt. %.

The agents may be administered alone or in combination with other treatments, i.e., radiation, or other chemotherapeutic agents such as the taxane class of agents that appear to act on microtubule formation or the camptothecin class of topoisomerase I inhibitors. When used, other chemotherapeutic agents may be administered before, concurrently, or after administration of a compound of the present invention. In one aspect of the invention, a compound of the present invention is co-administered with one or more other chemotherapeutic agents. By "co-administer" it is meant that the present compounds are administered to a patient such that the present compounds as well as the co-administered compound may be found in the patient's bloodstream at the same time, regardless when the compounds are actually administered, including simultaneously.

The administration of the compounds and compositions of the present invention can be done in a variety of ways, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds and inflammation, the compound or composition may be directly applied as a solution or spray.

Pharmaceutical dosage forms include a compound of formula I or a pharmaceutically acceptable salt or solvate thereof, and one or more pharmaceutical excipients. As is known in the art, pharmaceutical excipients are secondary ingredients which function to enable or enhance the delivery of a drug or medicine in a variety of dosage forms (e.g.: oral forms such as tablets, capsules, and liquids; topical forms such as dermal, opthalmic, and otic forms, suppositories; injectables; respiratory forms and the like). Pharmaceutical excipients include inert or inactive ingredients, synergists or chemicals that substantively contribute to the medicinal effects of the active ingredient. For example, pharmaceutical excipients may function to improve flow characteristics, product uniformity, stability, taste, or appearance, to ease handling and administration of dose, for convenience of use, or to control bioavailability. While pharmaceutical excipients are commonly described as being inert or inactive, it is appreciated in the art that there is a relationship between the properties of the pharmaceutical excipients and the dosage forms containing them.

Pharmaceutical excipients suitable for use as carriers or diluents are well known in the art, and may be used in a variety of formulations. See, e.g., Remington's Pharmaceutical Sciences, 18th Edition, A. R. Gennaro, Editor, Mack Publishing Company (1990); Remington: The Science and Practice of Pharmacy, 20th Edition, A. R. Gennaro, Editor, Lippincott Williams & Wilkins (2000); Handbook of Pharmaceutical Excipients, 3rd Edition, A. 1. Kibbe, Editor, American Pharmaceutical Association, and Pharmaceutical Press (2000); and Handbook of Pharmaceutical Additives, compiled by Michael and Irene Ash, Gower (1995), each of which is incorporated herein by reference for all purposes.

Oral solid dosage forms such as tablets will typically comprise one or more pharmaceutical excipients, which may for example help impart satisfactory processing and compression characteristics, or provide additional desirable physical characteristics to the tablet. Such pharmaceutical excipients may be selected from diluents, binders, glidants, lubricants, disintegrants, colors, flavors, sweetening agents, polymers, waxes or other solubility-retarding materials.

Compositions for intravenous administration will generally comprise intravenous fluids, i.e. sterile solutions of simple chemicals such as sugars, amino acids or electrolytes, which can be easily carried by the circulatory system and assimilated. Such fluids are prepared with water for injection USP.

Fluids used commonly for intravenous (IV) use are disclosed in Remington, the Science and Practice of Pharmacy [full citation previously provided], and include:
  alcohol (e.g., in dextrose and water ("D/W") [e.g., 5% dextrose] or dextrose and water [e.g., 5% dextrose] in normal saline solution ("NSS"); e.g. 5% alcohol);
  synthetic amino acid such as Aminiosyn, FreAmine, Travasol, e.g., 3.5 or 7; 8.5; 3.5, 5.5 or 8.5% respectively;
  ammonium chloride e.g., 2.14%;
  dextran 40, in NSS e.g., 10% or in D5/W e.g., 10%;
  dextran 70, in NSS e.g., 6% or in D5/W e.g. 6%;
  dextrose (glucose, D5/W) e.g., 2.5-50%;
  dextrose and sodium chloride e.g., 5-20% dextrose and 0.22-0.9% NaCl;
  lactated Ringer's (Hartmann's) e.g., NaCl 0.6%, KCl 0.03%, $CaCl_2$ 0.02%;
  lactate 0.3%;
  mannitol e.g., 5%, optionally in combination with dextrose e.g., 10% or NaCl e.g., 15 or 20%;
  multiple electrolyte solutions with varying combinations of electrolytes, dextrose, fructose, invert sugar Ringer's e.g., NaCl 0.86%, KCl 0.03%. $CaCl_2$ 0.033%;
  sodium bicarbonate e.g., 5%;
  sodium chloride e.g., 0.45, 0.9, 3, or 5%;
  sodium lactate e.g., 1/6 M; and
  sterile water for injection The pH of such fluids may vary, and will typically be from 3.5 to 8 such as known in the art.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All publications, including but not limited to patents and patent applications, cited in this specification are herein incorporated by reference as if each individual publication were specifically and individually indicated to be incorporated by reference herein as though fully set forth.

EXAMPLES

All anhydrous solvents were purchased from Aldrich Chemical Company in SureSeal® containers. Reagents were added and aqueous extractions performed with single or multichannel pipettors. Filtrations were performed using Whatman/Polyfiltronics 24 well, 10 mL filtration blocks. Evaporation of volatile materials from the array was performed with a Labconco Vortex-Evaporator or by sweeping with a 4×6 nitrogen manifold.

Example 1

Synthesis of Compound

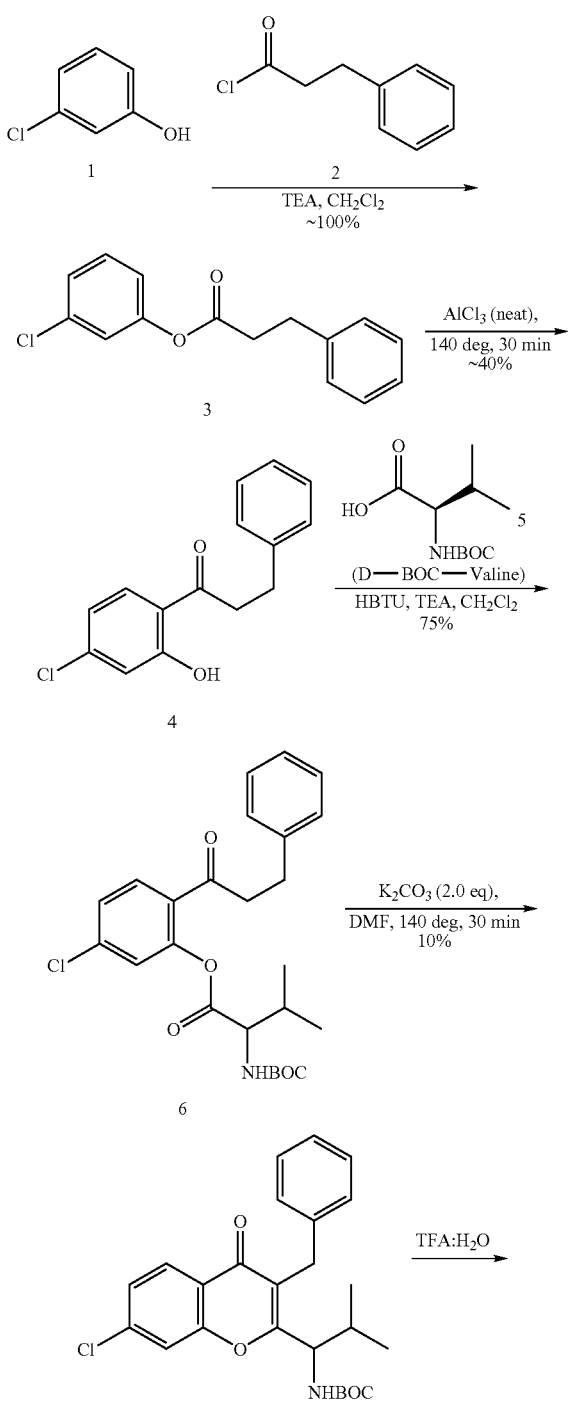

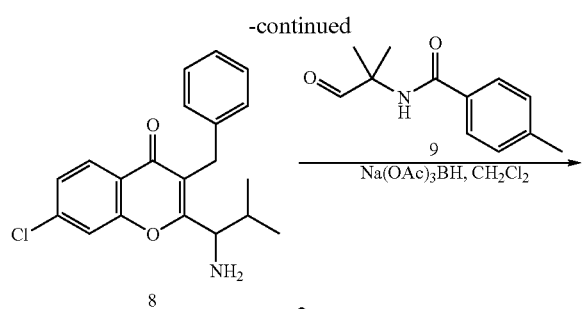

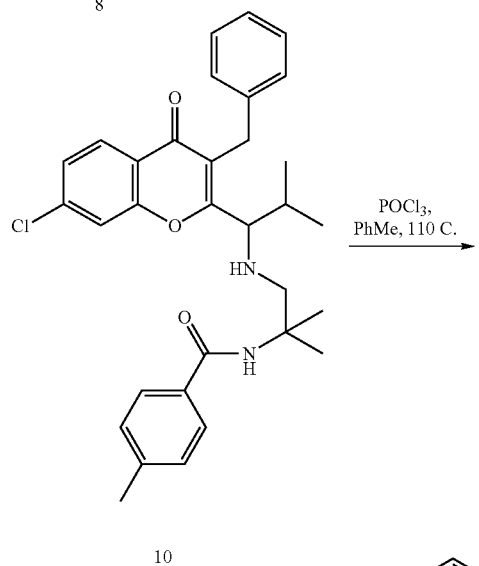

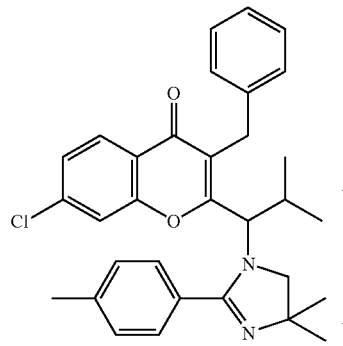

a) 3-Phenyl-propionic acid 3-chloro-phenyl ester

To a solution of 3-chlorophenol (1, 50.1 g, 0.3 mol) triethylamine (TEA, 85 mL), and CH$_2$Cl$_2$ (500 mL) at 23° C. was added hydrocinnamoyl chloride (2, 31 mL, 0.3 mol) over 5 minutes. After 30 minutes, the reaction mixture was concentrated in vacuo. The crude slurry was then dissolved in 10:1 hexanes:EtOAc (300 mL) and washed with 1 N NaOH (100 mL) and brine (100 mL). The organic layer was dried (MgSO$_4$) and filtered through a plug of silica gel (10:1 hexanes:EtOAc rinse). The eluent was concentrated to afford 78 g of a slightly yellow oil, which was used without any further purification.

b) 1-(4-Chloro-2-hydroxy-phenyl)-3-phenyl-propan-1-one

AlCl$_3$ (52 g, 0.39 mol) was added slowly over 15 minutes to ester 3 (78 g, 0.3 mol) at 140° C. After an additional 15 minutes gas evolution ceased and the reaction mixture was poured into a 1 L beaker and allowed to cool to RT. The resulting solid was dissolved in CH$_2$Cl$_2$ (100 mL) and slowly quenched with 1 N HCl (200 mL). This mixture was diluted with EtOAc (600 mL) and the layers were separated. The organic layer was washed with brine (100 mL), dried (MgSO$_4$), filtered, and concentrated. The crude oil was dissolved in 20:1 hexanes:EtOAc (500 mL) and flushed through a plug of silica gel (100% hexanes: 20:1 hexanes:EtOAc rinse). The filtrate was concentrated to provide a slightly brown oil, which was purified by flash column chromatography (50:1 hexanes:EtOAc; 40:1 hexanes:EtOAc; 30:1 hexanes:EtOAc; 20:1 hexanes:EtOAc) to yield 31.2 g (40%) of 4 as a white solid.

c) 2-tert-Butoxycarbonylamino-3-methyl-butyric acid 5-chloro-2-(3-phenyl-propionyl)-phenyl ester A solution of phenol 4 (23.18 g, 89.1 mmol), BOC-D-Valine (5, 21.29 g 98.05 mmol), HBTU (40.57 g, 107 mmol). TEA (37 mL, 265 mmol), and CH$_2$Cl$_2$ (155 mL) were maintained at 23° C. for 5 hours. The reaction mixture was diluted with EtOAc (500 mL) and washed with saturated aqueous NH$_4$Cl (2×100 mL) and brine (100 mL). The organic layer was dried (MgSO$_4$), filtered, and concentrated. The resulting residue was purified by flash column chromatography (100% hexanes: 50:1 hexanes:EtOAc: 40:1 hexanes:EtOAc: 30:1 hexanes:EtOAc: 20:1 hexanes:EtOAc: 10:1 hexanes:EtOAc) to yield 35.7 (87%) of 6 as a yellow oil.

d) [1-(3-Benzyl-7-chloro-4-oxo-4H-chromen-2-yl)-2-methyl-propyl]-carbamic acid tert-butyl ester A mixture of ester 6 (35.55 g, 79.17 mmol), K$_2$CO$_3$ (21.8 g, 158.4 mmol), and DMF (264 mL) was placed into a 140° C. oil bath. After 30 mins, the reaction mixture was quenched with H$_2$O (300 mL) and extracted with Et$_2$O (3×200 mL). The organic layer was washed with brine (100 mL), dried (MgSO$_4$), filtered, and concentrated. The resulting residue was purified by flash column chromatography (10:1 hexanes:EtOAc) to yield 3.5 g (10.2%) of 7.

e) 2-(1-Amino-2-methyl-propyl)-3-benzyl-7-chloro-chromen-4-one

Chromenone 7 (1.8 g, 4.18 mmol) and TFA:H$_2$O (97.5:2.5, 30 mL) was maintained at 23° C. for 1 h. The reaction mixture was concentrated. The residue was dissolved in EtOAc (100 mL) and washed with 1 N NaOH (25 mL) and brine (25 mL). The organic layer was dried (MgSO$_4$), filtered., and concentrated to provide a colorless oil, which was used without further purification.

f) N-{-2-[1-(3-Benzyl-7-chloro-4-oxo-4H-chromen-2-yl)-2-methyl-propylamino]-1,1-dimethyl-ethyl}-4-methyl-benzamide Chromenone 8 (72 mg, 0.22 mmol), aldehyde 9 (65 mg, 0.32 mmol). Na(OAc)$_3$BH (184 mg, 0.87 mmol), and CH$_2$Cl$_2$ (1 mL) was maintained at 23° C. for 3 h. The reaction mixture was diluted with EtOAc (20 mL) and washed with 1 N NaOH (5 mL) and brine (5 mL). The organic layer was dried (MgSO$_4$), filtered, and concentrated. The resulting residue was purified by flash column chromatography (3:1 hexanes: EtOAc) to yield 0.80 mg (70%) of 10 as a white solid.

g) 3-Benzyl-7-chloro-2-[1-(4,4-dimethyl-2-p-tolyl-4, 5-dihydro-imidazol-1-yl)-2-methyl-propyl]-chromen-4-one Chromenone 10 (80 mg 0.15 mmol), POCl$_3$ (0.1 mL, 1.1 mmol), and PhMe (1 mL) were heated to 110° C. After 3.5 h. an additional portion of POCl$_3$ (0.1 mL, 1.1 mmol) was added. After 1 h, the reaction mixture was diluted with EtOAc (20 mL) and washed with 1 N NaOH (10 mL) and brine (10 mL). The organic layer was dried (MgSO$_4$), filtered, and concentrated. The resulting residue was purified by flash column chromatography (20:1 CHCl$_3$:MeOH) to yield 50 mg (65%) of 11 as a white solid.

Example 2

Synthesis of Compounds

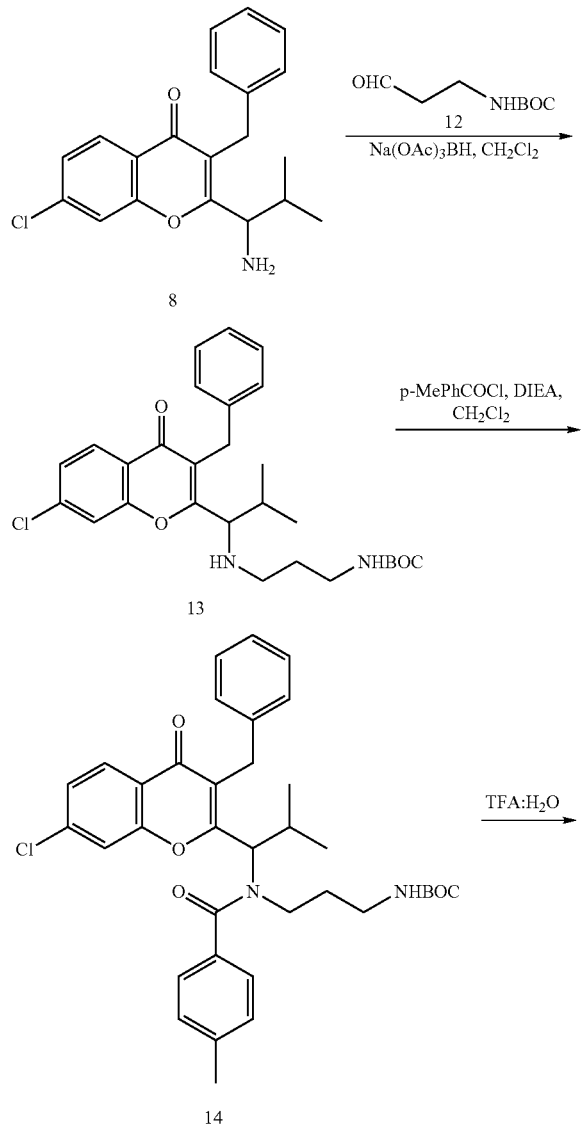

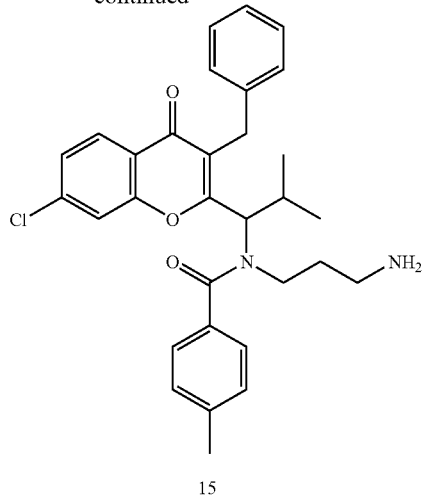

15 a) Preparation of {3-[1-(3-Benzyl-7-chloro-4-oxo-4H-chromen-2-yl)-2-methyl-propylamino]-propyl}-carbamic acid tert-butyl ester Chromenone 8 (420 mg, 1.24 mmol), aldehyde 12 (280 mg, 1.6 mmol). NaCN(OAc)$_3$BH (790 mg, 3.7 mmol), and CH$_2$Cl$_2$ (4.1 mL) was maintained at 23°(0 for 3 h. The reaction mixture was diluted with EtOAc (20 mL) and washed with 1 N NaOH (5 mL) and brine (5 mL). The organic layer was dried (MgSO$_4$), filtered, and concentrated. The resulting residue was purified by flash column chromatography (5:1 hexanes:EtOAc: 3:1 hexanes:EtOAc) to yield 460 mg (75%) of 13 as a viscous oil.

b) Preparation of {3-[[1-(3-Benzyl-7-chloro-4-oxo-4H-chromen-2-yl)-2-methyl-propyl]-(4-methyl-benzoyl)-amino]-propyl}-carbamic acid tert-butyl ester To a solution of chromenone 13 (1.3 g 2.6 mmol), diisoproylethylamine (DIEA, 1.8 mL), and CH$_2$Cl$_2$ (7.5 mL) at 23° C. was added p-toluoyl chloride (0.7 mL, 5.22 mmol). After 2.5 h. the reaction mixture was diluted with EtOAc (100 mL) and washed with saturated aqueous NaHCO$_3$ (2×20 mL) and brine (20 mL). The organic layer was dried (MgSO$_4$), filtered, and concentrated. The resulting residue was purified by flash column chromatography (3:1 hexanes:EtOAc) to yield 1.43 g (89%) of 14 as a colorless oil.

c) Preparation of N-(3-Amino-propyl)-N-[1-(3-benzyl-7-chloro-4-oxo-4H-chromen-2-yl)-2-methyl-propyl]-4-methyl-benzamide Chromenone 14 (1.43 g, 2.32 mmol) and TFA:H$_2$O (97.5: 2.5, 30 mL) was maintained at 23° C. for 1 h. The reaction mixture was concentrated. The residue was dissolved in EtOAc (100 mL) and washed with 1 N NaOH (25 mL) and brine (25 mL). The organic layer was dried (MgSO$_4$), filtered, and concentrated to provide a white solid which was deemed >95% pure by $^1$H NMR and LCMS analysis.

Using procedures analogous to those set forth above in Example 2, the following compound was prepared.

| Structure | LRMS (MH) m/z |
|---|---|
| 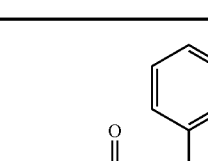 | 471.2 |

Example 3

Synthesis of Compounds

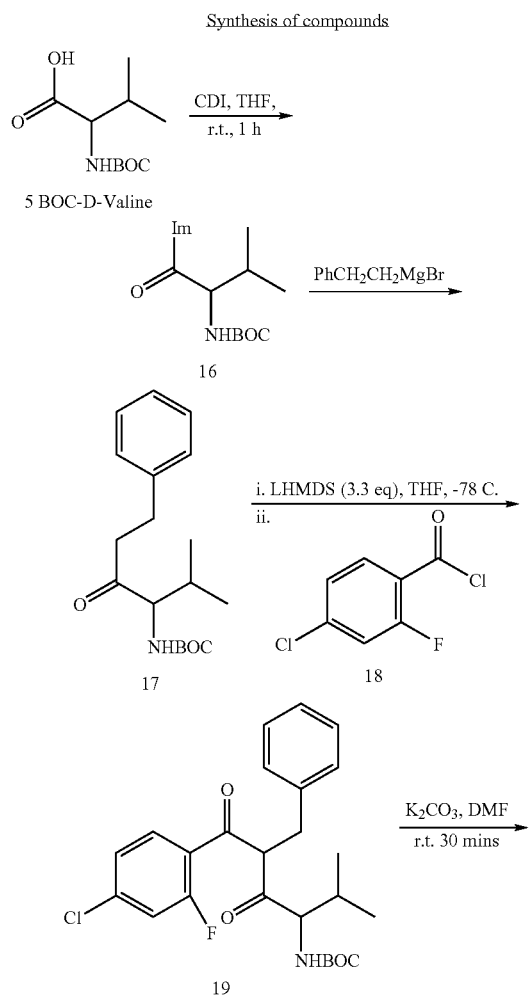

Carbonyldiimidazole (9.14 g, 56.37 mmol) was added slowly to a r.t. solution of BOC-D-Valine (5, 12.25 g, 56.37 mmol) and THF (185 mL). Afer 1 h, the solution was washed with 50% aqueuous NaCl (200 mL), followed by brine (2×200 mL). The organic layer was dried (MgSO$_4$), filtered, and concentrated to provide a white solid, which was used without further purification.

(2-Bromoethyl)benzene (2.51 mL, 18.38 mmol), magnesium turnings (477 mg, 19.62 mmol), and THF (20 mL) were heated to 60° C. for 1 hour, then allowed to cool to r.t. A solution of 16 (2.0 g 9.19 mmol) and THF (20 mL) was cooled to 0-5° C. The solution of the phenethyl magnesium chloride was then added via syringe to the 0-5° C. Solution of the valine imidazole. The temperature was monitored by internal thermometer and as not allowed to exceed 15° C. The reaction mixture was maintained at 0-5° C. for 1 hour. The reaction mixture was quenched with saturated aqueous NH$_4$Cl (20 mL), and diluted with EtOAc (100 mL). The layers were separated and the organic layer was washed with brine (30 mL). The organic layer was dried (MgSO$_4$), filtered, and concentrated. The resulting residue was purified by flash column chromatography (10:1 hexanes:EtOAc: 5:1 hexanes:EtOAc) to yield 1.15 (41%) of 17. LRMS (MH-tBuOCO) m/z 206.1.

LHMDS (1,M in THF, 9.53 mL, 3.3 equiv) was added slowly via syringe to a −78° C. solution of ketone 17 (882 mg, 2.89 mmol). After the addition was complete the resulting light orange solution was maintained at −78° C. for 40 mins. Neat 4-chloro-2-fluorobenzoyl chloride (18, 460 µL, 2.89 mmol) (assumed density to be 1.20 g/mL) was added dropwise via syringe. The reaction solution turned to an orange color and was maintained for 40 mins. The reaction solution was quenched with saturated aqueous NH$_4$Cl (20 mL), and diluted with EtOAc (50 mL). The layers were separated and the organic layer was washed with brine (30 mL). The organic layer was dried (MgSO$_4$), filtered, and concentrated. The resulting residue was purified by flash column chromatography (10:1 hexanes:EtOAc) to yield 1.15 g (86%) of 19. LRMS (MH-HF) m/z 442.1.

A mixture of 19 (1.15 g, 2.49 mmol), K$_2$CO$_3$ (420 mg, 3.04 mmol), and DMF (12 mL) was maintained at r.t. for 30 mins. The yellow reaction solution was quenched with brine (50 mL), and diluted with Et$_2$O (50 mL). The layers were separated and the organic layer was washed with brine (2×50 mL). The organic layer was dried (MgSO$_4$), filtered, and concentrated. The resulting residue was purified by flash column chromatography (10:1 hexanes:EtOAc) to yield 20. LRMS (MH) m/z 442.1.

Using methods analogous to those described above in Examples 2 and 3, the compounds shown below were prepared.

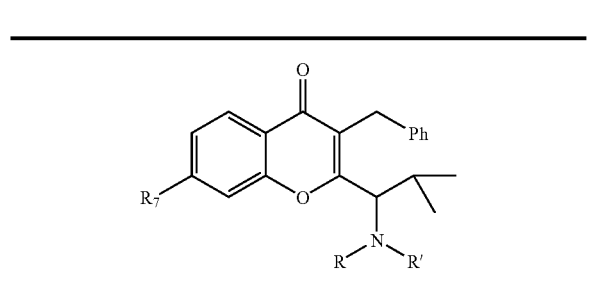

| R$_7$ | R | R' | Stereochemistry (R/S) |
|---|---|---|---|
| Cl | H | H | 3/1 |
| Cl | —CH$_2$CMe$_2$N═C(p-tol)- | | 3/1 |
| Cl | H$_2$N(CH$_2$)$_3$— | p-toluoyl | 3/1 |
| Cl | H$_2$N(CH$_2$)$_3$— | MeOCH$_2$C(O)– | 3/1 |
| Cl | H$_2$N(CH$_2$)$_3$— | p-Br-phenyl- | 3/1 |
| Cl | H$_2$N(CH$_2$)$_3$— | p-toluoyl | R |
| Cl | H$_2$N(CH$_2$)$_3$— | p-toluoyl | S |
| Cl | —CH$_2$CMe$_2$N═C(p-tol)- | | R |
| Cl | —CH$_2$CMe$_2$N═C(p-tol)- | | S |
| F | H | H | 3/1 |
| F | H$_2$N(CH$_2$)$_3$— | p-toluoyl | 3/1 |
| F | H$_2$N(CH$_2$)$_3$— | MeOCH$_2$C(O)— | 3/1 |
| F | —CH$_2$CMe$_2$N═C(p-tol)- | | 3/1 |

Example 4

Alternative Methods for Preparation of Compounds

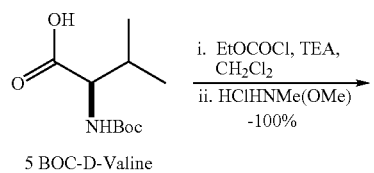

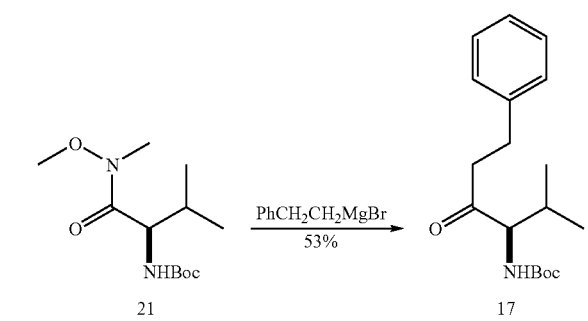

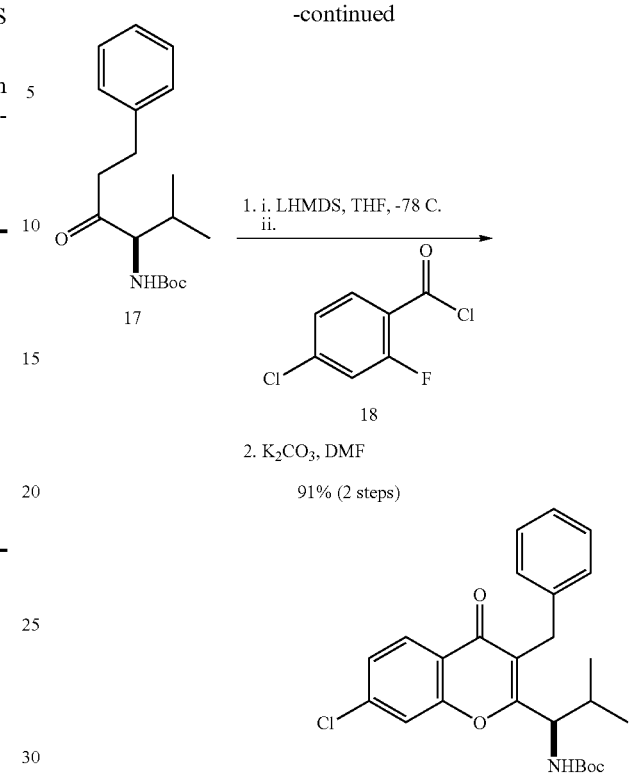

Ethylchloroformate (11.0 mL, 115 mmol) was added over 1 minute to a 0-5° C. solution of BOC-D-Valine (5, 25.0 g, 115 mmol), triethylamine (16.0 mL, 115 mmol), and THF (145 mL) under N$_2$. The internal temperature of the reaction solution rose to 9° C. After 15 mins, a mixture of dimethylhydroxylamine hydrochloride (13.46 g, 138 mmol), triethylamine (32.0 mL, 230 mmol), and THF (110 mL) was added over 5 minutes. The internal temperature rose to 17° C. Upon completion of addition, the ice/H$_2$O bath was removed and the reaction solution maintained at 23° C. for 1 hour. The reaction solution was then concentrated. The crude residue was dissolved in EtOAc (200 mL) and washed with 1 N HCl (200 mL) and brine (100 mL). The organic layer was dried (MgSO$_4$), filtered, and concentrated to provide 30 g (~100%) of 21 as a colorless oil, which was used without further purification.

(2-Bromoethyl)benzene (38.0 mL, 273 mmol), magnesium turnings (7.0 g, 289 mmol), and Et$_2$O (500 mL) were mixed in a 1 L round-bottom flask equipped with a reflux condenser at 23° C. under a N$_2$ atmosphere. After ~10 mins the reaction mixture begins to exotherm and the reaction mixture was allowed to progress to reflux with intermittent cooling with an ice/H$_2$O bath. After 1.5 hour, the Grignard reaction was complete and the solution had cooled to 23° C. A solution of 21 (18.0 g, 82.7 mmol) and Et$_2$O (200 mL) was added via cannula to the 20° C. solution of the phenylethylmagnesium bromide. The temperature was monitored by internal thermometer and vas not allowed to exceed ~30° C. The reaction mixture temperature was monitored by an internal thermometer and regulated (20-30° C.) with an ice/H$_2$O bath. After 1 h at 23° C., the reaction mixture was quenched by pouring into 1 N HCl (300 mL). The layers were separated and the organic layer was washed with brine (100 mL). The organic layer was dried (MgSO$_4$), filtered, and concentrated. The resulting residue was purified by flash column chromatography (10:1 hexanes:EtOAc) to yield 13.4 g (53%) of 17. LRMS (MH-tBuOCO) m/z 206.1.

Lithium bis(trimethylsilyl)amide (LHMDS, 1.0 M in THF, 94.0 mL, 3.3 equiv) was added slowly over ~3 minutes via syringe to a −78° C. solution of ketone 17 (8.74 g, 28.62 mmol) and THF (100 mL). The reaction solution temperature was monitored by an internal thermometer, and addition of the base was done at a rate sufficient to prevent the temperature from exceeding −54° C. After the addition was complete the resulting solution was maintained at −78° C. for 30 mins. Neat 4-chloro-2-fluorobenzoyl chloride (18, 4.58 mL, 28.62 mmol) (assumed density to be 1.20 g/mL) was added dropwise over ~1 minute via syringe (temperature rose from −78° C. to −59° C.). The reaction solution was maintained at −78° C. for 30 mins. The reaction solution was quenched with 1 N HCl (100 mL). The layers were separated and the organic layer was washed with brine (100 mL). The organic layer was dried (MgSO$_4$), filtered, and concentrated. The resulting residue was used without further purification.

A mixture of the above crude product, K$_2$CO$_3$ (4.75 g, 34.34 mmol) and DMF (100 mL) was maintained at 23° C. for 30 mins. The reaction mixture was quenched by addition of Et$_2$O (200 mL) and brine (200 mL). The layers were separated and the organic layer was washed with brine (2×200 mL). The organic layer was dried (MgSO$_4$), filtered, and concentrated. The resulting residue absorbed onto silica gel (CH$_2$Cl$_2$) and was purified by flash column chromatography (10:1 hexanes: EtOAc) to yield 11.5 g (91% for 2 steps) of 20 as a white solid. LRMS (MH) m/z 442.1.

Example 5

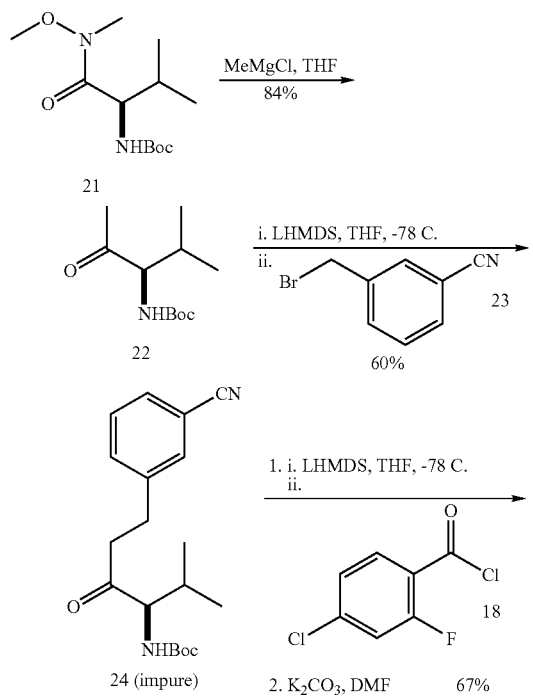

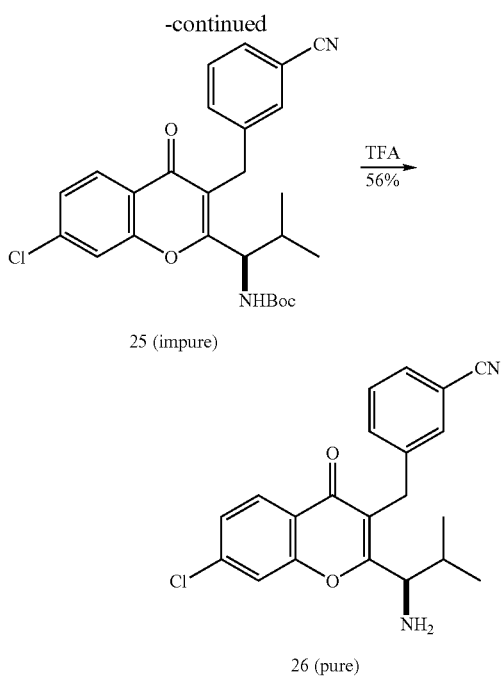

Methylmagnesium chloride (82.5 mL, 3.0 M in THF, 247 mmol) was added over 5 mins to a 0-5° C. solution of 21 (17.95 g, 69.0 mmol) and THF (200 mL) under an N$_2$ atmosphere. The reaction mixture temperature was monitored by an internal thermometer, and addition of the Grignard was done at a rate sufficient to prevent the temperature from exceeding 19° C.; Upon complete addition the cooling bath was removed and the reaction mixture was maintained at 23° C. for 2 hours. The reaction mixture was then quenched with 1 N HCl (100 mL). The layers were separated and the organic layer was washed with brine (100 mL). The organic layer was dried (MgSO$_4$), filtered, and concentrated to provide 12.5 g (84%) of 22 as a white solid (>95% pure by $^1$H NMR), which was used without further purification.

LHMDS (128 mL, 1.0 M in THF) was added via syringe over 3 minutes to a −78° C. solution of ketone 22 (12.5 g, 58.1 mmol) and THF (200 mL). The reaction solution temperature was monitored by an internal thermometer, and addition of the base was done at a rate sufficient to prevent the temperature from exceeding −58° C. After 30 minutes, a solution of α-bromo-m-tolunitrile (23, 12.5 g, 63.9 mmol) and THF (50 mL) was added over 30 seconds (temperature rose from −78 to −60° C.). The cooling bath was immediately replaced by a ice/H$_2$O bath and the reaction solution was maintained at ~0° C. for 20 minutes. The reaction solution was quenched with 1 N HCl (100 mL). The layers were separated and the organic layer was washed with brine (100 mL). The organic layer was dried (MgSO$_4$), filtered, and concentrated. The resulting residue was purified by flash column chromatography) (10:1 hexanes:EtOAc) to yield 11.6 g (60%) of 24. Inspection of the $^1$H NMR revealed that 24 was only ~80% pure, but no further purification was performed. LRMS (MH-tBuOCO) m/z 231.1.

Lithium bis(trimethylsilyl)amide (LHMDS, 1.0 M in THF, 28.4 mL, 3.3 equiv) was added slowly via syringe to a −78° C. solution of ketone 24 (2.84 g, 8.6 mmol) and THF (40 mL). The reaction solution temperature was monitored by an internal thermometer, and addition of the base was done at a rate sufficient to prevent the temperature from exceeding −48° C.

After the addition was complete the resulting solution was maintained at −78° C. for 30 mins. Neat 4-chloro-2-fluorobenzoyl chloride (18, 1.38 mL, 8.6 mmol) (assumed density to be 1.20 g/mL) was added dropwise via syringe. The reaction solution turned to all orange color and was maintained for 30 mins. The reaction solution was quenched with 1 N HCl (20 mL). The layers were separated and the organic layer was washed with brine (20 mL). The organic layer was dried (MgSO$_4$), filtered, and concentrated. The resulting residue was used without further purification.

A mixture of the above crude product, K$_2$CO$_3$ (1.43 g, 10.34 mmol) and DMF (43 mL) was maintained at 23° C. for 1 hour. The reaction mixture was quenched by addition of Et$_2$O (100 mL) and brine (200 mL). The layers were separated and the organic layer was washed with brine (2×200 mL). The organic layer was dried (MgSO$_4$), filtered, and concentrated. The resulting residue absorbed onto silica gel (CH$_2$Cl$_2$) and was purified by flash column chromatography (5:1 hexanes: EtOAc) to yield 2.7 g (67%/For 2 steps) of 25. Inspection of the $^1$H NMR revealed that 25 was only 80% pure, but no further purification was performed. LRMS (MH) m/z 467.1.

Chromenone 25 (2.71 g 5.80 mmol) and TFA:H$_2$O (97.5: 2.5, 25 mL) was, maintained at 23° C. for 1 h. The reaction mixture was concentrated. The residue was dissolved in EtOAc (100 mL) and washed with 1 N NaOH (25 mL) and brine (25 mL). The organic layer was dried (MgSO$_4$), filtered, and concentrated. The resulting residue was purified by flash column chromatography (1:1 hexanes:EtOAc; 1:2 hexanes: EtOAc: 1:4 hexanes:EtOAc) to yield 1.20 g (56%) of 26. LRMS (MH) m/z 367.1.

Example 6

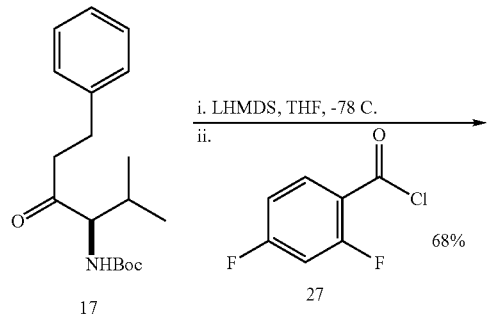

-continued

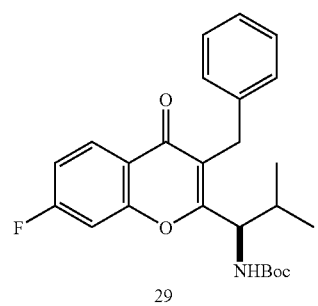

Lithium bis(trimethylsilyl)amide (LHMDS, 1.0 M in THF, 23.5 mL, 3.3 equiv) was added slowly via syringe to a −78° C. solution or ketone 17 (2.18 g, 7.14 mmol) and THF (20 mL). The reaction Solution temperature was monitored by an internal thermometer, and addition of the base was done at a rate sufficient to prevent the temperature from exceeding −50° C. After the addition was complete the resulting solution was maintained at −78° C. for 30 mins. Neat 2,4-difluorobenzoyl chloride (27, 1.05 mL, 8.57 mmol) was added dropwise via syringe. The reaction solution turned to an orange color and was maintained for 30 mins. The reaction Solution was quenched with 1 N HCl (20 mL). The layers were separated and the organic layer was washed with brine (20 mL). The organic layer was dried (MgSO$_4$), filtered, and concentrated. The resulting residue was purified by flash Column chromatography (10:1 hexanes:EtOAc) to yield 2.16 g (68%) of 28. Inspection of the $^1$H NMR revealed that 28 was only ~85% pure, but no further purification was performed.

A mixture of 28 (2.16 g, 4.9 mmol), K$_2$CO$_3$ (812 mg, 5.86 mmol), and DMF (24 mL) was maintained at 23° C. for 1 hour. The reaction mixture was quenched with brine (50 mL), and diluted with Et$_2$O (50 mL). The layers were separated and the organic layer was washed with brine (2×50 mL). The organic layer was dried (MgSO$_4$), filtered, and concentrated. The resulting residue was purified by flash column chromatography (10:1 hexanes:EtOAc) to yield 1.25 g (60%) of 29. LRMS (MH) m/z 426.2.

Example 7

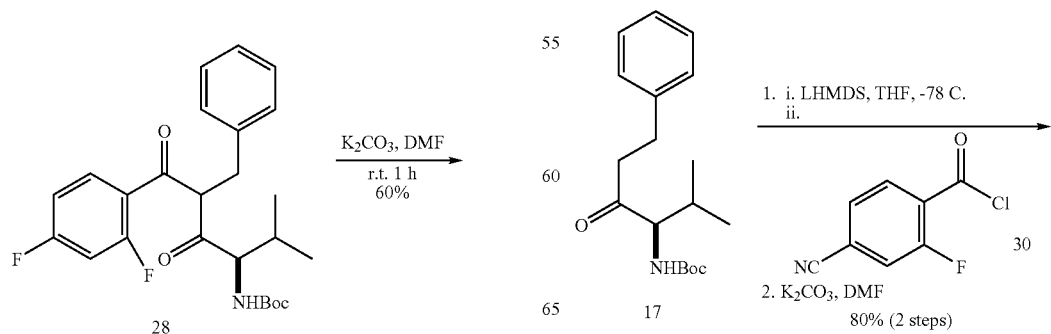

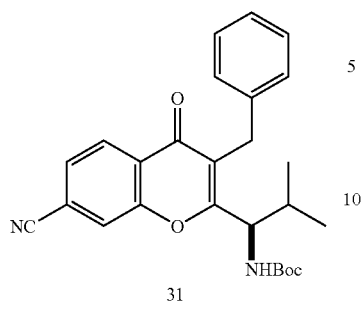

31

Lithium bis(trimethylsilyl)amide (LHMDS, 1.0 M in THF, 47 mL, 3.3 equiv) was added slowly via syringe to a −78° C. solution of ketone 17 (4.37 g, 14.31 mmol) and THF (55 mL). The reaction solution temperature was monitored by an internal thermometer, and addition of the base was done at a rate sufficient to prevent the temperature from exceeding −50° C. After the addition was complete the resulting solution was maintained at −78° C. for 30 mins. A solution of 4-cyano-2-fluorobenzoyl chloride (30, 1.38 mL, 8.6 mmol) and THF (5 mL) was added rapidly via syringe (temperature rose from −78 to 50° C.). The reaction solution turned to a dark red color and was maintained for 30 mins. The reaction solution was quenched with 1 N HCl (20 mL). The layers were separated and the organic layer was washed with brine (20 mL). The organic layer was dried (MgSO$_4$), filtered, and concentrated. The resulting residue was used without further purification.

A mixture of the above crude product, K$_2$CO$_3$ (2.40 g, 17.17 mmol) and DMF (70 mL) was maintained at 23° C. of 1 hour. The reaction mixture was quenched by addition of Et$_2$O (200 mL) and brine (200 mL). The layers were separated and the organic layer was washed with brine (2×200 mL). The organic layer was dried (MgSO$_4$), filtered, and concentrated. The resulting residue was purified by flash column chromatography (10:1 hexanes:EtOAc) to yield 4.95 g (80% for 2 steps) of 31. LRMS (MH) m/z 433.2.

Example 8

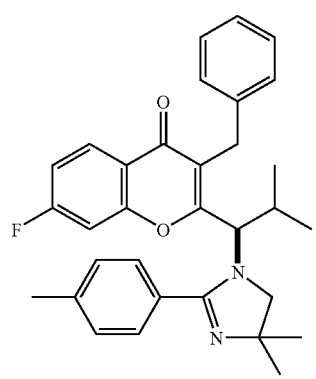

32

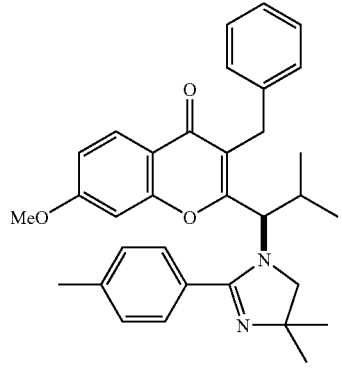

33

7-Fluoro-Chromenone 32 (96 mg, 0.19 mmol) was dissolved in 0.5 M sodium methoxide in methanol (10 mL) and heated to 70° C. The temperature was maintained at 70° C. for 12 hours and then cooled to room temperature. The solvent was removed under reduced pressure. To the remaining residue was added EtOAc (20 mL) and water (20 mL). The layers were separated and the aqueous phase was extracted with additional EtOAc (3×15 mL). The organic phases were combined, washed with brine (25 mL) and dried (Na$_2$SO$_4$). Concentration in vacuo gave an amorphous white solid which was purified using flash column chromatography (20:1 DCM:MeOH) to provide 92 mg (94%) of 33. LRMS (MH) m/z 509.3.

Example 9

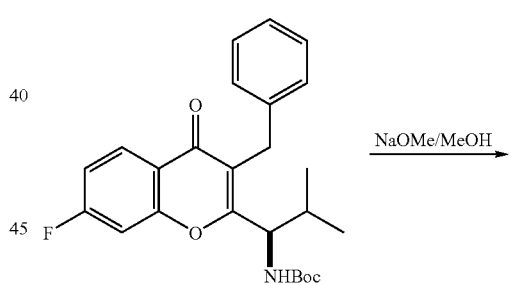

29

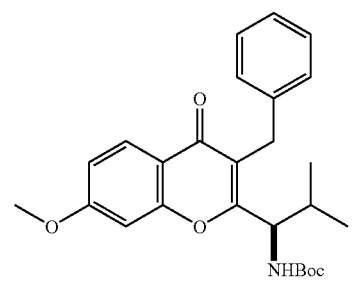

34

Compound 29 (608 mg, 1.43 mmol) was dissolved into a solution of 0.5 M sodium methoxide in methanol (40 mL). The mixture was heated to reflux for 3 hours (or until LC-MS indicated no starting material left). Then the solvent was evaporated. The residue was dissolved in dichloromethane (200 mL) and water (200 mL) was added, in which pH of the mixed solution was adjusted to 9 by adding 2N HCl solution. The collected organic layers were dried by sodium sulfate. After evaporation of solvents, the final compound 34 (580 mg, 92%) was dried under vacuum.

Example 10

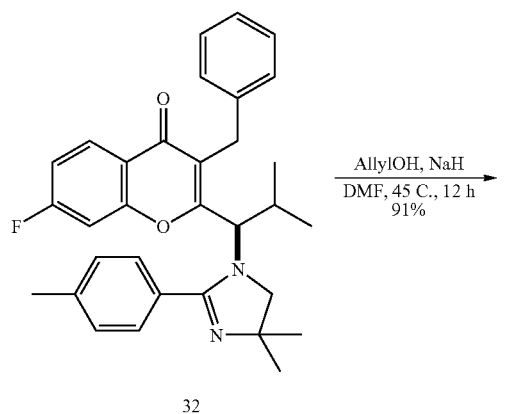

32

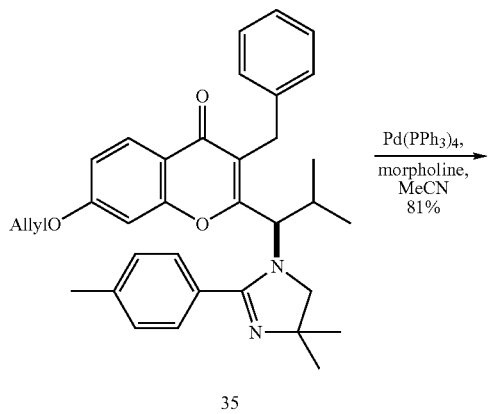

35

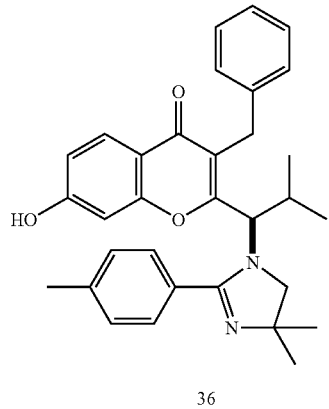

36

To a solution of 32 (56 mg, 0.11 mmol) in DMF (5 mL) was added NaH (5 mg of 60% dispersion in mineral oil, 0.15 mmol). The resulting solution was stirred at 45° C. for 5 mins., then allyl alcohol was added (10 µL, 0.15 mmol) via pipette. The resulting solution was stirred at 45° C. for 12 hours and then cooled to room temperature. EtOAc (50 mL) and water (15 mL) were added and the layers were separated. The aqueous pase was extracted with EtOAc (3×15 mL). The organic phases were combined, washed with water (2×30 mL) and brine (2×30 mL), dried (Na$_2$SO$_4$) and concentrated under reduced pressure to yield 35 as an amorphous solid, which was used without further purification (54 mg, 91%). LRMS (MH) m/z 535.0.

To a room temperature solution of 35 (54 mg, 0.10 mmol) and MeCN (5 mL) was added morpholine (44 µL, 0.50 mmol), followed by Pd(PPh$_3$)$_4$ (5 mg, 10%). The resulting solution was stirred for 5 minutes and then concentrated under reduced pressure. The remaining residue vas purified by flash column chromatography using stepwise elution (20:1 DCM:MeOH, 10:1 DCM:MeOH) to provide 41 mg of 36 as an off-white solid (81%). LRMS (MH) m/z 495.2.

Example 11

Preparation of 3-Benzyl-7-chloro-2-[2-methyl-1-(2-p-tolyl-4,5-dihydro-imidazol-1-yl)-propyl]-chromen-4-one a) {2-[1-(3-Benzyl-7-chloro-4-oxo-4H-chromen-2-yl)-2-methyl-propylamino]-ethyl}-carbamic acid tert-butyl ester To a solution of 2-(1-amino-2-methyl-propyl)-3-benzyl-7-chloro-chromen-4-one (6.0 g, 18 mmol) and (3-oxoethyl) carbamic acid tert-butyl ester (3.6 g, 23 mmol) in methylene chloride (150 mL) was added sodium triacetoxyborohydride (7.4 g, 35 mmol). The reaction mixture was stirred at room temperature for 16 hours, at which time it was diluted with 1 N sodium hydroxide (150 mL) and stirred vigorously for 2 hours. The organic layer was washed with 1 N sodium hydroxide (100 mL) and brine (100 mL), dried over magnesium sulfate, and concentrated. The residue was purified by flash chromatography (0→50% ethyl acetate/hexanes) to give 5.7 g (67%) of the title compound. MS(ES+) m/e 485 [M+H]$^+$.

b) 2-[1-(2-Amino-ethylamino)-2-methyl-propyl]-3-benzyl-7-chloro-chromen-4-one

A solution of {2-[1-(3-benzyl-7-chloro-4-oxo-4H-chromen-2-yl)-2-methyl-propylamino]-ethyl}-carbamic acid tert-butyl ester (5.7 g, 12 mmol) in 4:1 methylene chloride/trifluoroacetic acid (250 mL) was maintained at room temperature for 1.5 hours, at which time it was concentrated. The residue was dissolved in methylene chloride (200 mL), washed with 10% sodium carbonate, saturated sodium bicarbonate, and brine, dried over magnesium sulfate, and concentrated. The residue (4.2 g, 91% yield) was used without further purification.

c) N-{2-[1-(3-Benzyl-7-chloro-4-oxo-4H-chromen-2-yl)-2-methyl-propylamino]-ethyl}-4-methyl-benzamide To a cooled (0° C.) solution of 2-[1-(2-amino-ethylamino)-2-methyl-propyl]-3-benzyl-7-chloro-chromen-4-one (4.1 g, 11 mmol) and triethylamine (2.2 mL, 17 mmol) in methylene chloride (100 mL) was added a solution of p-toluyl chloride (1.7 g 11 mmol) in methylene chloride (20 mL). The reaction was maintained at 0° C. for 2 hours, at which time it as diluted with ether (250 mL). The resultant solution was washed with 1 N hydrogen chloride (2×200 mL), saturated sodium bicarbonate (200 mL) and brine (150 mL), dried over magnesium sulfate, and concentrated. The residue was purified by flash chromatography (0→60% ethyl acetate/hexanes) to (give 2.8 g, (50%) of the title compound. MS(ES+) m/z 503 [M+H]$^+$.

d) 3-Benzyl-7-chloro-2-[2-methyl-1-(2-p-tolyl-4,5-dihydro-imidazol-1-yl)-propyl]-chromen-4-one A mixture of N-{2-[1-(3-benzyl-7-chloro-4-oxo-4H-chromen-2-yl)-2-methyl-propylamino]-ethyl}-4-methyl-benzamide (2.8 g, 5.5 mmol) and phosphorus oxychloride (9.4 mL, 100 mmol) in toluene (60 mL) was heated at 85° C. for 7 hours, then heated at reflux for 1 hour. The reaction was concentrated and the residual phosphorus oxychloride removed by toluene azeotrope. The residue was diluted with ethyl acetate (100 mL) and washed with saturated sodium bicarbonate (100 mL) and brine (100 mL), dried over magnesium sulfate, and concentrated. The resultant residue was purified by flash chromatography (0→8% methanol/methylene chloride) to give 1.4 g (50%) of the title compound. MS(ES+) m/e 485 [M+H]$^+$.

Following procedures analogous to those set forth herein in Examples 1, 3, and/or 4, the following compounds were prepared:

| R$_7$ | R$_1$ | R$_9$ | [M + H]$^+$ |
|---|---|---|---|
| CN | 3-MeO—Ph—CH$_2$— | 3,4-piperonyl | 536 |
| Cl | 3-MeO—Ph—CH$_2$— | 4-Me—Ph | 515 |
| Cl | 3-MeO—Ph—CH$_2$— | 3-F-4-Me—Ph | 533 |
| Cl | 3-MeO—Ph—CH$_2$— | 3,4-piperonyl | 545 |
| F | 3-MeO—Ph—CH$_2$— | 4-Me—Ph | 499 |
| F | 3-MeO—Ph—CH$_2$— | 3-F-4-Me—Ph | 517 |

Example 12

Preparation of 2-[(R)-1-(4-Amino methyl-2-p-tolyl-imidazol-1-yl)-2-methyl-propyl]-3-benzyl-7-chloro-chromen-4-one a) 2-[(R)-1-(3-Phthalimido-2-oxo-propylamino)-2-methyl-propyl]-3-benzyl-7-chloro-chromen-4-one To 2-((R)-1-amino-2-methyl-propyl)-3-benzyl-7-chloro-chromen-4-one (0.5 g, 1.5 mMol) and K$_2$CO$_3$ (0.21 g, 1.5 mMol) in DMF (10 mL) was added N-(3-bromo-2-oxopropyl)-phthalimide (0.45 g, 1.5 mMol) (Nair et al.; J. Org. Chem. 40; 1975, 1745). The reaction was stirred at RT for 3 h, concentrated under vacuum, taken Up in EtOAc, washed with water, brine, dried (Na$_2$SO$_4$) and evaporated to give the title compound (0.88 g, 100%) as a yellow solid: MS (ES) m/e 543.2 (M+H)$^+$.

b) 2-{(R)-1-[N-Toluoyl-(3-phthalimido-2-oxo-propyl)amino]-2-methyl-propyl}-3-benzyl-7-chloro-chromen-4-one To 2-[(R)-1-(3-phthalimido-2-oxo-propylamino)-2-methyl-propyl]-3-benzyl-7-chloro-chromen-4-one (0.88 g, 1.5 mMol) in CH$_2$Cl$_2$ (10 mL) was added Et$_3$N (0.23 mL, 1.6 mMol) and toluoyl chloride (0.21 mL, 1.6 mMol). The reaction was stirred at RT for 18 h, concentrated under vacuum, taken up in EtOAc, washed with 1 N HCl, brine, dried (MgSO$_4$) and evaporated to dryness. Purification by flash chromatography) on silica gel (5-15% EtOAc/hexane) followed by trituration with pet. ether, filtration and drying under vacuum gave the title compound (0.89 g, 90%) as a white solid: MS (ES) m/e 661.2 (M+H)$^+$.

c) N-{1-[(R)-1-(3-Benzyl-7-chloro-4-oxo-chromen-2-yl)-2-methyl-propyl]-2-p-tolyl-1H-imidazol-4-ylmethyl}-phthalimide To 2-{(R)-1-[N-toluoyl-(3-phthalimido-2-oxo-propyl)amino]-2-methyl-propyl}-3-benzyl-7-chloro-chromen-4-one (0.88 g, 1.3 mMol) and NH$_4$OAc (5.13 g, 66.8 mMol) was added HOAc (15 mL). The reaction was stirred and heated to reflux (155° C. oil bath) for 2.5 h, cooled to RT and concentrated under vacuum. The remaining residue was taken up in EtOAc, washed with water, brine, dried (MgSO$_4$) and evaporated to dryness. Purification by flash chromatography on silica gel (50% EtOAc/hexane) followed by trituration with (1:2) Et$_2$O/pet. ether, filtration and drying under vacuum gave the title compound (0.51 g, 61%) as a tan solid: $^1$H NMR (400 MHz, CDCl$_3$) δ 8.11 (d, J=8.6 Hz, 1H), 7.89 (2d, 2H), 7.73 (2d, 2H), 7.53 (d, J=1.8 Hz, 1H), 7.52 (s, 1H), 7.39 (d, J=8.0 Hz, 2H), 7.36 (dd, 1H), 7.32 (d, J=8.0 Hz, 2H), 7.14 (m, 3H), 6.74 (d, J=1.5 Hz, 1H), 6.72 (s, 1H), 5.04 (d, J=8.8 Hz, 1H), 4.94 (s, 2H), 4.01 (d, J=15.5 Hz, 1H), 2.63 (m, 1H), 2.46 (s, 3H), 2.44 (d, J=15.5 Hz, 1H), 0.95 (d, J=6.6 Hz, 3H), 0.29 (d, J=6.7 Hz, 3H); MS (ES) m/e 642.0 (M+H)$^+$.

d) 2-[(R)-1-(4-Aminomethyl-2-p-tolyl-imidazol-1-yl)-2-methyl-propyl]-3-benzyl-7-chloro-chromen-4-one To N-{1-[(R)-1-(3-benzyl-7-chloro-4-oxo-3,4-dihydro-chromen-2-yl)-2-methyl-propyl]-2-p-tolyl-1H-imidazol-4-ylmethyl}-phthalimide (0.50 g, 0.78 mMol) in EtOH (15 mL) was added hydrazine monohydrate (0.12 mL, 2.5 mMol). The reaction was stirred at RT for 72 h. filtered through a pad of Celite® to remove the insoluble precipitate, rinsed with EtOH and evaporated to dryness. Purification by flash chromatography on silica gel [5-10% (5% NH$_4$OH in MeOH)/CH$_2$Cl$_2$] gave the title compound (364 mg, 91%) as a white solid foam: $^1$H NMR (400 MHz. CDCl$_3$) δ 8.14 (d, J=8.6 Hz, 1H), 7.63 (d, J=1.8 Hz, 1H), 7.37 (m, 6H), 7.15 (m, 3H), 6.71 (d, J=1.7 Hz, 1H), 6.69 (s, 1H), 5.00 (d, J=10.9 Hz, 1H), 4.07 (d, J=15.5 Hz, 1H), 3.92 (d, 1H), 3.88 (d, 1H), 2.72 (br s, 2H), 2.65 (m, 1H), 2.49 (s, 3H), 2.48 (d, J=15.5 Hz, 1H), 0.93 (d, J=6.6 Hz, 3H), 0.30 (d, J=6.7 Hz, 3H): MS (ES) m/e 512.2 (M+H)$^+$.

Following procedures analogous to those set forth above, the following compounds were prepared:

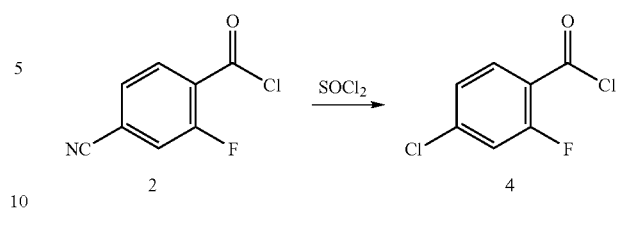

| $R_7$ | $R_1$ | $R_9$ | $[M + H]^+$ |
|---|---|---|---|
| F | Ph—CH$_2$— | 4-Me—Ph | 510 |
| F | Ph—CH$_2$— | 3-F-4-Me—Ph | 528 |
| CN | Ph—CH$_2$— | 3-F-4-Me—Ph | 535 |
| Cl | Ph—CH$_2$— | 3-F-4-Me—Ph | 544 |
| Cl | 3-MeO—Ph—CH$_2$— | 4-Me—Ph | 556 |
| Cl | 3-MeO—Ph—CH$_2$— | 3-F-4-Me—Ph | 574 |
| CN | Ph—CH$_2$— | 4-Me—Ph | 517 |
| Cl | 3-CN—Ph—CH$_2$— | 4-Me—Ph | 551 |
| Cl | 3-CN—Ph—CH$_2$— | 3-F-4-Me—Ph | 569 |
| F | 3-MeO—Ph—CH$_2$— | 4-Me—Ph | 540 |
| CN | 3-MeO—Ph—CH$_2$— | 4-Me—Ph | 547 |
| CN | 3-CN—Ph—CH$_2$— | 3-F-4-Me—Ph | 560 |
| F | 3-MeO—Ph—CH$_2$— | 3-F-4-Me—Ph | 588 |
| F | 3-CN—Ph—CH$_2$— | 3-F-4-Me—Ph | 553 |

Example 13

Preparation of N-{1-[(R)-1-(3-Benzyl-7-chloro-4-oxo-3,4-dihydro-chromen-2-yl)-2-methyl-propyl]-2-p-tolyl-1H-imidazol-4-ylmethyl}-acetamide To 2-[(R)-1-(4-aminomethyl-2-p-tolyl-imidazol-1-yl)-2-methyl-propyl]-3-benzyl-7-chloro-chromen-4-one (0.17 g, 0.33 mMol) in CH$_2$Cl (5 mL) was added with stirring, pyridine (27 uL, 0.33 mMol) and Ac$_2$O (63 uL, 0.67 mMol). After stirring at RT for 4 h the reaction was concentrated under vacuum. The remaining residue was triturated with (1:1) Et$_2$O/pet. ether, filtered and dried under vacuum to give the title compound (163 mg, 89%) as a white solid: $^1$H NMR (400 MHz, CDCl$_3$) δ 8.14 (d, J=8.6 Hz, 1H), 7.59 (d, J=1.8 Hz, 1H), 7.43 (m, 6H), 7.17 (m, 3H), 6.84 (br s, 1H), 6.71 (d, J=2.2 Hz, 1H), 6.69 (s, 1H), 5.07 (d, J=10.9 Hz, 1H), 4.50 (2d, 1H), 4.43 (2d, 1H), 4.07 (d, J=15.5 Hz 1H), 2.66 (m, 1H), 2.51 (s, 3H), 2.48 (d, J=15.5 Hz, 1H), 2.00 (s, 3H), 0.95 (d, 6.6 Hz, 3H), 0.34 (d, J=6.7 Hz, 3H); MS (ES) m/e 554.4 (M+14)$^+$.

Example 14

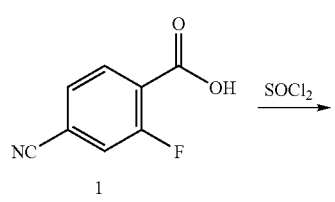

A mixture of 4-cyano-2-fluorobenzoic acid (1.25 g). DMF (0.1 mL), and thionyl chloride (50 mL) in a 250 mL round-bottom flask equipped with a reflux condenser under N$_2$ atmosphere was heated to reflux in a 90° C. oil bath for 30 mins. The reflux condenser was replaced with a distillation head and the excess thionyl chloride was distilled from the reaction pot. The oil bath temperature was increased to 120° C. to facilitate distillation. After 2 hours, the reaction vessel as cooled to 23° C. and placed under reduced preasule (~25 Torr). The reaction vessel was then heated to 90° C. for 20 mins, then to 130° C. for 90 minutes to remove any excess remaining, thionyl chloride. The reaction vessel was then cooled to 23° C. and placed under high vacuum (~0.2 Torr). The reaction vessel was equipped with a clean distillation head and collection flask. The vessel was placed into a 137° C. oil bath and the product was distilled from the reaction pot (b.p.=107° C.@~0.2 Torr). Upon cooling the distillate solidified, providing 2 as a white solid in close to quantitative yield.

A mixture of 4-chloro-2-fluorobenzoic acid (3, 25 g), DMF (0.1 mL), and thionyl chloride (50 mL) in a 250 mL round-bottom flask equipped with a reflux condenser under N$_2$ atmosphere was heated to reflux in a 90° C. oil bath for 30 mins. The reflux condenser was replaced with a distillation head and the excess thionyl chloride was distilled from the reaction pot. The oil bath temperature was increased to 120° C. to facilitate distillation. After 2 hours, the reaction vessel was cooled to 23° C. and placed under reduced pressure (~25 Torr). The reaction vessel was then heated to 90° C. for 20 mins, then to 120° C. for 90 minutes to remove any excess remaining thionyl chloride. The reaction vessel was then cooled to 23° C. and then equipped with a clean distillation head and collection flask. The vessel was placed into a 160° C. oil bath and the product was distilled from the reaction pot (b.p.=124° C.@~25 Torr), furnishing 4 was a colorless oil in near quantitative yield.

Example 15

-continued

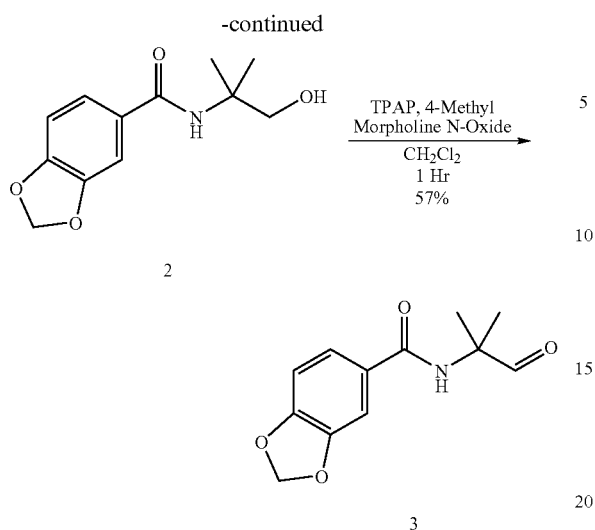

Piperonyloyl Chloride (1, 7.8 g, 42 mmol) was added to a solution of 2-amino-2-methyl-1-propanol (4 ml, 42 mmol), CH$_2$Cl$_2$ (200 mL), and triethylamine (11.7 ml, 84 mmol) at room temperature. The reaction solution was concentrated after 45 minutes, and the resulting residue was diluted with EtOAc (40 mL) and washed with brine (30 mL). The organic layer was dried (MgSO$_4$), filtered, and concentrated to yield a light brown oil. The crude material (2, 8.8 g) was used without further purification.

Tetrapropylammonium perruthenate (TPAP, 638 m, 1.8 mmol) was added portion-wise to a solution of 2 (8.6 g, 36.3 mmol). CH$_2$Cl$_2$ (73 ml, 2 mL/mmol), 4-methyl-morpholine N-oxide (6.4 g, 54.5 mmol), and molecular sieves. 4 Å activated powder (18 g, 500 mg/mmol) at 0° C. under N$_2$. The reaction was allowed to warm to r.t. after 15 minutes. After 1 hour the reaction was complete (TLC) and was filtered through silca, eluted with EtOAc (100 mL), and the filtrate was concentrated. This yielded 7 g of off-white solid (3). The material was recrystallized: EtOAc (30 mL), MeOH (10 mL), and Hexanes (1 mL) were added portion wise with heating and sonication. This was brought to a boil after which hexane (100 mL) was added while cooling. Crystals immediately began to precipitate as the solution was cooled. The mixture was filtered and the crystals were washed with hexane (10 mL) to provide 4.88 g (57%) of 3 as off-white fluffy crystals.

Example 16

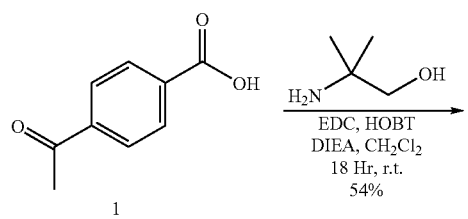

-continued

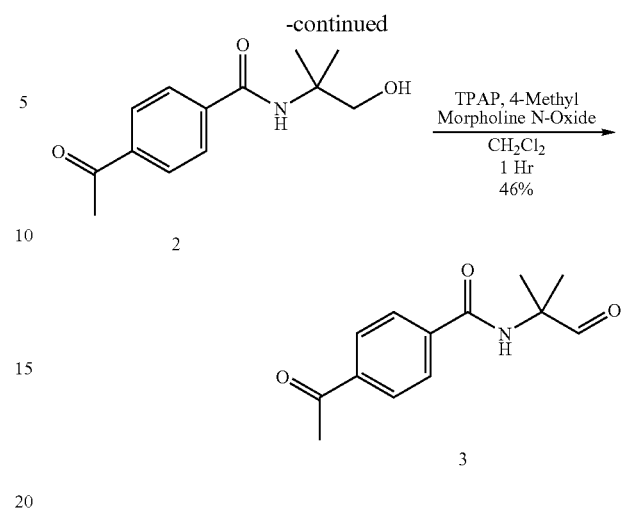

A mixture of 2-amino-2-methyl-1-propanol (4 ml, 42 mmol). CH$_2$Cl$_2$ (200 mL), 4-acetyl benzoic acid (1, 6.9 g, 42 mmol), EDC (1-(3-dimethylaminopropyl)-3-eythylcarbodiimide HCl, 12.1 g, 63 mmol), HOBT (N-hydroxybenzotriazole H$_2$O, 6.4 g, 42 mmol), and Hunig's base (diisopropylethylamine, 22 mL, 126 mmol) was stirred at room temperature for 18 hours. Upon completion (TLC, LC/MS) the reaction mixture was concentrated, and the resulting residue was diluted with EtOAc (50 mL) and washed with NaHCO$_3$ (2×40 mL) and brine (40 mL). The organic layer was dried (MgSO$_4$), filtered, and the filtrate was concentrated. The crude material as purified by flash column chromatography (4:1:1 hexanes:EtOAc:CH$_2$Cl$_2$: 1:1:1 hexanes: EtOAc:CH$_2$Cl$_2$; 1:1 EtOAc:CH$_2$Cl$_2$) to remove bisacylated material. Alcohol 2 was obtained in 54% yield (5.36 g).

Tetrapropylammonium perruthenate (TPAP, 387 mg, 1.1 mmol) was added portion-wise to a solution of 2 (5.36 g, 22.8 mmol) CH$_2$Cl$_2$ (46 mL 2 mL/mmol), 4-methyl-morpholine N-oxide (4 g, 34.2 mmol), and molecular sieves. 4 Å activated powder (11.4 g, 500 mg/mmol) at 0° C. under N$_2$. The reaction was allowed to warm to r.t. after 15 minutes. After 1 hour the reaction was complete (TLC) and was filtered through silca, which was eluted with EtOAc (100 mL), and the filtrate was concentrated. This yielded 4.4 g of light pink solid (3). The material was recrystallized: 1:1 Hexanes:EtOAc (5 mL), CH$_2$Cl$_2$ (20 mL), and MeOH (10 mL) were added portion-wise with heating and sonication. This was brought to a boil after which hexane (100 mL) was added while cooling. Crystals immediately began to precipitate as the solution was cooled. The mixture was filtered and the crystals were washed with hexane (10 mL), affording 2.46 g (46%) of 3 as off-white fluffy crystals.

Example 17

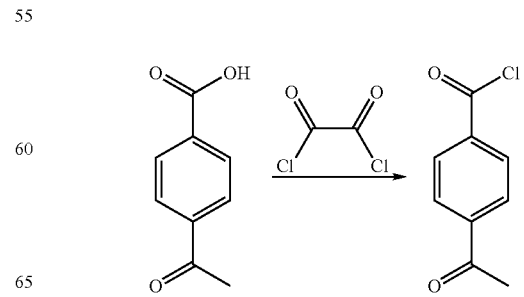

A solution of 4-acetyl benzoic acid (500 mg) in oxalyl chloride (5 mL) was heated to reflux for 2 hours. Any remaining oxalyl chloride was evaporated by rot-vap, and the residue was dried by vacuum. The yield of product was quantitative.

Example 18

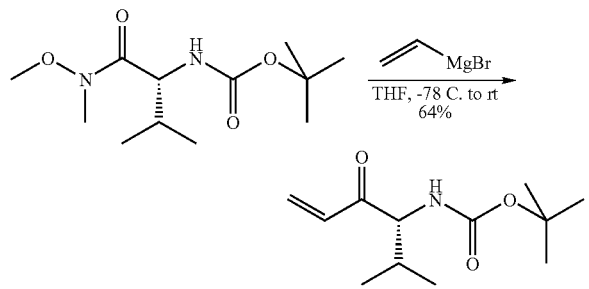

((R)-1-Isopropyl-2-oxo-but-3-enyl)-carbamic acid tert-butyl ester

Tetrahydrofuran (THF, 100 mL) and a 1.0M solution of vinyl magnesium bromide in THF (360 mL 360 mmol, 3.1 equiv) was cooled to −78° C. while stirring under a nitrogen atmosphere. The mixture was treated dropwise with a solution of [(R)-(methoxy-methyl-carbamoyl)-methyl-propyl]-carbamic acid tert-butyl ester (30.3 g, 116 mmol, 1 equiv) in THF (50 mL) over 30 min. After the resultant dark yellow mixture was stirred for 30 min at −78° C. the cooling bath was removed and the reaction mixture was warmed slowly to room temperature overnight (15 h). The reaction mixture was poured slowly into an ice-chilled solution of 1N aqueous hydrochloric acid (700 mL) and then warmed to room temperature. The organics were extracted with (3×600 mL) ethyl acetate, dried over sodium sulfate, filtered, and concentrated in vacuo. Purification by flash column chromatography (5-10% ethyl acetate/hexanes) provided the product as a white solid (16.8 g, 64%). ESMS [M+H]$^+$: 228.4.

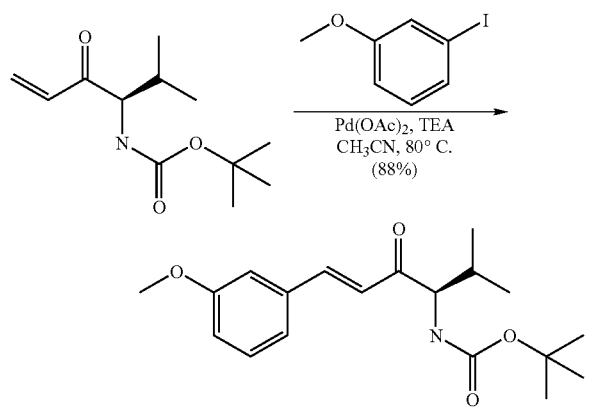

[(R)-(E)-1-Isopropyl-4-(3-methoxy-phenyl)-2-oxo-but-3-enyl]-carbamic acid tert-butyl ester To a solution of ((R)-1-Isopropyl-2-oxo-but-3-enyl)-carbamic acid tert-butyl ester (13.54 g, 59.6 mmol) in dry acetonitrile (150 mL) under argon, was added 3-iodoanisole (113.96 g, 59.6 mmol), triethylamine (9.1 mL 65.6 mmol) followed by palladium (II) acetate (335 mg, 1.49 mmol). The resulting clear yellow solution was heated to 80° C. Upon heating, the reaction darkened and the precipitation of palladium black occurred. After 15 h, the reaction mixture was allowed to cool to room temperature, quenched with water (150 mL) and diluted with ether (150 mL). The ether layer was washed with brine (100 mL) and the combined aqueous layers were extracted with ether (two 50 mL portions). The extracts were dried over magnesium sulfate, filtered and concentrated under reduced pressure. The residue was immediately purified by silica gel chromatography (9:1 hexanes/EtOAc) to provide 17.6 g (88%) of [(R)-(E)-1-Isopropyl-4-(3-methoxy-phenyl)-2-oxo-but-3-enyl]-carbamic acid tert-butyl ester as a yellow oil. MS(ES+) m/e 334.0 [M+H]$^+$.

[(R)-(Z)-4-(3-Cyano-phenyl)-1-isopropyl-2-oxo-but-3-enyl]-carbamic acid tert-butyl ester Following the procedure described for [(R)-(E)-1-isopropyl-4-(3-methoxy-phenyl)-2-oxo-but-3-enyl]-carbamic acid tert-butyl ester with 3-iodobenzonitrile (5.50 g, 24.0 mmol, 1 equiv) afforded the title compound as a yellow solid (7.4 g of ~90% purity material). ESMS [M+H]$^+$: 329.2.

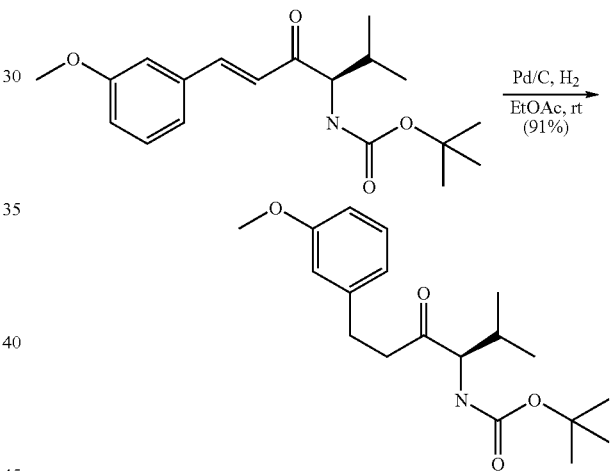

[(R)-(E)-1-Isopropyl-4-(3-methoxy-phenyl)-2-oxo-butyl]-carbamic acid tert-butyl ester To a solution of [(R)-(E)-1-Isopropyl-4-(3-methoxy-phenyl)-2-oxo-but-3-enyl]-carbamic acid tert-butyl ester (17.6 g, 52.9 mmol) in ethyl acetate (450 mL) under nitrogen was added 10 wt % palladium on carbon (300 mg). The nitrogen was replaced with a balloon of hydrogen and the flask was purged. After 3 h, the reaction flask was purged with nitrogen and filtered through a pad of celite (rinsing with ethyl acetate). The filtrate was concentrated under reduced pressure and the residue was purified by silica gel chromatography (9:1 hexanes/EtOAc) to provide 16.2 g (91%) of [(R)-(E)-1-Isopropyl-4-(3-methoxy-phenyl)-2-oxo-butyl]-carbamic acid tert-butyl ester as a colorless oil. MS(ES+) m/e 336.4 [M+H]$^+$. [α]$_D^{20}$=+19.1 (c=0.755 MeOH). $^1$H NMR (400 MHz, CDCl$_3$) δ 7.21 (m, 1H), 6.80-6.77 (m, 2H), 6.75 (s, 1H), 5.13 (d, J=8.4 Hz, 1H), 4.28 (dd, J=8.8, 4.4 Hz, 1H), 3.81 (s, 3H), 2.93-2.88 (m, 2H), 2.85-2.76 (m, 2H), 2.14 (m, 1H), 1.46 (s, 9H), 1.00 (d, J=6.8 Hz, 3H), 0.75 (d, J=6.8 Hz, 3H).

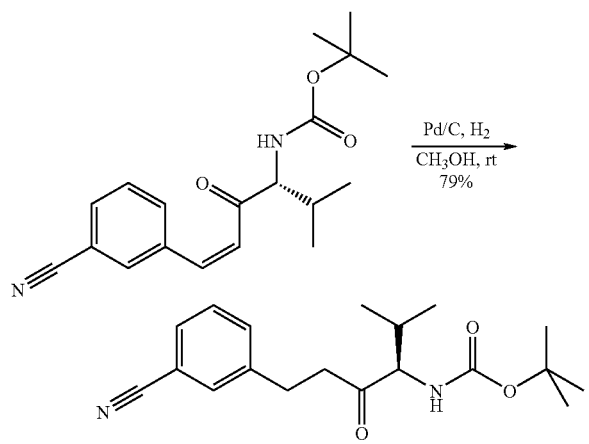

[(R)-4-(3-Cyano-phenyl)-1-isopropyl-2-oxo-butyl]-carbamic acid tert-butyl ester

Palladium on carbon (740 mg of 10% wt/wt Pd/C) was added to a degassed solution of [(R)-(Z)-4-(3-cyano-phenyl)-1-isopropyl-2-oxo-but-3-enyl]-carbamic acid tert-butyl ester (7.4 g, 22.5 mmol, 1 equiv) in methanol (200 mL) at room temperature. The reaction mixture was thoroughly degassed and backfilled with hydrogen gas from a balloon. Hydrogenation proceeded at atmospheric pressure for 2.5 h. The (degassed) reaction mixture was then diluted with diethyl ether (300 mL), filtered through Celite, and washed with additional ether (2×100 mL). Upon concentration in vacuo, the residue was purified by flash column chromatography (20% ethyl acetate-hexanes) to provide the ketone product as a white solid (5.9 g, 79%). ESMS [M+H]$^+$: 331.2. $^1$H NMR (400 MHz, CDCl$_3$) δ 7.51 (m, 2H), 7.46 (m, 1H), 7.41 (m, 1H), 5.07 (m, 1H), 4.24 (m, 1H), 2.98 (m, 2H), 2.86 (m, 2H), 2.11 (m, 1H), 1.45 (s, 9H), 0.98 (d, 3H, J=6.76 Hz), 0.74 (d, 3H, 6.78 Hz), [α]$_D$=+24.74 (c=0.95, CH$_3$OH).

Example 19

Following procedures analogous to those set forth above, the following compounds were prepared:

| R$_7$ | R$_1$ | R$_3$ | [M + H]$^+$ |
|---|---|---|---|
| F | 3-MeO—Ph—CH$_2$— | 3-F-4-Me—Ph— | 549 |
| F | 3-MeO—Ph—CH$_2$— | 4-MeO—Ph— | 547 |
| F | 3-MeO—Ph—CH$_2$— | 4-Me—Ph— | 531 |
| F | 3-MeO—Ph—CH$_2$— | 3,4-piperonyl- | 561 |
| F | 3-MeO—Ph—CH$_2$— | Methoxymethyl- | 485 |
| CN | 3-MeO—Ph—CH$_2$— | 4-Ac—Ph— | 566 |
| CN | 3-MeO—Ph—CH$_2$— | 4-Me—Ph— | 538 |
| CN | 3-MeO—Ph—CH$_2$— | 3,4-piperonyl- | 568 |
| CN | 3-MeO—Ph—CH$_2$— | 3-F-4-Me—Ph— | 556 |
| Cl | 3-MeO—Ph—CH$_2$— | 3-F-4-Me—Ph— | 565 |
| Cl | 3-MeO—Ph—CH$_2$— | 4-Me—Ph— | 547 |
| Cl | 3-MeO—Ph—CH$_2$— | Methoxymethyl- | 501 |
| Cl | 3-MeO—Ph—CH$_2$— | 3,4-piperonyl- | 577 |
| MeO— | 3-MeO—Ph—CH$_2$— | 3-F-4-Me—Ph— | 561 |
| MeO— | 3-MeO—Ph—CH$_2$— | 4-Me—Ph— | 543 |
| MeO— | 3-MeO—Ph—CH$_2$— | 3,4-piperonyl | 573 |
| OH | 3-MeO—Ph—CH$_2$— | 3-F-4-Me—Ph— | 547 |
| CN | Ph—CH$_2$— | 4-OEt—Ph— | 538.2 |
| CN | Ph—CH$_2$— | 6-trifluoromethyl-3-pyridyl | 563.2 |
| CN | Ph—CH$_2$— | 2-benzo[b]thiophene | 550.2 |
| CN | Ph—CH$_2$— | 3-(5-t-butyl-2-methyl-2H-pyrazole) | 554.4 |
| CN | Ph—CH$_2$— | 3-(2,5-dimethyl-2H-pyrazole) | 512.4 |
| F | Ph—CH$_2$— | 6-trifluoromethyl-3-pyridyl | 556.0 |
| F | Ph—CH$_2$— | 2-furyl | 477.0 |
| F | Ph—CH$_2$— | 3-(5-t-butyl-2-methyl-2H-pyrazole) | 547.2 |
| Cl | Ph—CH$_2$— | 4-CN—Ph— | 529.2 |
| Cl | Ph—CH$_2$— | 4-AcNH—Ph— | 561.4 |
| Cl | Ph—CH$_2$— | 6-trifluoromethyl-3-pyridyl- | 573.0 |
| Cl | Ph—CH$_2$— | 5-benzo[1,2,3]thiadiazole- | 562.2 |
| Cl | Ph—CH$_2$— | 2-furyl | 494.4 |
| Cl | Ph—CH$_2$— | 3-(2,5-dimethyl-2H-pyrazole)- | 522.0 |
| F | Ph—CH$_2$— | 4-pyridyl- | 488.4 |
| F | Ph—CH$_2$— | 3-(2,5-dimethyl-2H-pyrazole)- | 505.4 |
| F | Ph—CH$_2$— | 4-AcNH—Ph— | 544.4 |
| F | Ph—CH$_2$— | 5-benzo[1,2,3]thiadiazole- | 545.2 |
| CN | Ph—CH$_2$— | 2-(1-methyl-1H-indole)- | 547.4 |
| Cl | Ph—CH$_2$— | 3-pyridyl- | 505.2 |
| F | Ph—CH$_2$— | 4-OMe—Ph— | 517.2 |
| CN | Ph—CH$_2$— | 3-(2,5-dimethyl-furan)- | 512.2 |
| F | Ph—CH$_2$— | 3-(2,5-dimethyl-furan)- | 505.2 |
| CN | Ph—CH$_2$— | 2-(5-methyl-thiophene)- | 514.2 |
| F | Ph—CH$_2$— | 2-(5-methyl-thiophene)- | 507.0 |
| CN | Ph—CH$_2$— | 2-(1-methyl-1H-pyrrole)- | 497.4 |
| CN | Ph—CH$_2$— | 5-benzo[1,2,3]thiadiazole- | 550.0 |
| Cl | Ph—CH$_2$— | 6-Me-3-pyridyl- | 518.2 |
| Cl | Ph—CH$_2$— | 2-(1-methyl-1H-pyrrole)- | 506.0 |
| Cl | Ph—CH$_2$— | 2-(5-methyl-pyrazine)- | 520.2 |
| Cl | Ph—CH$_2$— | 3-(5-methyl-isoxazole)- | 508.2 |
| Cl | Ph—CH$_2$— | 3-benzo[c]isoxazole- | 544.2 |
| CN | Ph—CH$_2$— | 4-(1-methyl-1H-imidazole)- | 498.1 |
| CN | Ph—CH$_2$— | 3-N(CH$_3$)$_2$—Ph— | 537.4 |
| CN | Ph—CH$_2$— | 3-(5-methyl-2-trifluoromethyl-furan)- | 566.4 |
| CN | Ph—CH$_2$— | 3-(5-methyl-isoxazole)- | 499.6 |
| F | Ph—CH$_2$— | 4-(1-methyl-1H-imidazole)- | 491.4 |
| F | Ph—CH$_2$— | 2-(1-methyl-1H-pyrrole)- | 490.4 |
| F | Ph—CH$_2$— | 3-benzo[c]isoxazole- | 528.4 |
| F | Ph—CH$_2$— | 3-(5-methyl-isoxazole)- | 492.4 |

Example 20

A pharmaceutical composition for intravenous administration is prepared in the following manner.

1 mg/mL (as free base) IV solution with the vehicle being pH 5.0. 50 mM sodium acetate buffer containing 3.5% (w/v) mannitol:

| Composition* | Unit Formula (mg/mL) |
|---|---|
| Compound of Example 2 (free base) | 1.000 |
| Glacial Acetic Acid | 1.081 |
| Sodium Acetate Trihydrate | 4.355 |
| Mannitol. pyrogen free | 35.000 |
| Water for Injection (WFI) | q.s. to 1 mL |

*All components other than the active compound are USP or Ph. Eur.

A suitable compounding vessel is filled to approximately 75% of the bulk solution volume with WFI. The glacial acetic acid (1.081 g), sodium acetate trihydrate (4.355 g), mannitol (35.000 g), and active (1.000 g) are weighed and individually added to the compounding vessel. After the additions, the ingredients are dissolved in the mixture by stirring with a mixer. The pH of the bulk solution is measured and adjusted to 5.0 with 5N NaOH or 5N glacial acetic acid. The solution is brought to its final volume (1 liter) with WFI. Where the active compound is a pharmaceutically acceptable salt, hydrate or salt of a hydrate, e.g., a monochloride salt or a hydrate of a monochloride salt, the amount of the active equivalent to the free base is added.

Example 21

Preparation of a hydrochloride salt of N-(3-Aminopropyl)-N-[(R)-1-3-benzyl-7-chloro-4-oxo-4H-chromen-2-yl)-2-methyl-propyl]-4-methyl-benzamide In one embodiment, a hydrochloric acid salt of N-(3-Aminopropyl)-N-[(R)-1-3-benzyl-7-chloro-4-oxo-4H-chromen-2-yl)-2-ethyl-propyl]-4-methyl-benzamide, such as prepared in accordance with Example 2, is formed in the following manner. An HCl salt is suitably prepared by reacting the free base (e.g. dissolved in a suitable solvent, such as one or more of TBME, THF, and ethylacetate) with hydrochloric acid, suitably aqueous hydrochloric acid or otherwise in the presence of water. The mixture is suitably seeded with HCl salt to assist crystallization. The resulting salt may be isolated using conventional techniques such as filtration and drying (suitably washing the salt with a solvent, such as one or more of TBME, THF, and ethylacetate).

In a particular embodiment, the salt is prepared as follows:
1. Dissolve the free base into 10 volumes of TBME and 5 volumes of THF, dissolution suitably conducted at room temperature;
2. Add aqueous HCl, e.g. 6.0 M or 12.0 M, suitably 1.1 eq. e.g. dropwise;
3. Suitably seed the solution with crystals of HCl salt, e.g. prepared according to preparation B below;
4. Suitably stir until crystals form;
5. Isolate the crystals, suitably by filtration, washing, with a suitable solvent such as TBME, and drying.

In more particular embodiments a salt is prepared as follows:

Preparation A

To a vial fitted with a stir bar add 500 mg of N-(3-Aminopropyl)-N-[(R) 1-3-benzyl-7-chloro-4-oxo-4H-chromen-2-yl)-2-methyl-propyl]-4-methyl-benzamide, and 3 ml TBME, and dissolve the free base in the TBME at room temperature.

Bubble in HCl gas for about 30 seconds until a white solid forms. Filter and rinse the solids twice with 500 µl TBME. Transfer the solids to a test tube, add 4 ml TBME and a stir bar, and stir at room temperature (the salt does not dissolve). Place the test tube containing the mixture in an Argonaut RS10 heating block (Argonaut Technologies, Foster City, Calif.), or all equivalent, and temperature cycle as follows:
1. 30 min at room temperature
2. ramp to 40C over 30 min and hold at 40C for 30 min
3. ramp to room temperature over 30 min and hold at room temperature for 30 min
4. ramp to 10C over 30 min and hold at 10C for 30 min
5. ramp to room temperature over 30 min and hold at room temperature for 30 min
6. repeat 2 to 5 as desired By 20 hours cycling some solvent evaporates, a white powder forms on the sides and a melt-like solid forms in the bottom of the test tube. Add 2 ml TBME. After 15 days, filter the light yellow solids and wash twice with about 0.5 ml TBME then twice with 1 ml hexane. Dry in a vacuum oven at room temperature for 12-24 hours to obtain about 440 mg HCl salt.

FIGS. 1 and 2 represent a XRPD and MDSC scan, respectively, of a salt prepared according to Preparation A.

Preparation B

Dissolve 4.23 g of N-(3-Aminopropyl)-N-[(R)-1-3-benzyl-7-chloro-4-oxo-4H-chromen-2-yl)-2-methyl-propyl]-4-methyl-benzamide in 5 volumes (21 ml) of THF. Add 10 volumes (42 ml) of TBME (tert-butyl methyl ether), then 1.1 eq of 12N HCl (750 µl) in one portion. Seed with HCl salt Such as prepared in Preparation A (e.g. in 3 additions of about 10 mg each staggered over about 10 minutes). Stir the mixture overnight, e.g. for about 12-24 hours. Filter the mixture, wash the solids with TBME, and dry the solids in a vacuum oven at room temperature overnight. e.g. for about 12-24 hours, to yield about 4.3 g of HCl salt.

FIG. 3 represents an XRPD scan of a salt prepared according to Preparation B.

The present invention includes crystalline N-(3-Aminopropyl)-N-[(R)-1-3-benzyl-7-chloro-4-oxo-4H-chromen-2-yl)-2-methyl-propyl]-4-methyl-benzamide hydrochloride salt having characteristic X-ray diffraction peaks at about 4.8, 9.7, 14.7, 17.9, 18.3, 20.1, 20.9, 22.5, 23.2, 23.8, 26.1 and 26.9 degrees 2 theta.

Example 22

Inhibition of Cellular Viability in Tumor Cell Lines Treated with KSP Inhibitors.r Materials and Solutions:
Cells: SKOV3, Ovarian Cancer (human).
Media: Phenol Red Free RPMI+5% Fetal Bovine Serum+2 mM L-glutamine.
Colorimetric Agent for Determining Cell Viability: Promega MTS tetrazolium compound.
Control Compound for max cell kill: Topotecan, 1 µM.
Procedure: Day 1—Cell Plating:
Adherent SKOV3 cells are washed with 10 mLs of PBS followed by the addition of 2 mLs of 0.25% trypsin and incubation for 5 minutes at 37° C. The cells are rinsed from the flask using 8 mL of media (phenol red-free RPMI+5% FBS) and transferred to fresh flask. Cell concentration is determined using a Coulter counter and the appropriate volume of cells to achieve 1000 cells/100 µL is calculated. 100 µL of media cell suspension (adjusted to 1000 cells/100 µL) is added to all wells of 96-well plates, followed by incubation for 18 to 24 hours at 37° C. 100% humidity, and 5% $CO_2$ allowing the cells to adhere to the plates.

Procedure: Day 2—Compound Addition:

To one column of the wells of an autoclaved assay block are added an initial 2.5 µL of test compound(s) at 400× the highest desired concentration. 1.25 µL of 400× (400 µM) Topotecan is added to other wells (optical density's from these wells are used to subtract out for background absorbance of dead cells and vehicle). 500 µL of media without DMSO are added to the wells containing (test compound, and 250 µL to the Topotecan wells. 250 µL of media+0.5% DMSO is added to all remaining wells, into which the test compound(s) are serially diluted. By row, compound-containing media is replica plated (in duplicate) from the assay block to the corresponding cell plates. The cell plates are incubated for 72 hours at 37° C., 100% humidity, and 5% $CO_2$.

Procedure: Day 4—MTS Addition and OD Reading:

The plates are removed from the incubator and 40 µl MTS/PMS is added to each well. Plates are then incubated for 120 minutes at 37° C., 100% humidity, 5% $CO_2$, followed by reading the ODs at 490 nm after a 5 second shaking cycle in a ninety-six well spectrophotometer.

Data Analysis

The normalized % of control (absorbance-background) is calculated and an XLfit is used to generate a dose-response curve from which the concentration of compound required to inhibit viability by 50% is determined. The compounds of the present invention show activity when tested by this method as described above.

Example 23

Enantiomer Separation

An enriched 3:1 R:S mixture of chromenone enantiomers was separated into its pure enantiomers by chiral chromatography with the following conditions: Column—Chiralpak AD. 250×4.6 mill (Diacel Inc.). Sample—22.5 mg/ml in 1:1 i-PrOH:hexanes. Conditions—40 mill at isocratic 50% i-PrOH in Hexanes. (S)-enantiomer elutes at 18.35 min. (R)-enantiomer elutes at 26.87 min. The (R)-enantiomer was significantly more potent than the (S)-enantiomer of the compound of Example 2.

Example 24

Monopolar Spindle Formation Following Application of a KSP Inhibitor

Human tumor cells Skov-3 (ovarian) were plated in 96-well plates at densities of 4,000 cells per well, allowed to adhere for 24 hours, and treated with various concentrations of the chromenone compounds for 24 hours. Cells were fixed in 4% formaldehyde and stained with antitubulin antibodies (subsequently recognized using fluorescently-labeled secondary antibody) and Hoechst dye (which stains DNA).

Visual inspection revealed that the compounds caused cell cycle arrest in the prometaphase stage of mitosis. DNA was condensed and spindle formation had initiated, but arrested cells uniformly displayed monopolar spindles, indicating that there was an inhibition of spindle pole body separation. Microinjection of anti-KSP antibodies also causes mitotic arrest with arrested cells displaying monopolar spindles.

Example 25

Inhibition of Cellular Proliferation in Tumor Cell Lines Treated with KSP Inhibitors.

Cells were plated in 96-well plates at densities from 1000-2500 cells/well of a 96-well plate and allowed to adhere/grow for 24 hours. They were then treated with various concentrations of drug for 48 hours. The time at which compounds are added is considered $T_0$. A tetrazolium-based assay using the reagent 3-(4,5-dimethylthiazol-2-yl)-5-(3-carboxymethoxyphenyl)-2-(4-sulfophenyl)-2H-tetrazolium (MTS) (U.S. Pat. No. 5,185,450) (see Promega product catalog #G3580, CellTiter 96®AQ$_{ueous}$ One Solution Cell Proliferation Assay) was used to determine the number of viable cells at $T_0$ and the number of cells remaining after 48 hours compound exposure. The number of cells remaining after 48 hours was compared to the number of viable cells at the time of drug addition, allowing for calculation of growth inhibition.

The growth over 48 hours of cells in control wells that had been treated with vehicle only (0.25% DMSO) is considered 100% growth and the growth of cells in wells with compounds is compared to this.

A $Gi_{50}$ was calculated by plotting the concentration of compound in µM vs the percentage of cell growth in treated wells. The $Gi_{50}$ calculated for the compounds is the estimated concentration at which growth is inhibited by 500% compared to control. i.e. the concentration at which:

$$100 \times [(\text{Treated}_{48} - T_0)/(\text{Control}_{48} - T_0)] = 50$$

wherein $\text{Treated}_{48}$ is the value at 48 hours for the treated cells and $\text{Control}_{48}$ is the value at 48 hours for the control population.

All concentrations of compounds are tested in duplicate and controls are averaged over 12 wells. A very similar 96-well plate layout and $Gi_{50}$ calculation scheme is used by the National Cancer Institute (see Monks, et al., J. Natl Cancer Inst. 83:757-766 (1991)). However, the method by which the National Cancer Institute quantitates cell number does not use MTS, but instead employs alternative methods.

Compounds of Examples 1-13 above inhibited cell proliferation in human ovarian tumor cell lines (SKOV-3).

Example 26

Calculation of $IC_{50}$:

Measurement of a compound's $IC_{50}$ for KSP activity uses an ATPase assay. The following solutions are used: Solution 1 consists of 3 mM phosphoenolpyruvate potassium salt (Sigma P-7127), 2 mM ATP (Sigma A-3377), 1 mM IDTT7 (Sigma D-9779), 5 µM paclitaxel (Sigma T-7402), 10 ppm antifoam 289 (Sigma A-8436), 25 mM Pipes/KOH pH 6.8 (Sigma P6757), 2 mM MgCl2 (VWR JT400301), and 1 mM EGTA (Sigma E3889). Solution 2 consists of 1 mM NADH (Sigma N8129), 0.2 mg/ml BSA (Sigma A7906), pyruvate kinase 7 U/ml, L-lactate dehydrogenase 10 U/ml (Sigma P0294), 100 nM KSP motor domain, 50 µg/ml microtubules, 1 mM DTT (Sigma D9779), 5 µM paclitaxel (Sigma T-7402), 10 ppm antifoam 289 (Sigma A-8436), 25 mM Pipes/KOH pH 6.8 (Sigma P6757). 2 mM MgCl2 (VWR JT4003-01), and 1 mM EGTA (Sigma E3889). Serial dilutions (8-12 two-fold dilutions) of the compound are made in a 96-well microtiter plate (Corning Costar 3695) using Solution 1. Following serial dilution each well has 50 µl of Solution 1. The reaction is started by adding 50 µl of solution 2 to each well. This may be done with a multichannel pipettor either manually or with automated liquid handling devices. The microtiter plate is then transferred to a microplate absorbance reader and multiple absorbance readings at 340 nm are taken for each well in a kinetic mode. The observed rate of change, which is proportional to the ATPase rate, is then plotted as a function of the compound concentration. For a standard $IC_{50}$ determination the data acquired is fit by the following four parameter equation using a nonlinear fitting program (e.g., Grafit 4):

$$y = \frac{\text{Range}}{1+\left(\frac{x}{\text{IC}_{50}}\right)^s} + \text{Background}$$

where y is the observed rate and x is the compound concentration.

What is claimed is:

1. A method for the treatment of a cellular proliferative disease comprising administering to a subject in need thereof a pharmaceutical composition comprising a compound of Formula I:

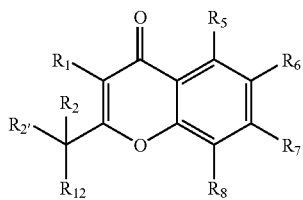

Formula I or a pharmaceutically acceptable salt, hydrate, or mixture thereof, wherein:

$R_1$ is chosen from optionally substituted aryl-$C_1$-$C_4$ alkyl and optionally substituted heteroaryl-$C_1$-$C_4$ alkyl;

$R_2$ and $R_{2'}$ are independently chosen from hydrogen, optionally substituted alkyl-, optionally substituted alkoxy, optionally substituted aryl-, optionally substituted aralkyl-, optionally substituted heteroaryl-, and optionally substituted heteroaralkyl;

$R_{12}$ is —N($R_4$)(COR$_3$);

$R_3$ is optionally substituted aryl;

$R_4$ is $R_{16}$-alkylene- wherein $R_{16}$ is hydroxyl, di($C_1$-$C_4$ alkyl)amino-, ($C_1$-$C_4$ alkyl)amino-, amino, $C_1$-$C_4$-alkoxy, or N-heterocyclyl; and $R_5$, $R_6$, $R_7$ and $R_8$ are independently chosen from hydrogen, acyl, optionally substituted alkyl, optionally substituted alkoxy, halogen, hydroxyl, nitro, cyano, dialkylamino, alkylsulfonyl, alkylsulfonamido-, alkylthio-, carboxyalkyl-, carboxamido-, aminocarbonyl-, optionally substituted aryl and optionally substituted heteroaryl.

2. A method according to claim 1, wherein if either $R_2$ or $R_{2'}$ is hydrogen, then the other is not hydrogen.

3. A method according to claim 1 wherein $R_5$, $R_6$, $R_7$ and $R_8$ are each independently selected from hydrogen, hydroxyl, halogen, $C_1$-$C_4$ alkyl, $C_1$-$C_4$ haloalkyl, $C_1$-$C_4$ alkoxy, $C_1$-$C_4$ haloalkoxy and cyano.

4. A method according to claim 3, wherein $R_5$, $R_6$, $R_7$ and $R_8$ are each independently selected from hydrogen, cyano, methoxy, and halogen.

5. A method according to claim 4, wherein $R_5$, $R_6$, and $R_8$ are each hydrogen and $R_7$ is cyano, methoxy or halogen.

6. A method according to claim 1, wherein $R_2$ is optionally substituted $C_1$-$C_4$ alkyl and $R_{2'}$ is hydrogen or optionally substituted $C_1$-$C_4$ alkyl.

7. A method according to claim 6, wherein $R_{2'}$ is hydrogen and $R_2$ is optionally substituted $C_1$-$C_4$ alkyl.

8. A method according to claim 7, wherein $R_{2'}$ is hydrogen and $R_2$ is ethyl or propyl.

9. A method according to claim 8, wherein $R_2$ is i-propyl.

10. A method according to claim 1, wherein $R_1$ is optionally substituted phenyl-$C_1$-$C_4$-alkyl- or optionally substituted naphthalenylmethyl.

11. A method according to claim 1, wherein $R_1$ is benzyl, chlorobenzyl, methylbenzyl, methoxybenzyl, cyanobenzyl, hydroxybenzyl, dichlorobenzyl, dimethoxybenzyl, or naphthalenylmethyl.

12. A method according to claim 11, wherein $R_1$ is benzyl-, cyanobenzyl-, methoxybenzyl-, or naphthalenylmethyl.

13. A method according to claim 12, wherein $R_1$ is benzyl.

14. A method according to claim 1, wherein $R_3$ is chosen from phenyl; and phenyl substituted with one or more substituents chosen from: halo, $C_1$-$C_4$ alkyl, $C_1$-$C_4$ alkyl substituted with hydroxyl, $C_1$-$C_4$ alkoxy, $C_1$-$C_4$ alkyl substituted with $C_1$-$C_4$ alkoxy, nitro, formyl, carboxy, cyano, methylenedioxy, ethylenedioxy, acyl, —N-acyl, and trifluoromethyl.

15. A method according to claim 14, wherein $R_3$ is chosen from phenyl, halophenyl, dihalophenyl, cyanophenyl, halo(trifluoromethyl)phenyl, hydroxymethylphenyl, methoxyphenyl, ethoxyphenyl, carboxyphenyl, ethylphenyl, tolyl, methoxychlorophenyl, methylhalophenyl, and trifluoromethylphenyl.

16. A method according to claim 15, wherein $R_3$ is tolyl, halophenyl, halomethylphenyl, hydroxymethylphenyl, formylphenyl or cyanophenyl.

17. A method according to claim 1, wherein $R_4$ is $R_{16}$-alkylene-, and $R_{16}$ is amino.

18. A method for the treatment of a cellular proliferative disease comprising administering to a subject in need thereof a composition comprising a compound of Formula I

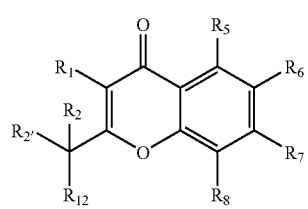

Formula I or a pharmaceutically acceptable salt, hydrate, or mixture thereof wherein $R_1$ is benzyl, halobenzyl, methoxybenzyl-, cyanobenzyl, or naphthalenylmethyl-;

$R_2$ is ethyl or propyl;

$R_{2'}$ is hydrogen;

$R_5$ is hydrogen;

$R_6$ is hydrogen;

$R_7$ is halo, cyano, methoxy or hydrogen;

$R_8$ is hydrogen; and $R_{12}$ is —NR$_4$(COR$_3$) wherein $R_3$ is optionally substituted aryl and $R_4$ is $R_{16}$-alkylene- wherein $R_{16}$ is chosen from hydroxyl, di($C_1$-$C_4$ alkyl)amino, ($C_1$-$C_4$ alkyl)amino, amino, pyrrolidino, piperidino, imidazolyl and morpholino.

19. A method according to claim 1 wherein $R_2$ and $R_{2'}$ are each attached to a stereogenic center having an R-configuration.

20. A method according to claim 1 wherein a hydrochloric, phosphoric, or oxalic acid salt of a compound of Formula I is administered.

21. A method according to claim 1, wherein said composition further comprises a chemotherapeutic agent other than a compound of Formula I or a pharmaceutically acceptable salt, hydrate, or mixture thereof.

22. A method according to claim 21, wherein said composition further comprises a taxane.

23. A method according to claim 21, wherein said composition further comprises a vinca alkaloid.

24. A method according to claim 21, wherein said composition further comprises a topoisomerase I inhibitor.

25. A method according to claim 20, wherein a hydrochloric acid salt of a compound of Formula I is administered.

26. A method according to claim 25, wherein a hydrochloric acid salt monohydrate of a compound of Formula I is administered.

* * * * *